(12) United States Patent
Qiu et al.

(10) Patent No.: US 10,758,594 B2
(45) Date of Patent: *Sep. 1, 2020

(54) BIOMATERIAL DEVICES AND TOPICAL COMPOSITIONS FOR TREATMENT OF SKIN ABNORMALITIES

(71) Applicant: Marine Essence Biosciences Corporation of USA, Chino, CA (US)

(72) Inventors: Danny Qiu, Chino Hills, CA (US); Sergio Madrigal Carballo, Madison, WI (US)

(73) Assignee: Marine Essence Biosciences Corporation of USA, Chino, CA (US)

( * ) Notice: Subject to any disclaimer, the term of this patent is extended or adjusted under 35 U.S.C. 154(b) by 89 days.

This patent is subject to a terminal disclaimer.

(21) Appl. No.: 16/123,986

(22) Filed: Sep. 6, 2018

(65) Prior Publication Data

US 2019/0388517 A1  Dec. 26, 2019

Related U.S. Application Data

(60) Provisional application No. 62/689,966, filed on Jun. 26, 2018.

(51) Int. Cl.
| | | |
|---|---|---|
| *A61K 38/39* | (2006.01) | |
| *A61K 31/722* | (2006.01) | |
| *A61K 31/728* | (2006.01) | |
| *A61P 17/02* | (2006.01) | |
| *A61K 35/616* | (2015.01) | |
| *A61K 9/00* | (2006.01) | |
| *A61K 9/06* | (2006.01) | |
| *A61K 35/618* | (2015.01) | |
| *A61L 27/24* | (2006.01) | |
| *A61L 27/48* | (2006.01) | |
| *A61L 27/52* | (2006.01) | |
| *A61L 27/20* | (2006.01) | |
| *A61L 27/26* | (2006.01) | |
| *A61L 27/56* | (2006.01) | |

(52) U.S. Cl.
CPC ............ *A61K 38/39* (2013.01); *A61K 9/0014* (2013.01); *A61K 9/06* (2013.01); *A61K 31/722* (2013.01); *A61K 31/728* (2013.01); *A61K 35/616* (2013.01); *A61K 35/618* (2013.01); *A61L 27/20* (2013.01); *A61L 27/24* (2013.01); *A61L 27/26* (2013.01); *A61L 27/48* (2013.01); *A61L 27/52* (2013.01); *A61L 27/56* (2013.01); *A61P 17/02* (2018.01); *A61L 2300/412* (2013.01); *A61L 2430/34* (2013.01)

(58) Field of Classification Search
CPC .................................................... A61K 38/39
See application file for complete search history.

(56) References Cited

U.S. PATENT DOCUMENTS

| | | | |
|---|---|---|---|
| 4,559,157 A | 12/1985 | Smith et al. | |
| 4,608,392 A | 8/1986 | Jacquet et al. | |
| 4,820,508 A | 4/1989 | Wortzman | |
| 4,992,478 A | 2/1991 | Geria | |
| 6,821,530 B2 * | 11/2004 | Koob | C08H 1/06 |
| | | | 424/458 |
| 7,482,503 B2 | 1/2009 | Gregory et al. | |
| 8,097,288 B1 | 1/2012 | Dreher | |
| 8,178,137 B2 | 5/2012 | Liker | |
| 8,221,806 B2 | 7/2012 | Aviram et al. | |
| 8,263,140 B1 | 9/2012 | Dreher et al. | |
| 8,372,454 B2 | 2/2013 | Aviram et al. | |
| 8,609,152 B2 | 12/2013 | Madjid et al. | |
| 8,642,088 B2 | 2/2014 | Reed et al. | |
| 8,658,220 B2 | 2/2014 | Bates et al. | |
| 8,734,868 B1 | 5/2014 | Aviram | |
| 8,758,832 B1 | 6/2014 | Anderson et al. | |

(Continued)

FOREIGN PATENT DOCUMENTS

| | | | |
|---|---|---|---|
| CN | 105533710 A | * | 5/2016 |
| CR | 20160158 A | | 8/2016 |

OTHER PUBLICATIONS

Remington's. "Remington's Pharmaceutical Science 17th Edition". Gannaro, A (Ed.). pp. 1513. (Year: 1985).*

(Continued)

*Primary Examiner* — Amy L Clark
(74) *Attorney, Agent, or Firm* — Squire Patton Boggs (US) LLP

(57) ABSTRACT

Devices for guided tissue regeneration (GTR) include a matrix of chitosan and mutable collagenous tissue (MCT) wherein the chitosan is electrostatically bonded to the MCT to form MCT-chitosan composite material. The MCT can be isolated from invertebrate marine organisms, such as sponges, jellyfish, mollusks and echinoderms. The MCT-chitosan composite material can be formulated as a biofilm, a 3D-sponge, a hydrogel, or as an electrospun nanofiber, or the MCT-chitosan composite material can coat a biomaterial surface. The devices can include wound dressings and tissue sponges, including 3D sponges. Applications include tissue engineering and wound healing, as well as burns and other related guided tissue regeneration applications. MCT and MCT-chitosan composite material, contained in a pharmaceutically acceptable topical carrier, also has cosmeceutical applications, for treating scars, as well as skin discoloration and various pigmentation issues, including melasma/chloasma.

17 Claims, 32 Drawing Sheets

(24 of 32 Drawing Sheet(s) Filed in Color)

(56) References Cited

U.S. PATENT DOCUMENTS

| | | | |
|---|---|---|---|
| 8,889,199 | B1 | 11/2014 | Anderson et al. |
| 9,017,742 | B2 | 4/2015 | Liker |
| 9,545,423 | B2 | 1/2017 | Reed et al. |
| 9,901,536 | B2 | 2/2018 | Lee |
| 9,962,464 | B2 | 5/2018 | Liu et al. |
| 9,980,894 | B2 | 5/2018 | Herrmann et al. |
| 2002/0037940 | A1 | 3/2002 | Koob et al. |
| 2006/0069011 | A1 | 3/2006 | Kusanagi et al. |
| 2015/0017213 | A1 | 1/2015 | Adkins, Jr. et al. |

OTHER PUBLICATIONS

Mahalingam et al. "Semisolid Dosages: Ointments, Creams, and Gels" from "Pharmaceutical Manufacturing Handbook: Production and Process". Gad, S., Ed.. Wiley. pp. 267-269. (Year: 2008).*
Barbaglio et al., "The smart connective tissue of echinoderms: a materializing promise for biotech applications," Cah Biol Mar. Jan. 2013; 54(4): 713-720.
Cheng et al., "Isolation, Characterization and Evaluation of Collagen from Jellyfish *Rhopilema esculentum* Kishinouye for Use in Hemostatic Applications", PLoS One. Jan. 19, 2017; 12(1):e0169731, 21 pages.
Chhabra et al., "Optimization, characterization, and efficacy evaluation of 2% chitosan scaffold for tissue engineering and wound healing", J Pharm Bioallied Sci. Oct.-Dec. 2016; 8(4): 300-308.
Costa-Pinto et al., "Adhesion, Proliferation, and Osteogenic Differentiation of a Mouse Mesenchymal Stem Cell Line (BMC9) Seeded on Novel Melt-Based Chitosan/Polyester 3D Porous Scaffolds", Tissue Eng Part A. Jun. 2008; 14(6): 1049-1057.
Cui et al., "Characterization and subunit composition of collagen from the body wall of sea cucumber *Stichopus japonicus*", Food Chem. 2007; 100(3): 1120-1125.
Di Benedetto et al., "Production, Characterization and Biocompatibility of Marine Collagen Matrices from an Alternative and Sustainable Source: The Sea Urchin *Paracentrotus lividus*", Mar Drugs. Sep. 24, 2014; 12(9): 4912-4933.
Ferrario et al., "Marine-derived collagen biomaterials from echinoderm connective tissues", Mar Environ Res. Jul. 2017; 128: 46-57. Epub Mar. 31, 2016.
Fraser et al., "Chain Conformation in the Collagen Molecule", J Mol Biol. Apr. 15, 1979; 129(3): 463-481.
Gelse et al., "Collagens—structure, function, and biosynthesis", Adv Drug Deliv Rev. Nov. 28, 2003; 55(12): 1531-1546.
Gómez-Guillén et al., "Functional and bioactive properties of collagen and gelatin from alternative sources: A review", Food Hydrocoll. Dec. 2011; 25(8): 1813-1827.
Han et al., "Processing Optimization and Physicochemical Characteristics of Collagen from Scales of Yellowfin Tuna (*Thunnus albacares*)", Fish Aqua Sci. 2010; 13(2): 102-111.

Ji et al., "Biocompatibility study of a silk fibroin-chitosan scaffold with adipose tissue-derived stem cells in vitro", Exp Ther Med. Aug. 2013; 6(2): 513-518. Epub Jun. 26, 2013.
Kittiphattanabawon et al., "Characteristics of Pepsin-Solubilised Collagen from the Skin of Splendid Squid (*Loligo formosona*)", J Chem. 2015; Article ID 482354, 8 pages.
Kumar et al., "Chitosan Chemistry and Pharmaceutical Perspectives", Chem Rev. Dec. 2004; 104(12): 6017- 6084.
Li et al., "Studies on bullfrog skin collagen", Food Chem. Jan. 2004; 84(1): 65-69.
Lin et al., "Three dimensional chitosan scaffolds influence the extra cellular matrix expression in Schwann cells", Mater Sci Eng C Mater Biol Appl. Sep. 2014; 42: 474-478. Epub Jun. 6, 2014.
Ma et al., "A preliminary in vitro study on the fabrication and tissue engineering applications of a novel chitosan bilayer material as a scaffold of human neofetal dermal fibroblasts", Biomaterials. Feb. 2001; 22(4): 331-336.
Ma et al., "Collagen/chitosan porous scaffolds with improved biostability for skin tissue engineering", Biomaterials. Nov. 2003; 24(26): 4833-4841.
Madrigal-Carballo et al., "Polymer-liposome nanoparticles obtained by the electrostatic bio-adsorption of natural polymers onto soybean lecithin liposomes", Int J Nanoparticles. 2012; 5(3): 196-209.
Madrigal-Carballo et al., "Protein-loaded chitosan nanoparticles modulate uptake and antigen presentation of hen egg-white lysozyme by murine peritoneal macrophages", Int J Nanoparticles. 3(2); 2010: 179-191.
Park et al., "Platelet derived growth factor releasing chitosan sponge for periodontal bone regeneration", Biomaterials. Jan. 2000; 21(2): 153-159.
Silva et al., "Marine Origin Collagens and its Potential Applications", Mar Drugs. Dec. 2014; 12(12): 5881-5901.
Tang et al., "Agarose/collagen composite scaffold as an anti-adhesive sheet", Biomed Mater. Sep. 2007; 2(3): S129-S134. Epub Jul. 30, 2007.
Wilkie, I.C., "Mutable Collagenous Tissue: Overview and Biotechnological Perspective," Prog Mol Subcell Biol. 2005; 39: 221-50.
Wong, D. W. S. *Mechanism and Theory in Food Chemistry*, Second Edition. Switzerland, Springer International Publishing AG, 2018.
Zhang et al., "Novel chitosan/collagen scaffold containing transforming growth factor-β1 DNA for periodontal tissue engineering", Biochem Biophys Res Commun. May 26, 2006; 344(1): 362-369. Epub Mar. 29, 2006.
Zhong et al., "Isolation and Characterization of Collagen from the Body Wall of Sea Cucumber *Stichopus monotuberculatus*", J Food Sci. Apr. 2015; 80(4): C671-C679. Epub Mar. 21, 2015.
U.S. Appl. No. 16/123,942, filed Sep. 6, 2018, Danny Qiu et al.
Miles and Bailey, "Thermal Denaturation of Collagen Revisited". In: *Proc. Indian Acad. Sci.* (*Chem Sci.*), vol. 111, No. 1, Feb. 1999, pp. 71-80.

* cited by examiner

FIG. 11A
FIG. 11B
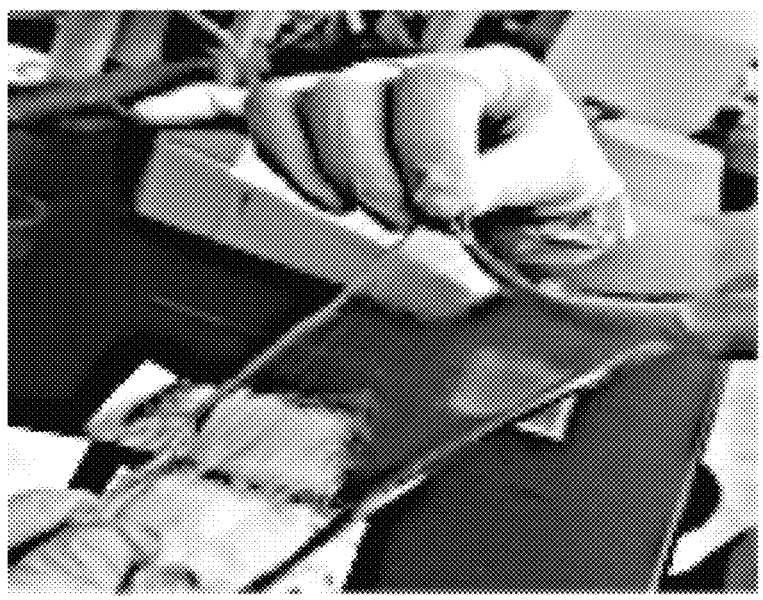
MCT-chitosan wound dressing templates
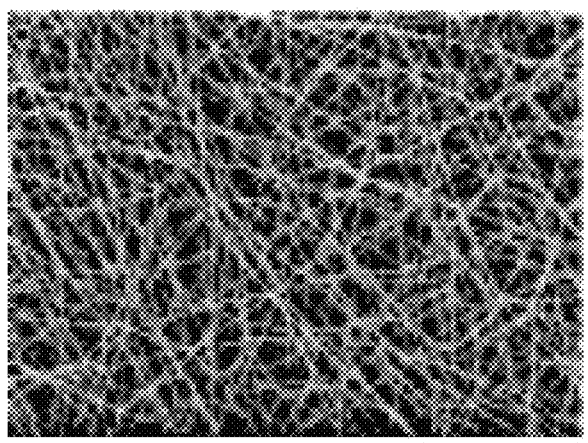
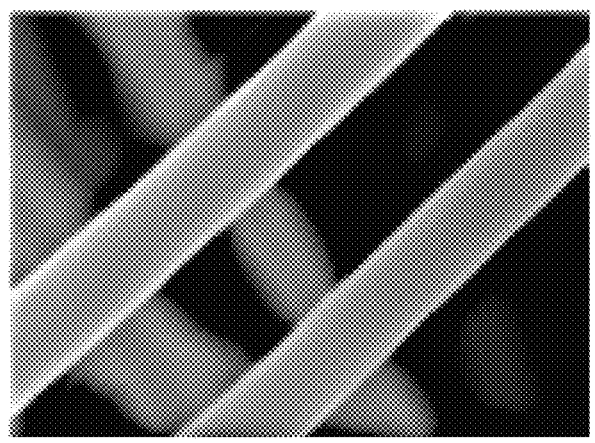
MCT-chitosan electrospun nanofibers
FIG. 11C
FIG. 11D

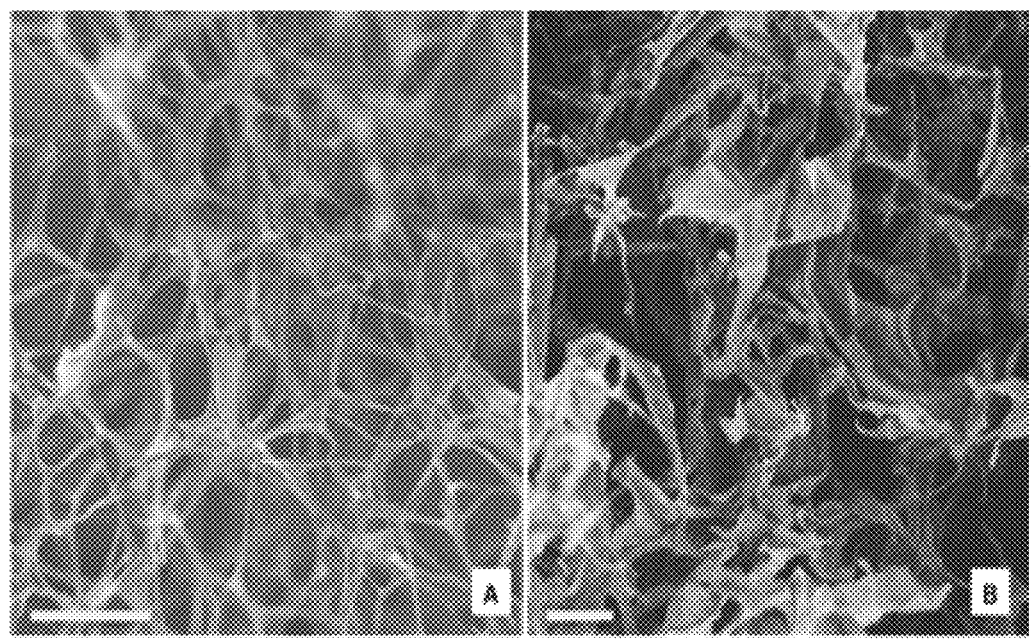
FIG. 16A  FIG. 16B
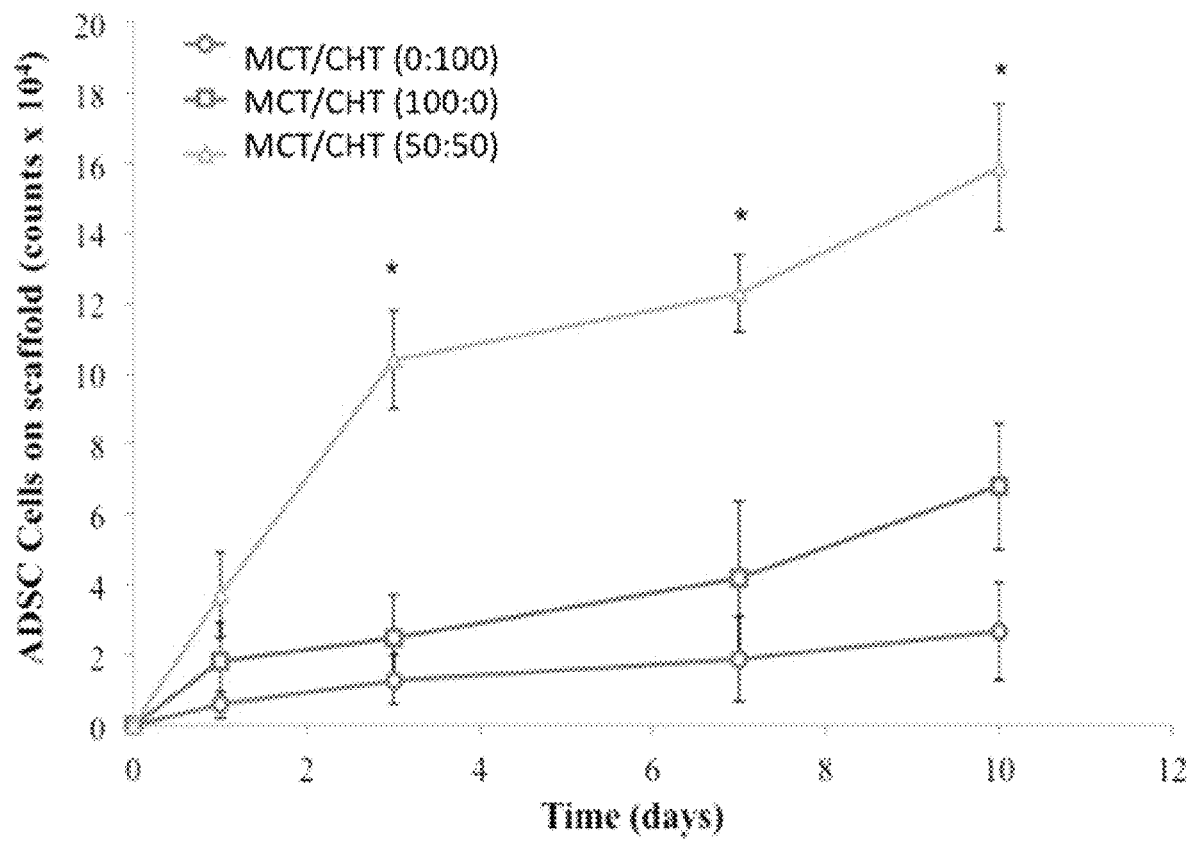
FIGURE 17

MCT-Chitosan NFs

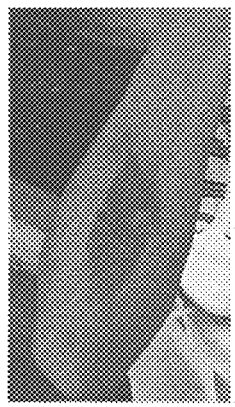 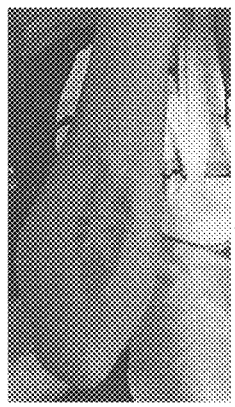 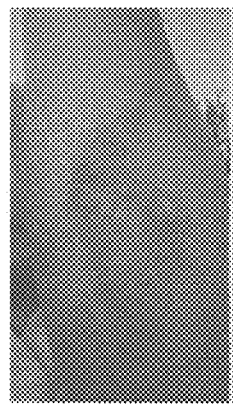 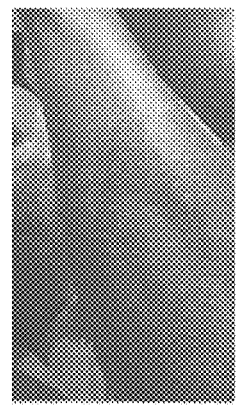
FIG. 34A	FIG. 34B	FIG. 34C	FIG. 34D
FIG. 35A
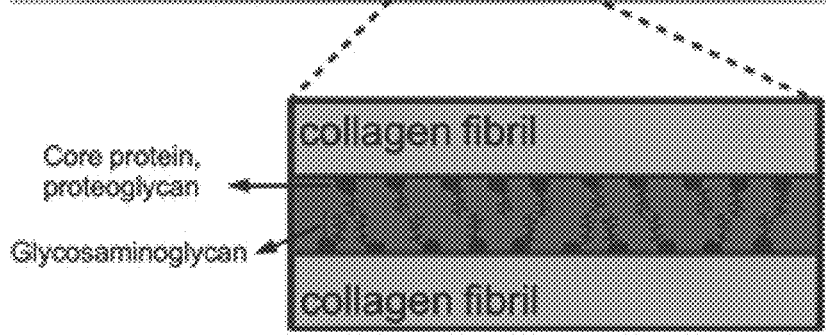
FIG. 35B
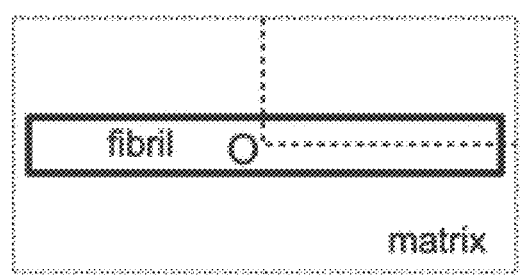
FIG. 35C

BIOMATERIAL DEVICES AND TOPICAL COMPOSITIONS FOR TREATMENT OF SKIN ABNORMALITIES

CROSS-REFERENCE TO RELATED APPLICATIONS

The present application claims benefit of U.S. Provisional Application No. 62/689,966 filed Jun. 26, 2018 and incorporates by reference that provisional application in its entirety.

FIELD OF THE INVENTION

Aspects of the present invention relate to biomaterial devices for guided tissue regeneration (GTR). More specifically, aspects of the invention relate to tissue sponges, wound dressings, cosmeceutical compositions and other devices and topical compositions comprising mutable collagenous tissue (MCT) for effecting GTR. Still more specifically, aspects of the invention relate to such devices comprising composites of MCT and chitosan biopolymer (CHT) for effecting GTR. Aspects of the invention also relate to treatment of burns, wounds, ulcers, and other lesions and related skin disorders, by applying MCT, either alone or as a composite, in biomaterial devices to promote GTR. Aspects of the invention also relate to treatment of skin abnormalities, such as scars and skin discolorations, the discolorations including chloasma, by applying MCT and/or MCT-chitosan composites in cosmeceutical formulations.

BACKGROUND OF THE INVENTION

Natural polymers have been used in many pharmaceutical applications and medical device technologies. One natural polymer, chitosan (sometimes referred to herein as CHT), has been used for the preparation of nanoparticles, microspheres, hydrogels, films, fibers, and tablets. Chitosan has been used to prepare potential drug delivery systems such as oral, nasal, parenteral, transdermal and ophthalmic formulations. Chitosan has also been used to prepare wound dressings and tissue sponges (Kumar et al., Chem. Rev. 2004, 104, 6017-6084). However, chitosan formulations and materials suffer from numerous drawbacks including limited stability, biodegradability and tensile strength. Materials such as modified chitosan and synthetic composite materials have been tested for many of the same uses for which chitosan has been evaluated, but many of these materials suffer from similar drawbacks, including insufficient biocompatibility.

Accordingly, there is a need for new materials that are biocompatible and biodegradable, and that have suitable stability and mechanical properties and performance for use in human and other mammalian treatments and therapies. These new materials and compositions would preferably have advantages over chitosan alone, such as additional and/or improved biocompatibility, high stability and improved physical and biological properties. The ability to use these materials as tissue sponges, wound dressings, cosmeceuticals, and/or systems for the delivery of therapeutic agents would further aid researchers in the areas of biomedical engineering, biomaterials, and tissue engineering.

SUMMARY

Embodiments of the invention provide biodegradable and biocompatible mutable collagenous tissue (MCT) and MCT-chitosan composite materials. These composites can be formed into a variety of materials such as hydrogels, biofilms, three-dimensional sponges, and nanofibers. The MCT-chitosan composite materials are stronger and have better mechanical properties than known chitosan materials. The MCT component of the composites adds biocompatibility, cell attachment, physical and chemical stability, and improved mechanical properties to the antimicrobial and hemostatic properties of the chitosan component, thereby significantly increasing the effectiveness of the composite in therapeutic applications.

Accordingly, in one aspect the invention provides a composition comprising a MCT, or a matrix of MCT and chitosan (CHT), in which the MCT is isolated from marine invertebrates. In the matrix, the CHT may be linked to the MCT by means of electrostatic interactions, such as hydrogen bonding and dipole-dipole interaction, to form MCT-CHT composite material. In one aspect, the MCT-chitosan composite comprises a polyelectrolyte crosslinked structure between GAG and collagen in MCT, and its interaction with N-glucosamine units on chitosan. The mutable collagenous tissue can comprise collagen and glycosaminoglycan (GAG).

In one aspect, the MCT can comprise collagen and chondroitin sulfate. The compositions, or the MCT used to form the composition, can be substantially comprised of type-I collagen. The chitosan can have a deacetylation degree of about 60% to about 99%. The mean molecular weight of the chitosan can be about 20 kDa to about 400 kDa. In some embodiments, the mass ratio of the MCT in the composite material can be 100:0 to 10:90 of the mass ratio of the chitosan in the composite material. In some embodiments, the mass ratio of the MCT is about 100:0 to 50:50 of the mass ratio of the chitosan.

By the selection of appropriate marine invertebrate sources (e.g., sponges, jellyfish, mollusks and echinoderms) and isolation procedures, the amount and proportion of MCT obtained with higher yield of collagen and glycosaminoglycan can be controlled. For example, MCTs with higher content of type-I collagen, a fibrillar type of collagen that is a key structural composition of several connective tissues, can be isolated and used in the compositions described herein. Additionally, the MCTs isolated can be biased or controlled in terms of the nature of type of fibrillary collagen (I, II, III, V, XI) and glycosaminoglycan (chondroitin sulfate, hyaluronic acid), as well as their structural heterogeneity.

In one embodiment, the MCT can be isolated from marine invertebrates, such as sponges, jellyfish, mollusks, and echinoderms. In a more particular embodiment, the MCT will be isolated from marine invertebrate echinoderms, such as sea urchins and sea cucumbers. In a yet more particular embodiment, the MCT will be isolated from sea cucumbers.

In another embodiment, MCT can be composed of collagen. In a more particular embodiment the collagen can be fibrillar collagen type I, II, III, V or XI. In a yet more particular embodiment, fibrillar collagen is type-I. By the isolation processes described herein, fibrillar collagen type-I can be selectively isolated.

In another embodiment, the MCT can comprise collagen and glycosaminoglycan. In some embodiments, the glycosaminoglycan can include chondroitin sulfate, hyaluronic acid, heparin, keratan sulfate, heparan sulfate and/or dermatan sulfate or a mixture of both components. In another embodiment, glycosaminoglycan in MCT will comprise chondroitin sulfate and/or hyaluronic acid or a mixture of both components.

The MCT and MCT-chitosan composition can be a hydrogel, a biofilm, a 3D-sponge, or a nanofiber. Nanoparticles can be formulated into various therapeutic agent delivery systems, such as oral solutions, IV solutions, or aerosols. Biofilms can be formed into wound healing, surface coating, or packaging materials. 3D-sponges can be used as sponges, such as for tissue engineering and wound dressing templates. Nanofibers can be formulated as wound dressing templates or surface coating agents.

In some embodiments, the MCT and MCT-CHT composite material can be crosslinked, by means of physical and/or chemical processes. Physical crosslinking can be accomplished by radiation treatment (UV, gamma) and/or thermal treatment. Chemical crosslinking can be accomplished by adding a crosslinking agent to MCT or MCT-chitosan composite, the amounts of crosslinking agent used in crosslinked biomaterials, with respect to the content of MCT, can be about 0.1 to about 1.0%. Crosslinking agents that can be used include glutaraldehyde, ethyl-dimethyl-carbodiimide (EDC)-N-hydroxysuccinimide (NHS), riboflavin, genipin, and the like.

The MCT and the MCT-chitosan composite material can also be formulated as a biofilm of a 3D-sponge with improved water absorption, thermal stability, vapor permeation and cell attachment. In such embodiments, the biofilms and/or 3D-sponges will be suitable as sponges for tissue engineering, and wound dressing templates for surgical and medical applications.

Aspects of the invention also provide a method for delivering a bioactive agent to a mammal, the method comprising administering to a mammal MCT or MCT-chitosan composite material described herein. The MCT and MCT-chitosan composite materials can form a nanoparticle, nanofiber, hydrogel, biofilm or 3D-sponge that encapsulates the bioactive agent, for example, a drug or nutrient. Examples of drugs, vitamins, and nutrients that can be incorporated into formulations include lipids such as fatty acids, including omega-3 and omega-6 fatty acids, fat soluble vitamins (e.g., vitamin A, D, E, and/or K), antibiotics (e.g., amoxicillin, ampicillin, clindamycin, doxycycline, erythromycin, metronidazole, penicillin, tetracycline, vancomycin, and the like), probiotics (e.g., lactic acid bacteria, bifidobacteria, and the like), active dermal compounds (e.g., retinoic acid, tranexamic acid, hydrogen peroxide, hydroquinone, cysteamine, azelaic acid, tyrosinase inhibitors and the like), micronutrients such as β-carotene and/or ascorbic acid, proteins, and peptides. In some embodiments, MCTs and other nutritional supplements can also be included in a MCT-chitosan composite matrix, or in a composition that includes a MCT-chitosan composite matrix.

The MCT and MCT-chitosan composite materials can be tailored to degrade over a range of rates under various conditions by varying the amounts of the components and methods for preparing the MCT and the composite materials. Thus, aspects of the invention also provide a method of preparing MCT and MCT-chitosan composite material. Aspects of the invention further provide for the use of a composition described herein for the manufacture of biomedical devices and medicaments useful for the treatment of conditions such as bacterial infection and/or fungal infection, burns, diabetic feet and inflammatory conditions in a mammal, such as a human.

In still further aspects, MCT and MCT-chitosan composite biomaterials may be provided as therapeutic cosmetics, or cosmeceuticals, to promote collagenesis, scar healing, wound healing, reduction of melisma and chloasma, and other skin-related benefits, using MCT or MCT-chitosan composites in conjunction with a pharmaceutically acceptable topical carrier, including but not limited to a solution, a suspension, a liquid, a gel, an ointment, a lotion, or a cream.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, ordinarily skilled artisans will understand that portions of the example or aspect may be used in combination with other examples or aspects according to embodiments of the invention.

In the drawings:

FIGS. 1A and 1B depict comparative structure between general collagen structure and general MCT structure.

FIG. 2 depicts general structure for glycosaminoglycans.

FIGS. 3A and 3B depict comparative morphology of collagen fibril structure between bovine collagen and MCT.

FIG. 4 depicts general structure of chitosan.

FIGS. 5A and 5B are schematic illustrations for the fabrication of MCT-chitosan composite materials according to an embodiment.

FIG. 6 is a schematic illustration for the fabrication of MCT-chitosan composite biofilms according to an embodiment.

FIG. 7 is a schematic illustration for the fabrication of MCT-chitosan composite 3D-Sponges according to an embodiment.

FIG. 8 is a schematic illustration for the fabrication of MCT-chitosan composite hydrogels according to an embodiment.

FIG. 9A is a schematic illustration for the fabrication of MCT-chitosan electrospun nanofibers, and FIG. 9B is a photograph of the resulting nanofibers according to an embodiment.

FIG. 10A depicts the effect of a cross-linking agent (Glutaraldehyde 0.1% v/v) on mechanical properties of MCT-CHT composite biofilms, and FIG. 10B depicts swelling behavior of MCT-CHT composite biofilms according to embodiments.

FIGS. 11A and 11B depict an illustrative representation of MCT-chitosan biofilms and their potential applications as wound dressing templates, and FIGS. 11C and 11D depict a morphological characterization of MCT-chitosan composite electrospun nanofibers by scanning electron microscopy (SEM).

Figure 12:
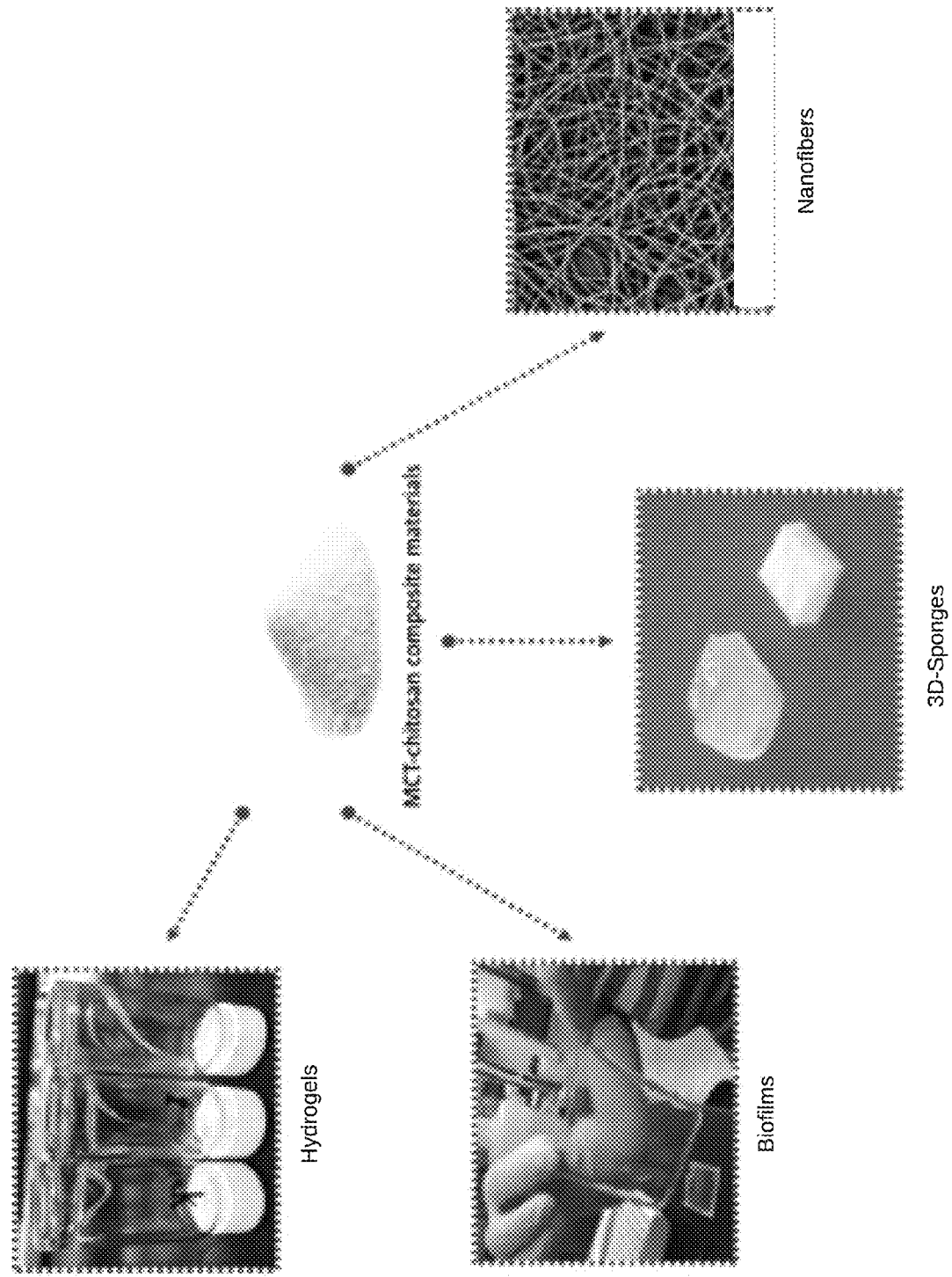

FIG. 12 is a schematic illustration of different MCT-chitosan composite materials, as used in GTR applications.

Figures 13A, 13B, 13C:
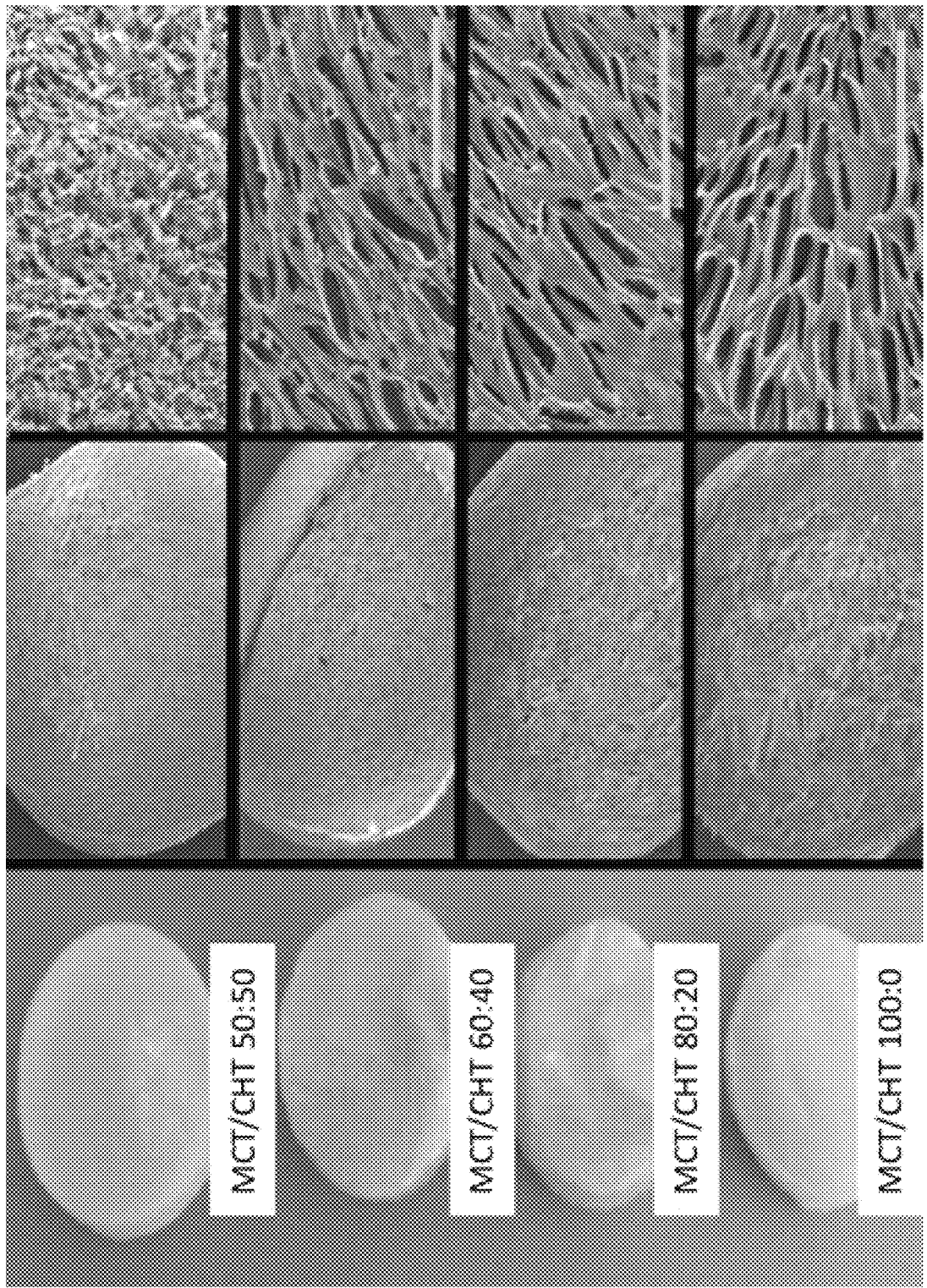

FIGS. 13A-13C depict the physical appearance of MCT-chitosan (MCT/CHT) composite 3D-sponges fabricated at different MCT/CHT mass ratios according to embodiments.

Figure 14:
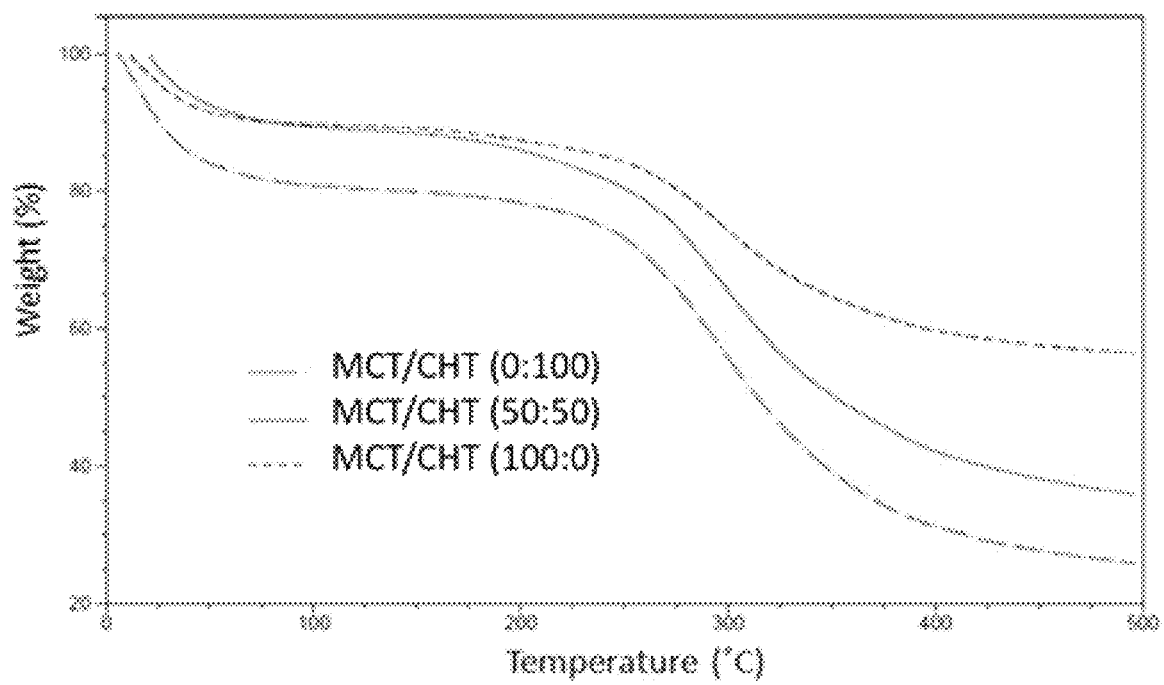

FIG. 14 depicts TGA thermograms for a MCT-chitosan composite 3D-sponges formulated at different MCT/CHT mass ratios.

Figure 15:
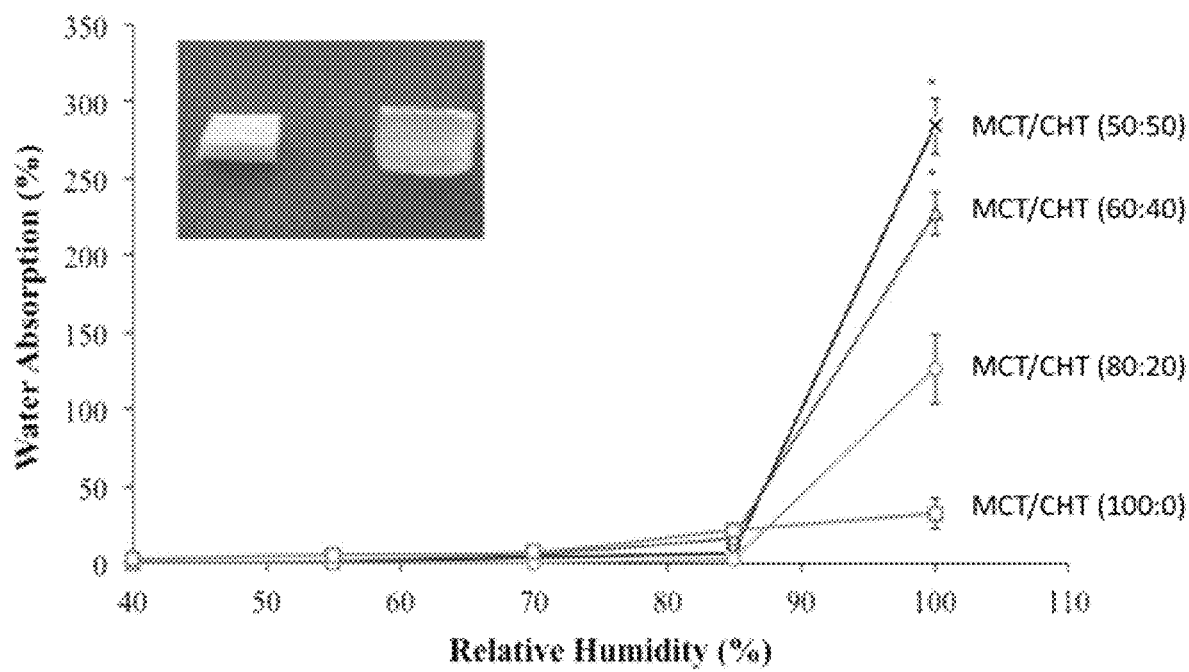

FIG. 15 depicts water absorption capacity for different MCT-chitosan composite 3D-sponges formulated at different mass ratios of MCT/CHT.

FIGS. 16A (no cells added) and 16B (cells added) are SEM micrographs showing the adsorption of ADSC cells onto MCT-CHT 3D-sponges.

FIG. 17 depicts a proliferation profile of ADSC cells cultured on MCT-chitosan composite 3D-sponges during a 15-day incubation period.

Figure 18:
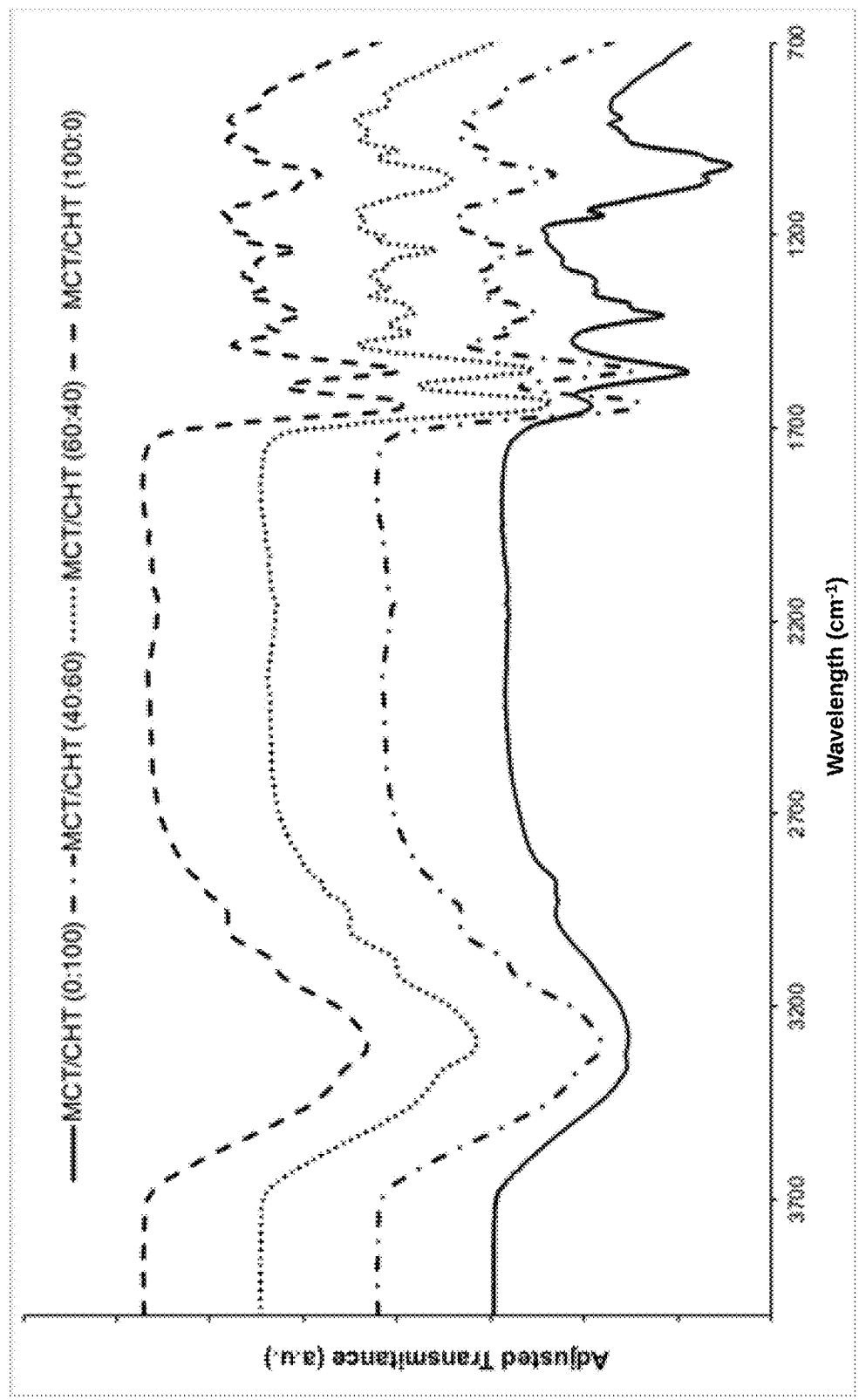

FIG. 18 depicts ATR-FTIR spectra of composite electrospun nanofibers (ESNF) fabricated at different mass ratios of MCT-chitosan composites.

Figure 19:
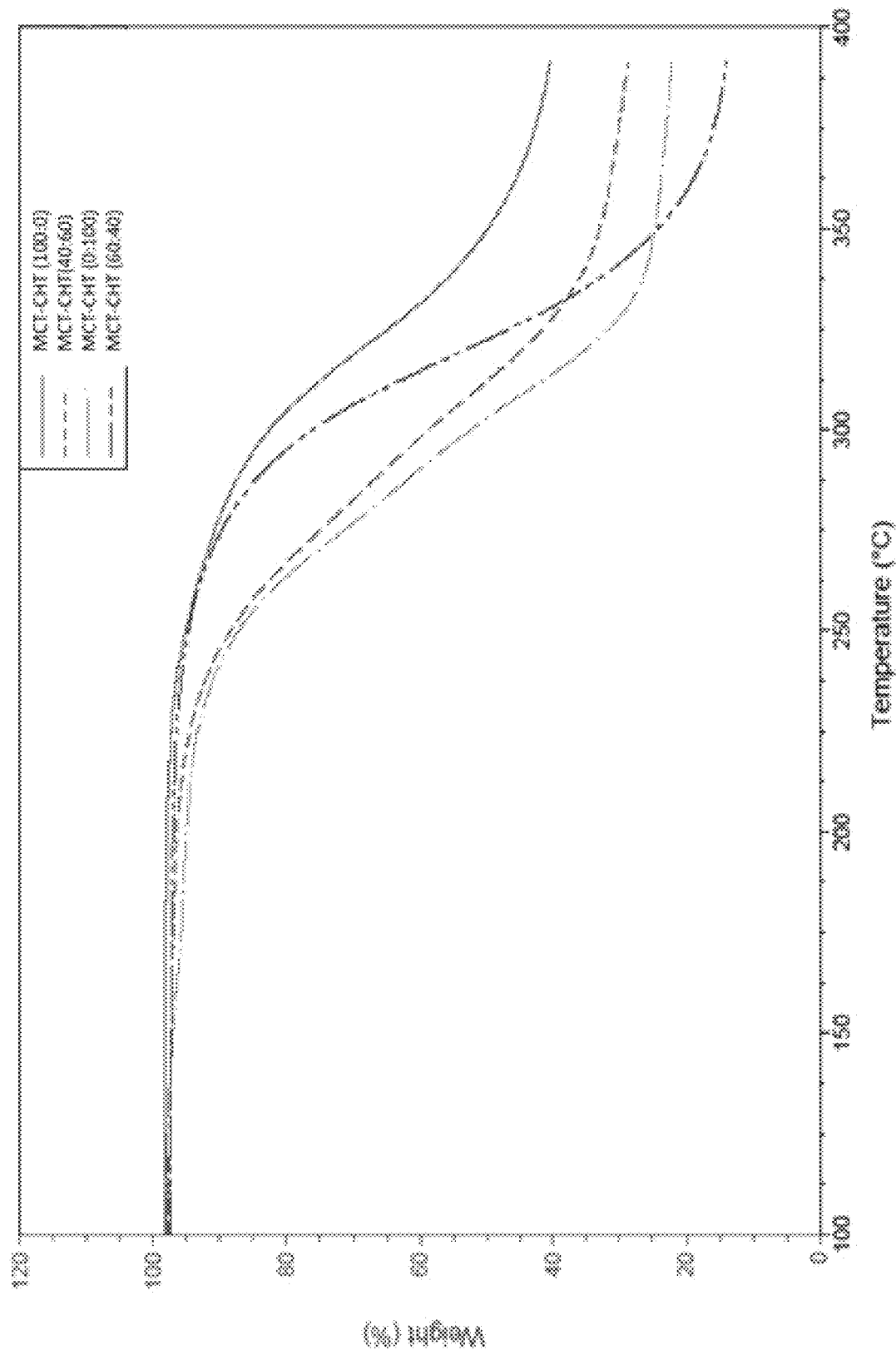

FIG. 19 depicts a thermal analysis by TGA for chitosan, MCT and MCT-chitosan composites.

Figure 20C:
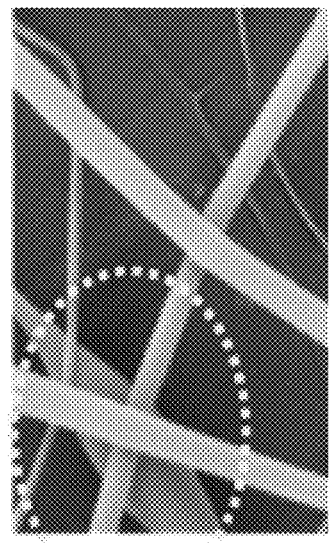
Figure 20B:
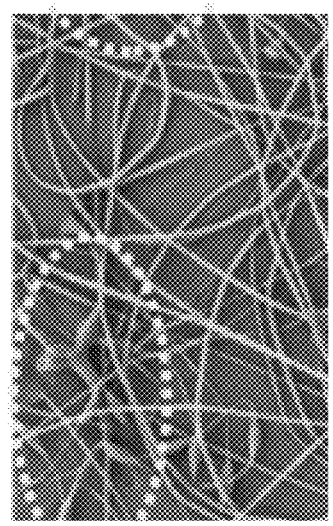
Figure 20A:
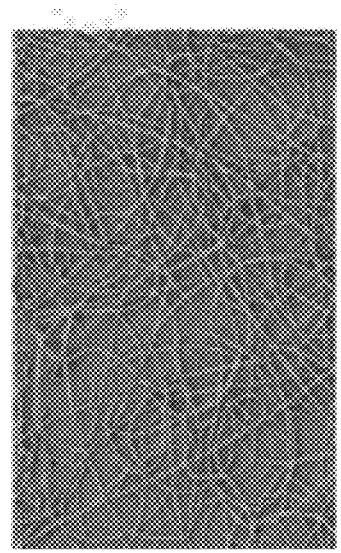
Figure 20F:
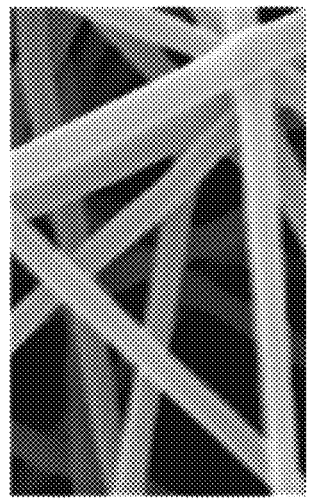
Figure 20E:
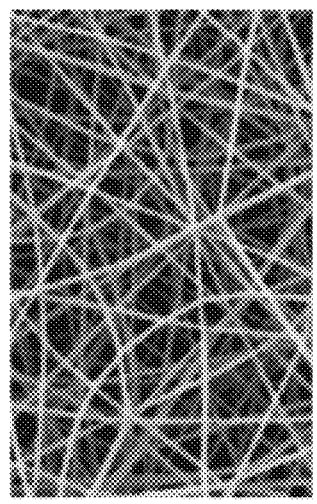
Figure 20D:
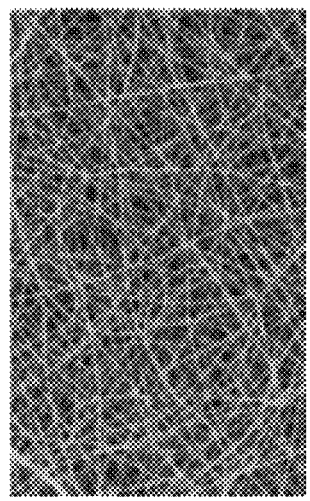

FIGS. 20A-20C are SEM micrographs of chitosan, and FIGS. 20D-20F are SEM micrographs of MCT-chitosan ESNFs, with a scale bar of 10 μm (FIGS. 20A and 20D), a scale bar of 2 μm (FIGS. 20B and 20E), and a scale bar of 200 nm (FIGS. 20C and 20F), in which circles indicate the presence of drops associated to bad electrospinning process in chitosan ESNFs, showing the improvement of MCT-chitosan composites for obtaining of electrospun nanofibers.

Figure 21:
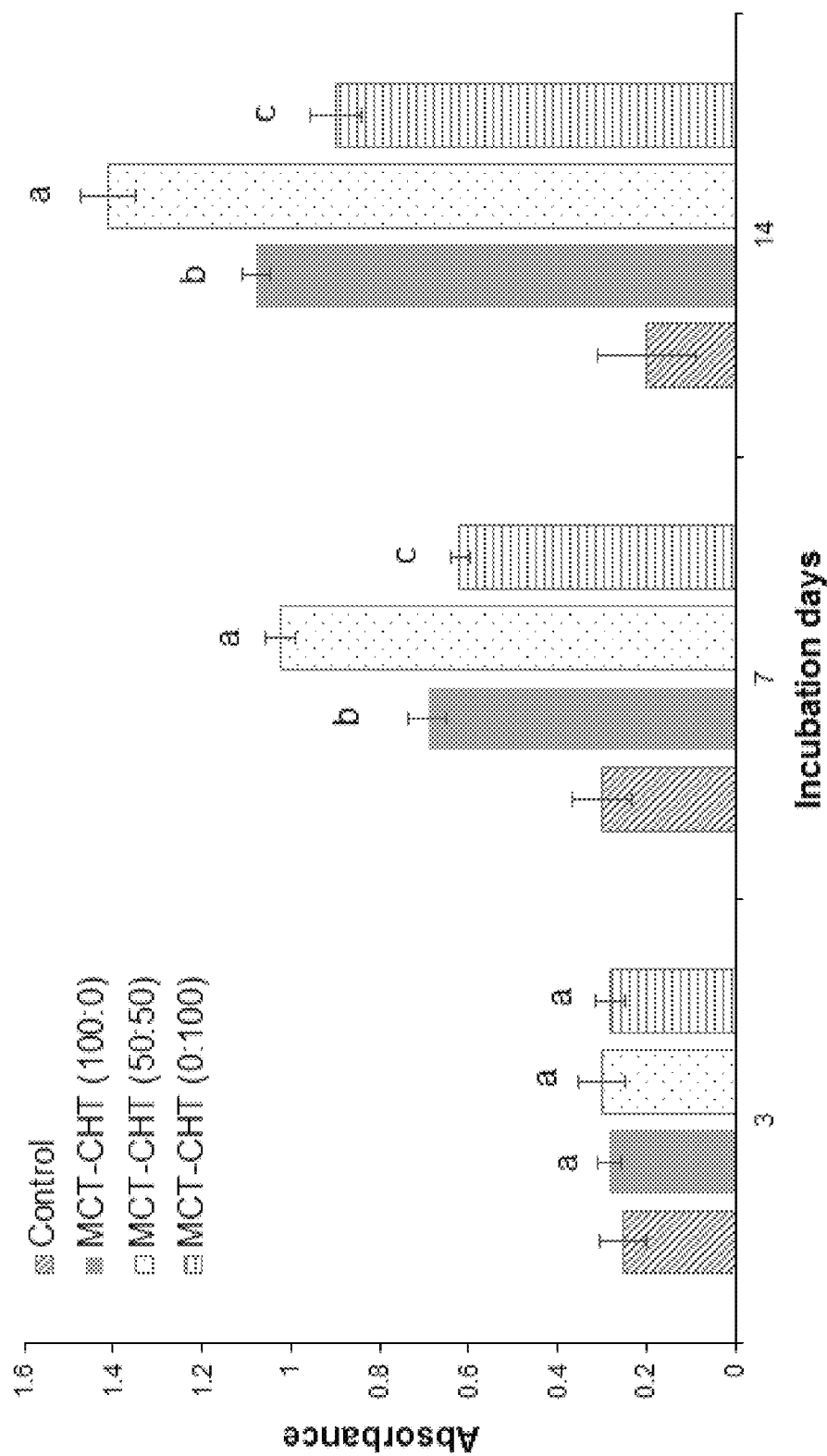

FIG. 21 depicts proliferation of L929 fibroblast cells co-cultured with chitosan, MCT and MCT-chitosan composite ESNFs.

Figure 22A:
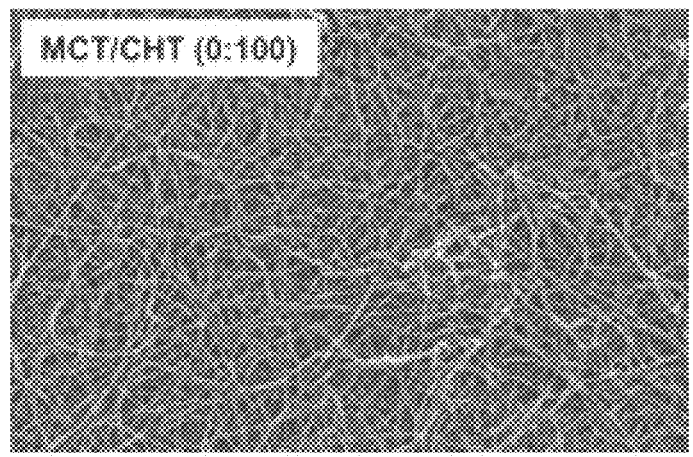
Figure 22B:
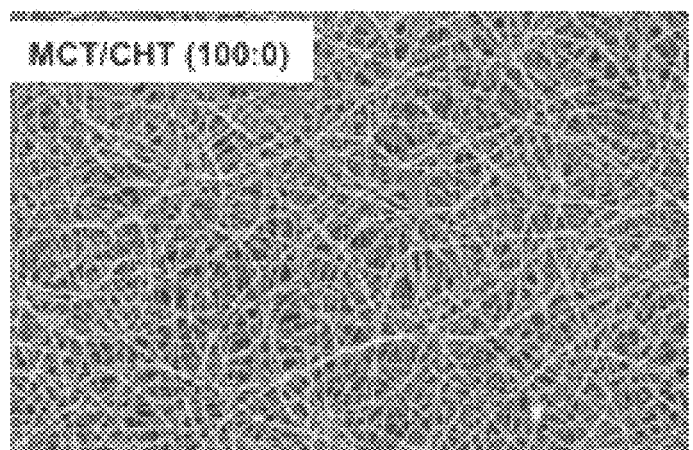
Figure 22C:
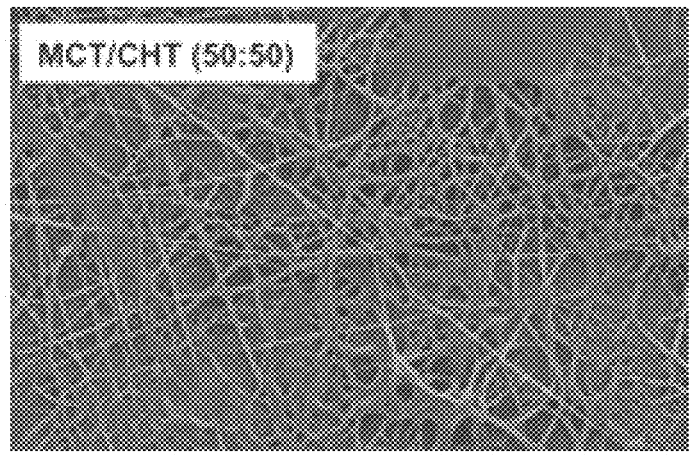

FIGS. 22A-22C are SEM micrographs showing cell adhesion onto chitosan (FIG. 22A), MCT-chitosan composite (FIG. 22B) and MCT (FIG. 22C) ESNFs, after 7 days of incubation.

Figure 23:
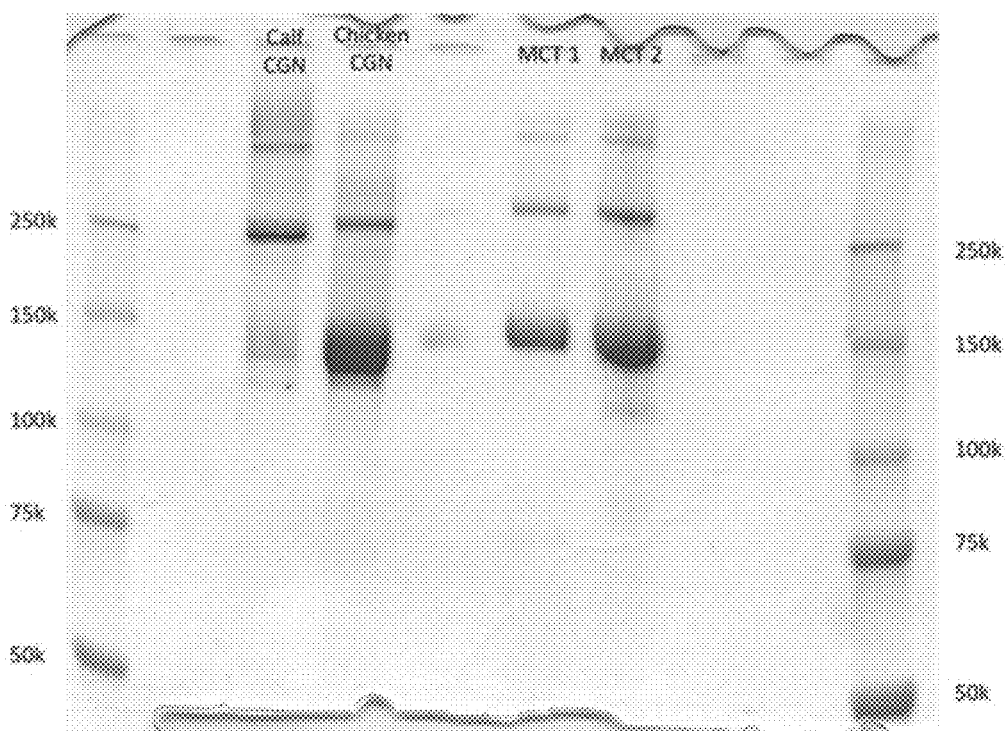

FIG. 23 depicts gel electrophoresis analysis (SDS-PAGE) showing the major protein bands for MCT compared to collagen samples extracted from calf and chicken.

Figure 24:
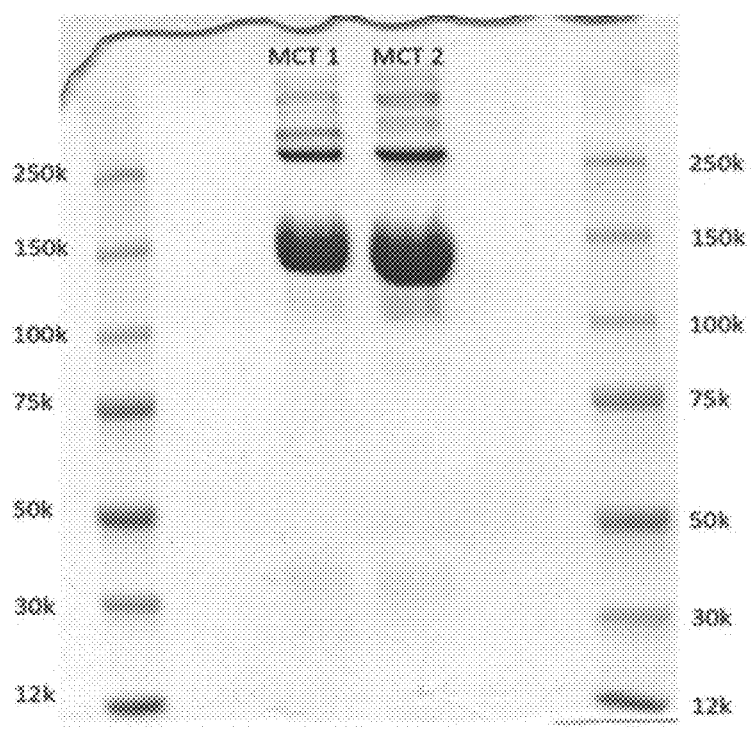

FIG. 24 depicts gel electrophoresis analysis (SDS-PAGE) showing the efficacy of the MCT isolation process from sea cucumber, as shown by the consistency in the protein bands for MCT from batch to batch.

Figure 25A:
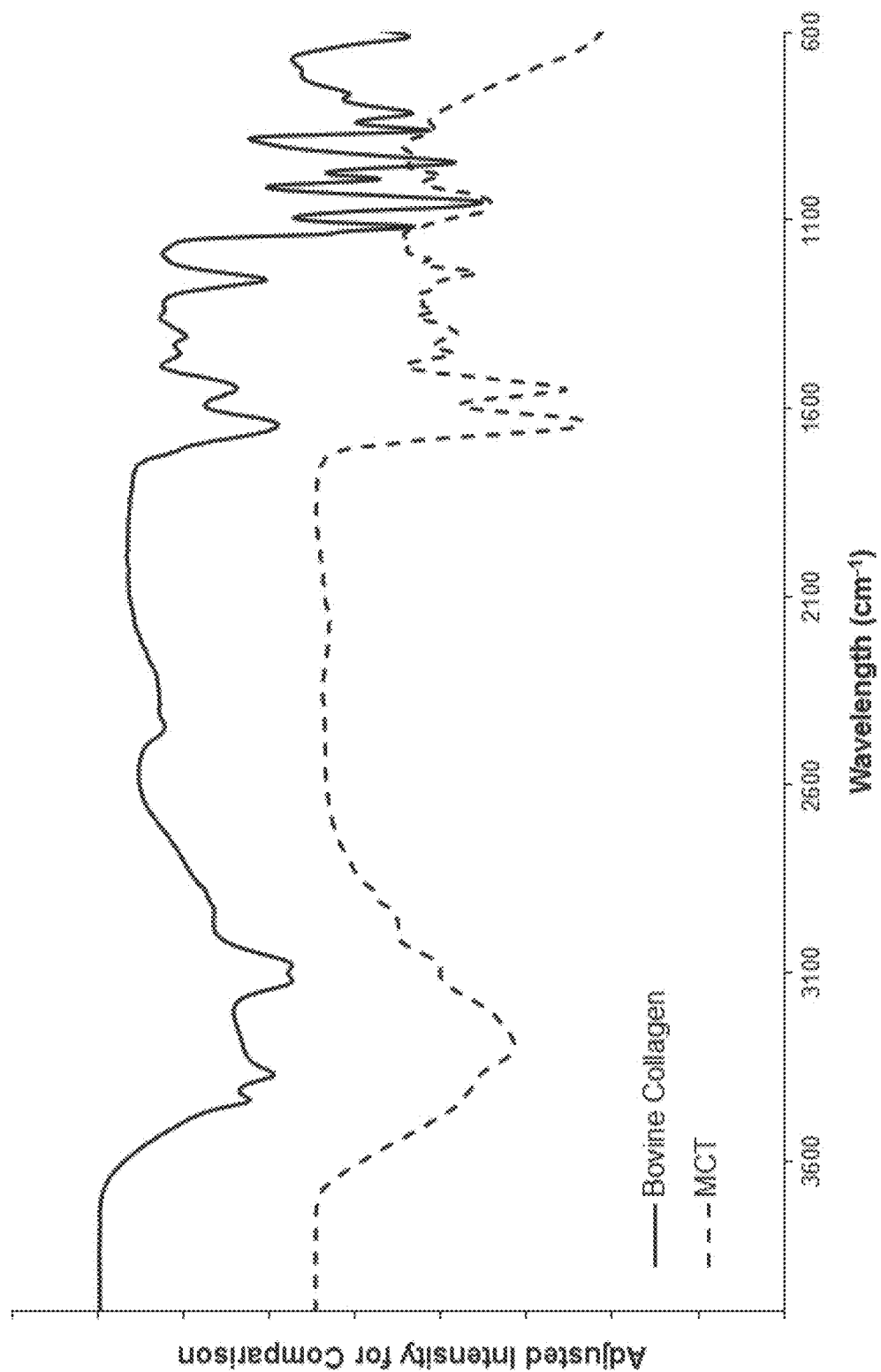
Figure 25B:
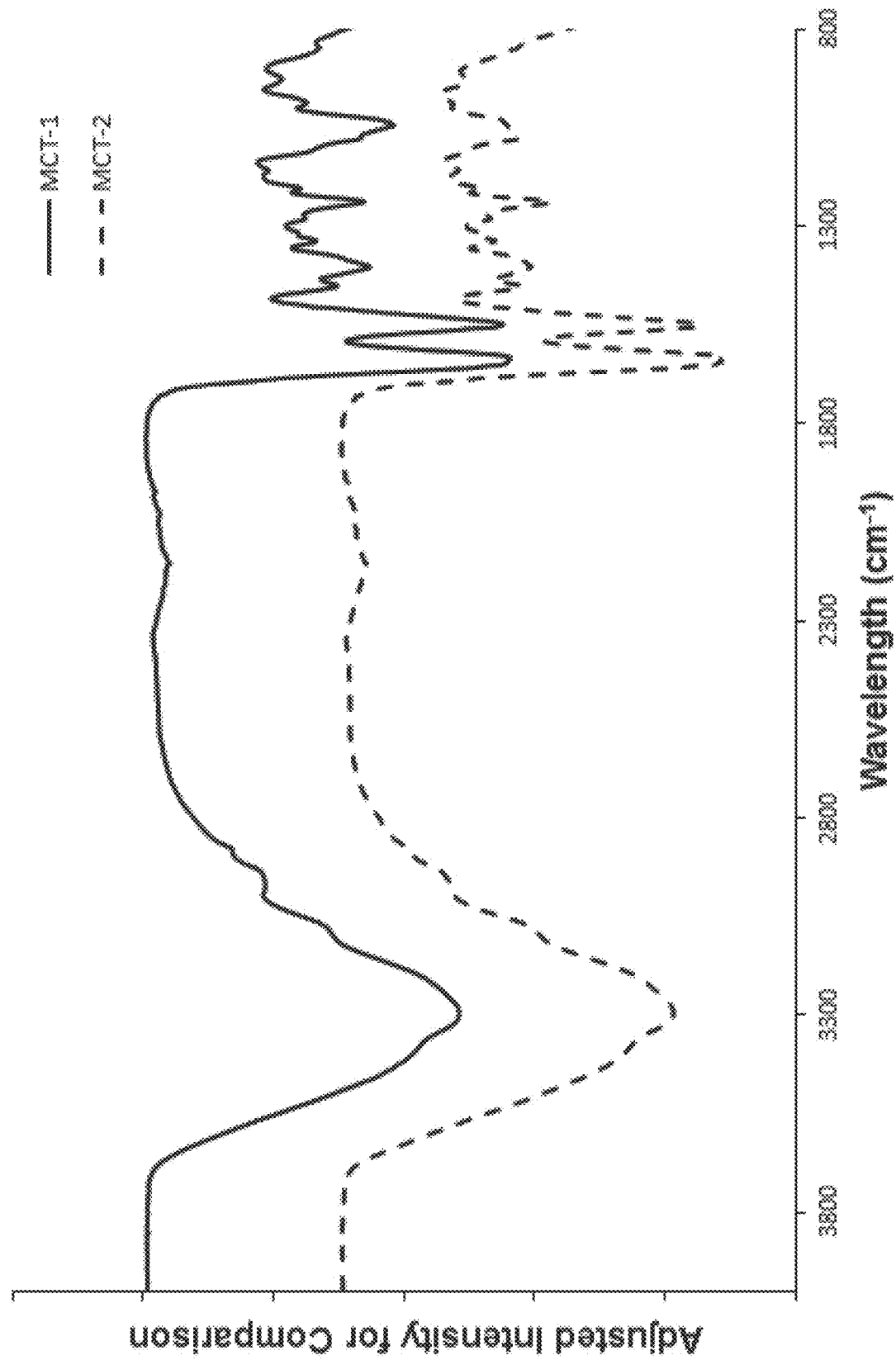

FIG. 25A depicts FTIR-Infrared spectra for MCT collagen compared to calf collagen, showing the chemical structural differences among both samples, and FIG. 25B depicts comparative FTIR spectra showing the efficacy of MCT isolation process from sea cucumber, as shown by the consistency in the FTIR chemical profile for MCT from batch to batch.

Figure 26:
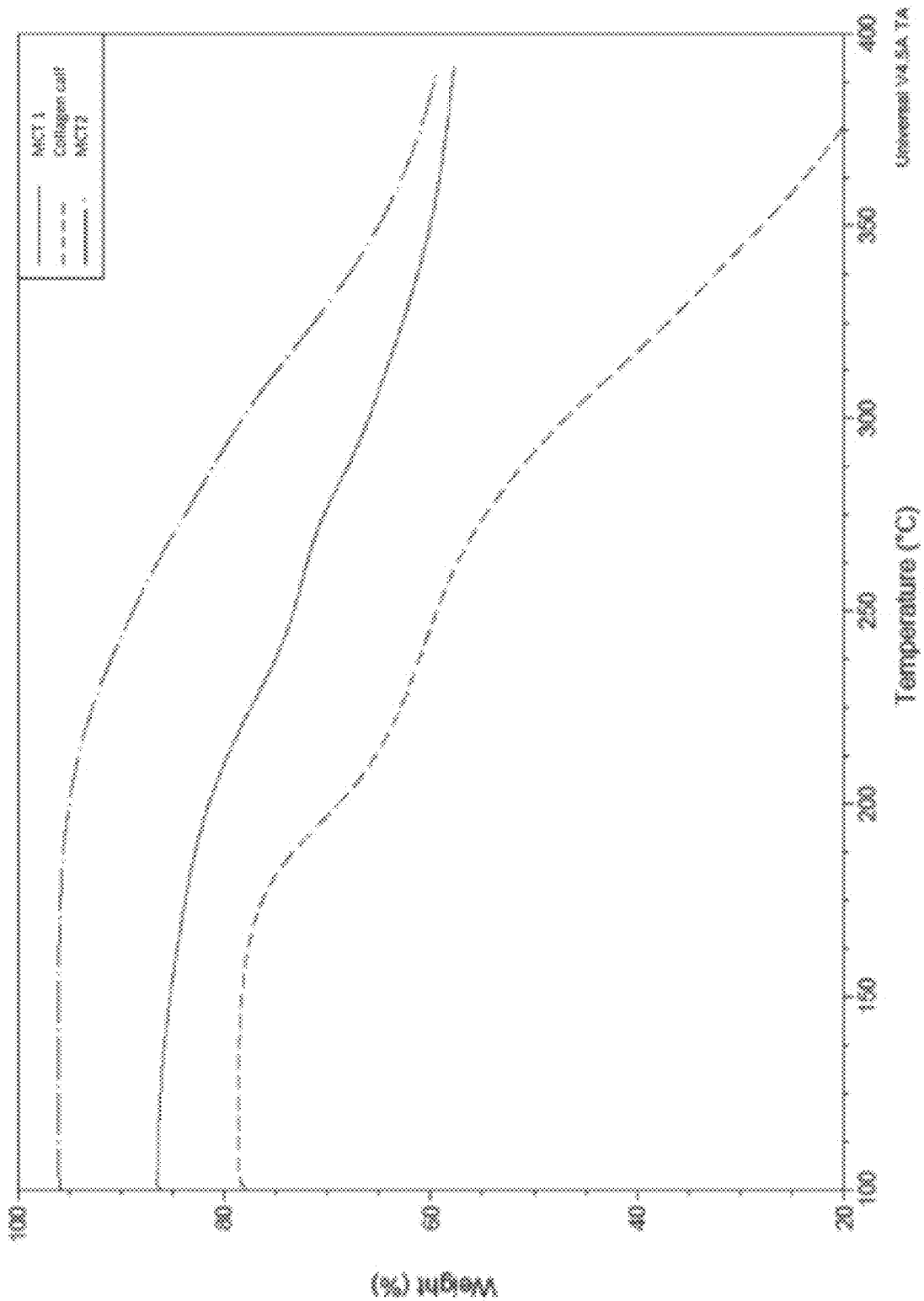

FIG. 26 depicts themogravimetric analysis (TGA) of collagen samples showing the differences in thermal behavior for MCT and calf collagen samples.

Figure 27:
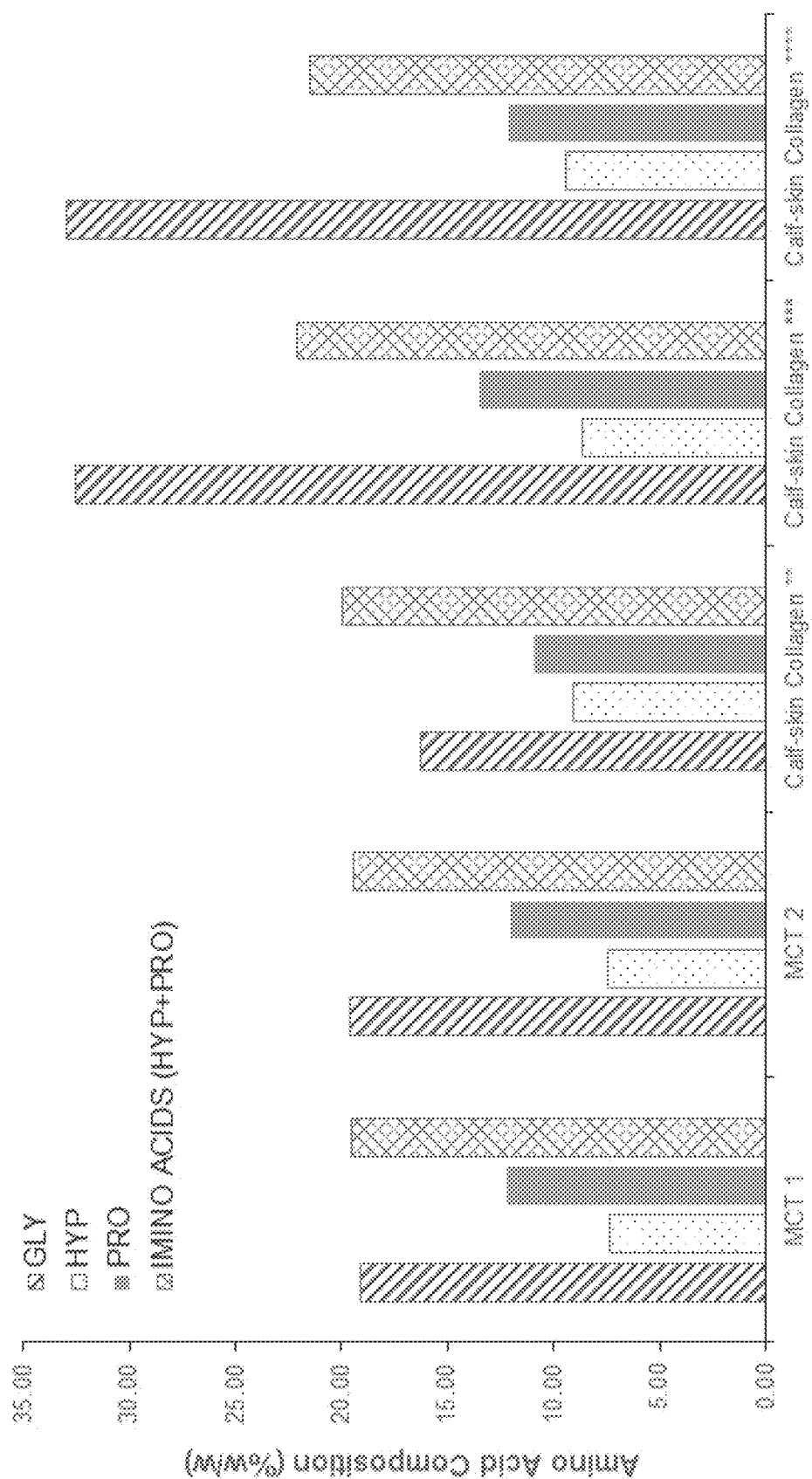

FIG. 27 shows a distribution of collagen structural amino acid composition found in mutable collagenous tissue extracted from sea cucumber and compared to bovine collagen isolated from calf-skin.

Figure 28A:
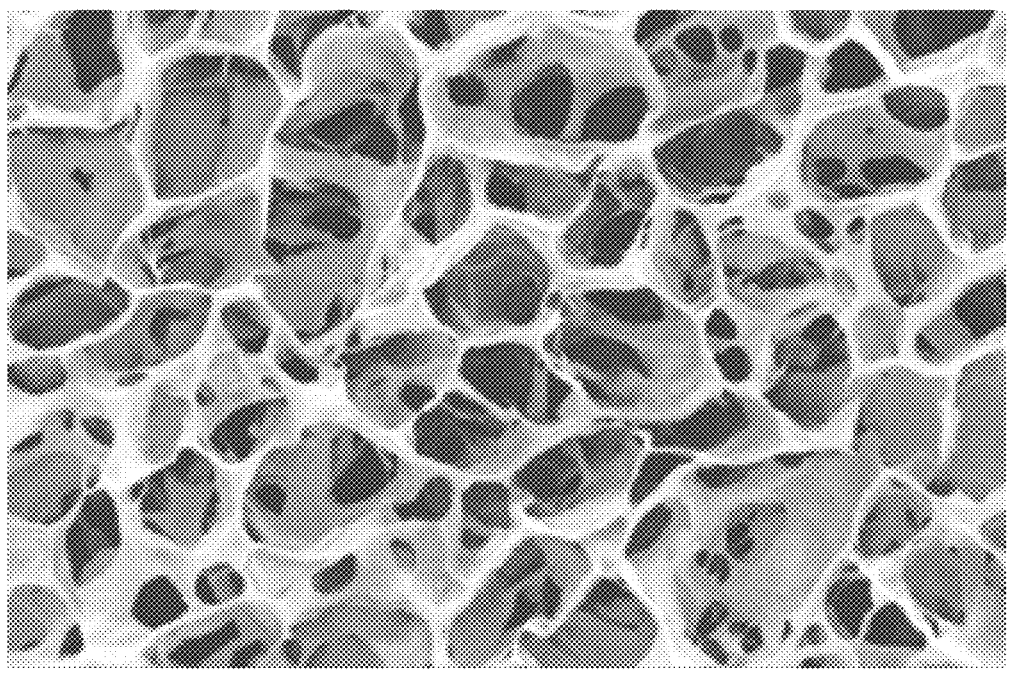
Figure 28B:
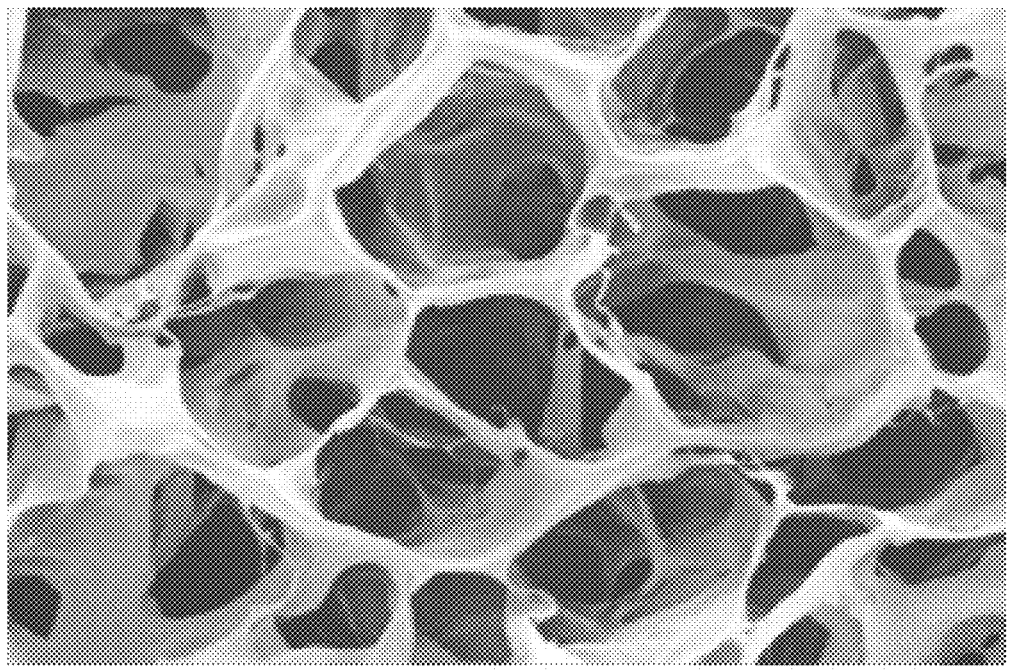

FIGS. 28A and 28B are scanning electron microscopy (SEM) images showing the morphology and porosity of MCT-chitosan dressing template (3D-sponge) fabricated by a solvent casting technique.

Figure 29A:
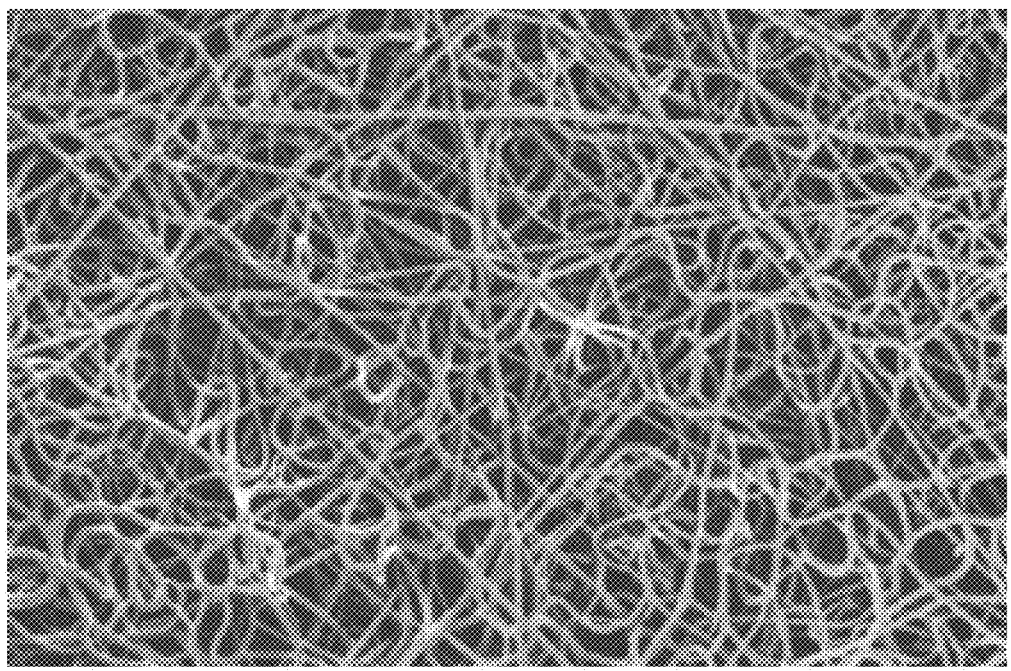
Figure 29B:
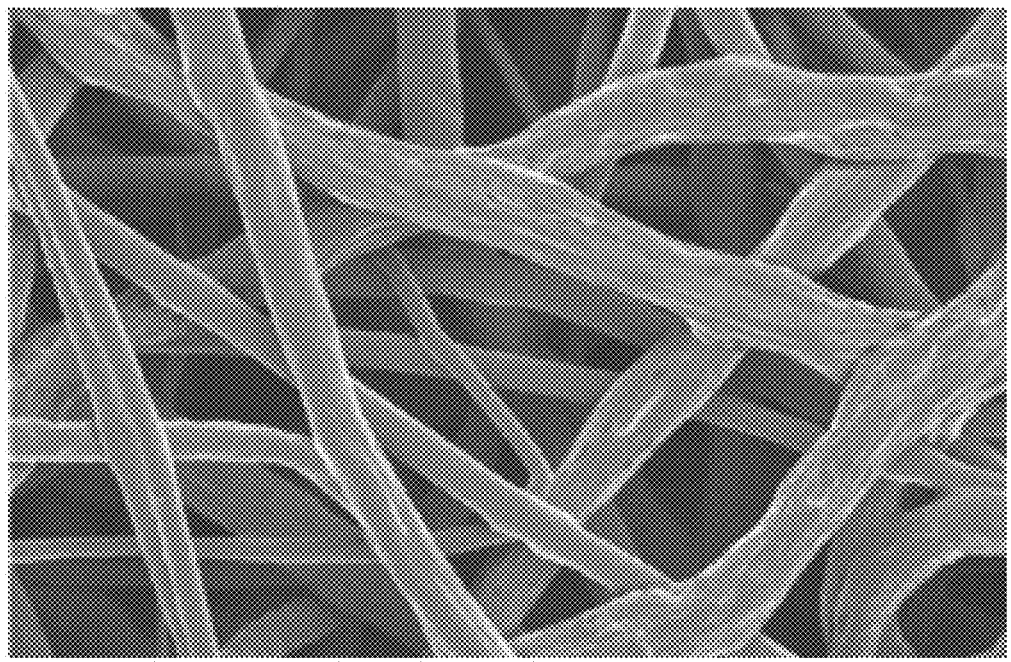

FIGS. 29A and 29B are scanning electron microscopy (SEM) images showing the surface morphology and structure of MCT-chitosan nanofiber dressing template fabricated by an electrospinning technique.

Figure 30A:
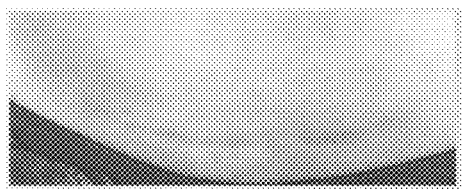
Figure 30B:
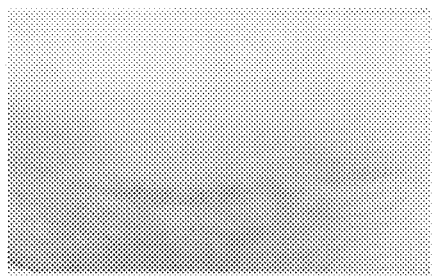

FIGS. 30A and 30B are before and after pictures showing effects of administration of scar cream according to an embodiment.

Figure 31A:
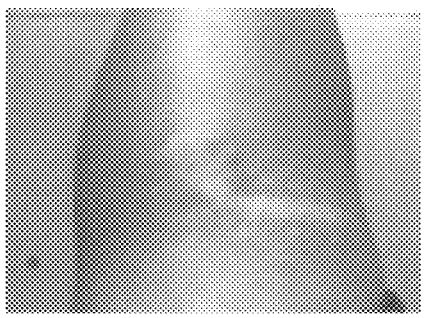
Figure 31B:
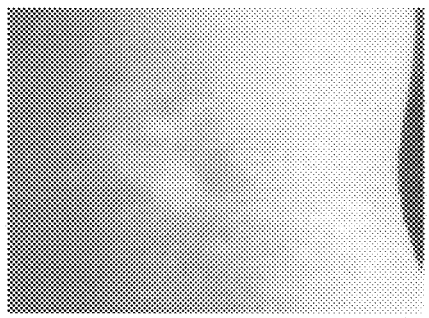

FIGS. 31A and 31B are additional before and after pictures showing effects of administration of scar cream according to an embodiment.

Figure 32A:
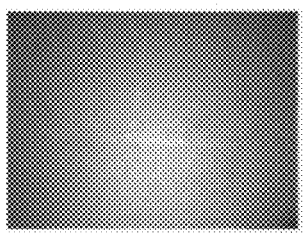
Figure 32B:
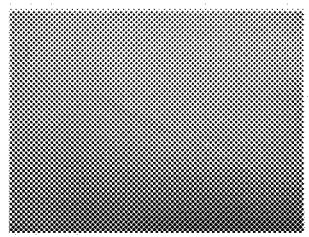
Figure 32C:
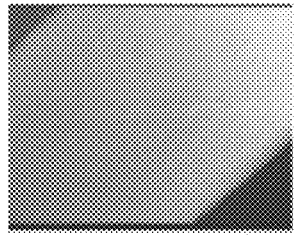

FIGS. 32A-32C are still further before and after pictures showing effects of administration of scar cream according to an embodiment.

Figure 33A:
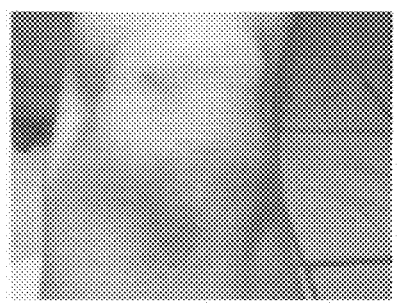
Figure 33B:
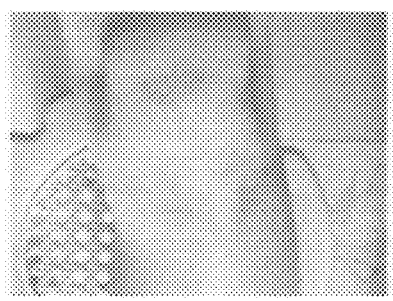

FIGS. 33A and 33B are still further before and after pictures showing effects of administration of scar cream according to an embodiment.

FIGS. 34A-34D are still further before and after pictures showing effects of administration of scar cream according to an embodiment FIGS. 35A-35C depict MCT-CHT matrix structure.

Figure 36:
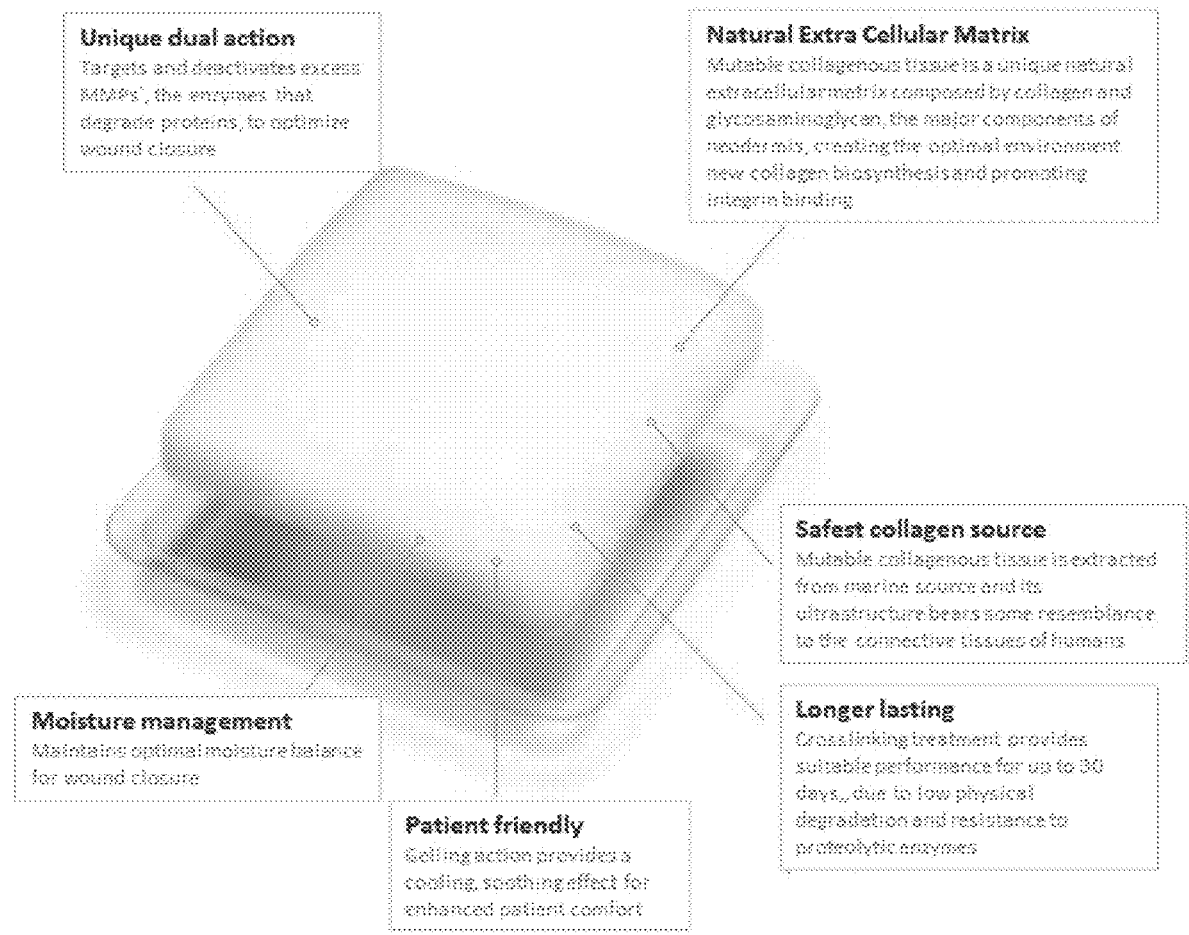

FIG. 36 depicts a wound sponge and its characteristics and features according to an embodiment.

Figure 37:
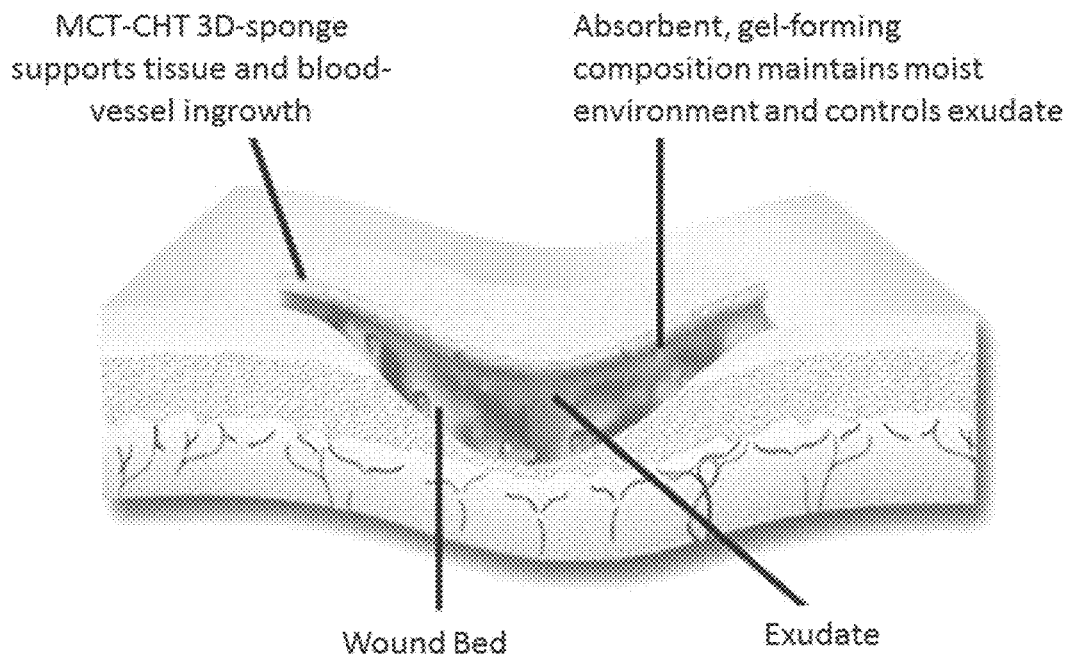

FIG. 37 depicts function of a 3D sponge according to an embodiment.

Figure 38:
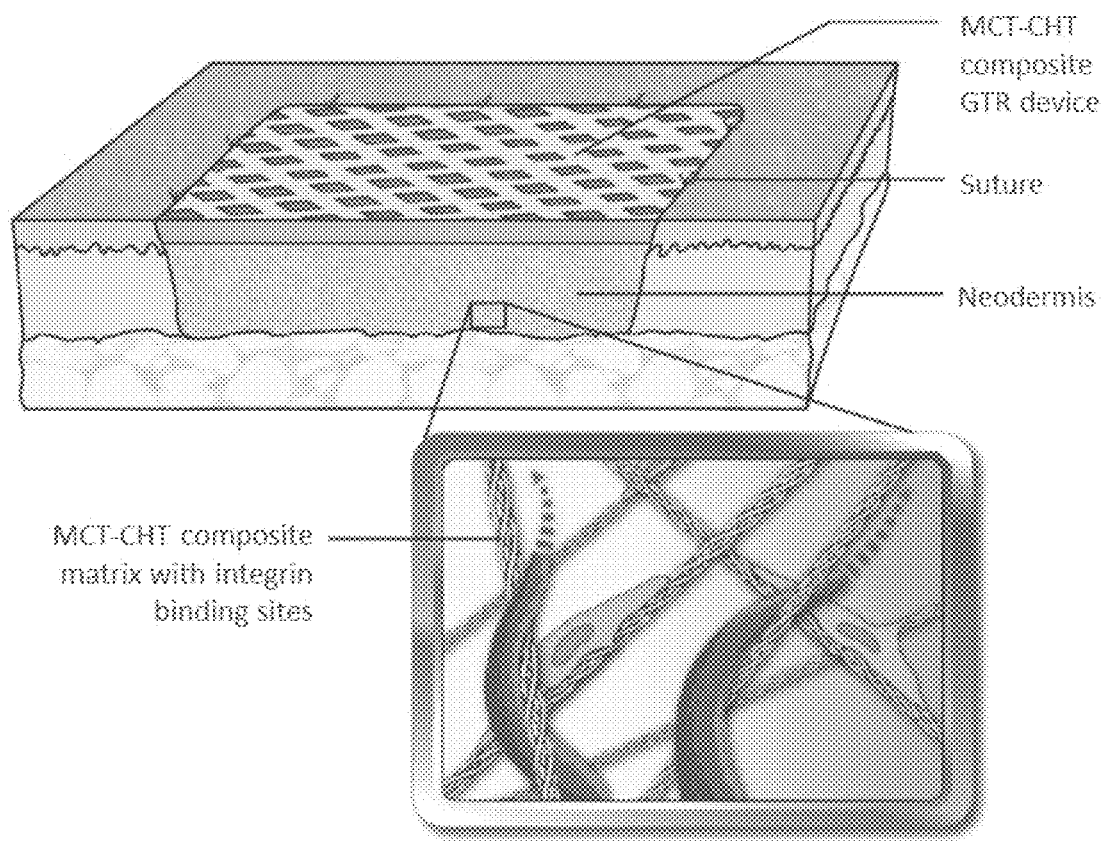

FIG. 38 depicts function of a device according to an embodiment.

DETAILED DESCRIPTION

In accordance with aspects of the invention, the present application describes new biodegradable, biocompatible composite materials comprising a combination of mutable collagenous tissue (MCT) and chitosan. The MCT and MCT-chitosan composites are extremely versatile, and can be formulated into various kinds of biomaterials, such as dermal patches, three-dimensional sponges, biodegradable sutures, and sponges for cell proliferation in tissue engineering, as well as hydrogels and biofilms for tissue regeneration.

Additionally, the MCT and MCT-chitosan composite material can also be formulated as a biofilm of a 3D-sponge with improved water absorption, thermal stability, vapor permeation and cell attachment. In such embodiments, the biofilms and/or 3D-sponges will be suitable as sponges for guided tissue regeneration in tissue engineering, and wound dressing templates for surgical and medical applications.

Definitions: As used herein, certain terms have the following meanings. All other terms and phrases used in this specification have their plain and ordinary meanings as one of ordinary skill in the art would understand. Such plain and ordinary meanings may be obtained by reference to technical dictionaries, such as Hawley's *Condensed Chemical Dictionary* 14$^{th}$ Edition, by R. J. Lewis, John Wiley & Sons, New York, N.Y., 2001.

References in the specification to "one embodiment", "an embodiment", "an example embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one ordinarily skilled in the art to affect such aspect, feature, structure, moiety, or characteristic in connection with other embodiments, whether or not explicitly described.

The term "and/or" means any one of the items, any combination of the items, or all of the items with which this term is associated.

The singular forms "a," "an," and "the" include a plural reference unless the context clearly dictates otherwise. Thus, for example, a reference to "a compound" includes a plurality of such compounds, so that a compound X includes a plurality of compounds X.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer. Unless indicated otherwise herein, the term "about" is intended to include values, e.g., weight percentage, proximate to the recited range that are equivalent in terms of the functionality of the individual ingredient, the composition, or the embodiment. In addition, a recited range (e.g., weight percentage, carbon groups, and the like) includes each specific value, integer, decimal, or identity within the range. Specific values listed herein for ranges and the like are for illustration only; they do not exclude other well-defined values or other values within defined ranges.

The phrase "one or more" is readily understood by one of ordinary skill in the art, particularly when read in context of its usage. For example, one or more substituents on a phenyl ring refers to one to five, or one to up to four, for example if the phenyl ring is disubstituted.

The term "contacting" refers to the act of touching, making contact, or of bringing to immediate or close proximity, including at the molecular level, for example, to bring about a chemical reaction or physical change, e.g., in a solution or other reaction mixture.

An "effective amount" generally means an amount which provides the desired effect. An effective amount therefore means a dosage sufficient to enhance the efficacy of treatment for a disease state or condition being treated. Thus, the effective amount can vary depending on the patient, the disease, and the treatment being affected.

The term "patient" or "subject" refers to any animal, such as a mammal, including mice, rats, other rodents, rabbits, dogs, cats, swine, cattle, sheep, horses, primates, and humans.

In reference to MCT, the phrase "substantially comprising collagen" means that the MCT comprises at least fibrillar collagen. For example, a MCT fibrillar collagen can comprise type I, II, III, V and/or XI collagen. In one aspect, MCT fibrillar collagen will be characterized as type-I. Other compounds that can be specifically included or excluded from the composites described herein include fibrillar collagen type II, III, V and/or XI, or combinations thereof. The term "glycosaminoglycan" refers to molecules comprising long unbranched polysaccharides containing a repeating disaccharide unit, including, for example, chondroitin sulfate, hyaluronic acid, heparin, keratan sulfate, heparan sulfate and/or dermatan sulfate.

Figure 1A:
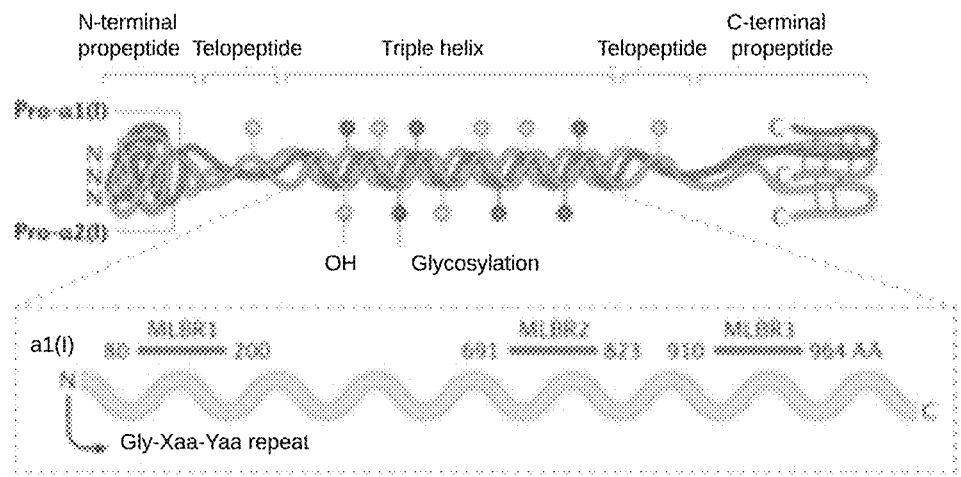
Figure 1B:
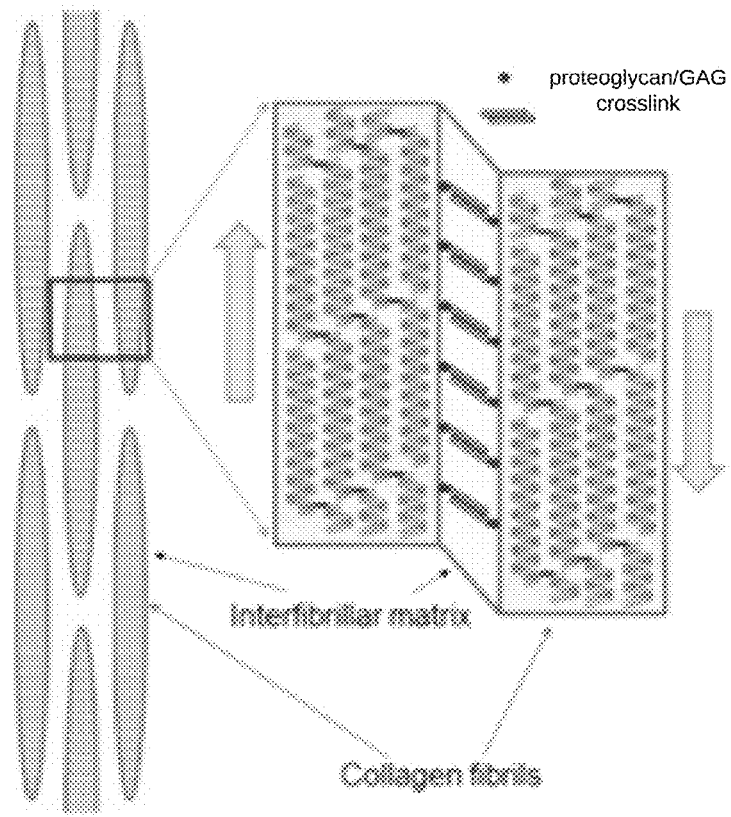

Mutable collagenous tissue (MCT): Echinoderms are marine invertebrates widespread in all the oceans and employed as source of food for decades (e.g. sea cucumbers and sea urchins). They are well-known also for their peculiar connective tissues, called mutable collagenous tissue (MCT), which are able to rapidly change their passive mechanical properties (stiffness and viscosity), under nervous system control. MCTs are a unique feature of echinoderms and have been described in all the five extant classes (I. C. Wilkie, "Mutable collagenous tissue: overview and perspectives," V. Matranga (Ed.), Echinodermata. Progress in Molecular and Subcellular Biology. Marine Molecular Biotechnology, vol. 5, Springer, Berlin (2005), pp. 221-250. Mutable collagenous structures consist of discontinuous collagen fibrils organized into bundles (fibers) by an elastomeric network of fibrillin microfibrils and interconnected by a stress-transfer matrix consisting of glycosaminoglycan that binds to and aggregates the fibril. This type of tissue has been recently proposed as a possible source of inspiration for "smart dynamic biomaterials" for tissue engineering and regenerative medicine applications (A. Barbaglio, S. Tricarico, C. Di Benedetto, D. Fassini, A. P. Lima, A. R. Ribeiro, C. C. Ribeiro, M. Sugni, F. Bonasoro, I. C. Wilkie, M. Barbosa, M. D. Candia Carnevali, "The smart connective tissue of echinoderms: a materializing promise for biotech applications," Cah. Biol. Mar., 54 (2013), pp. 713-720; C. Di Benedetto, A. Barbaglio, T. Martinello, V. Alongi, D. Fassini, E. Cullorà, M. Patruno, F. Bonasoro, M. A. Barbosa, M. D. Candia Carnevali, M. Sugni, "Production, characterization and biocompatibility of marine collagen matrices from an alternative and sustainable source: the sea urchin *Paracentrotus lividus*," Mar. Drugs, 12 (2014), pp. 4912-4933. Particularly, the sea cucumber membrane (a well-known MCT) can provide a sustainable and biocompatible source of native fibrillar collagen to produce thin membranes for regenerative medicine applications. FIG. 1 shows general collagen structure, in this case for bovine collagen, on the left, and general structure for MCT on the right. In the case of MCT, the right hand side of FIG. 1 shows an exploded view of a portion of the structure, with a proteoglycan-CAG crosslink between interfibrillar matrices, and between collagen fibrils.

Among the "blue biomaterials," marine invertebrate collagen presents itself as a valid replacement the most commonly used mammal-derived collagen (for example, bovine collagen, depicted on the left side of FIG. 1). Mammal-derived collagen is routinely employed in a wide range of human applications, from large-scale uses, such as food, pharmaceutical/nutraceutical industry and cosmetics, to more targeted fields, such as cell cultures and biomedical/clinical applications. However, because of allergy problems, religious and social/life style constraints, disease transmission-connected reasons (e.g. bovine spongiform encephalopathy), and high costs of recombinant technologies, collagen sources alternative to mammals are constantly investigated (T. H. Silva, J. Moreira-Silva, A. L. P. Marques, A. Domingues, Y. Bayon, R. L. Reis, "Marine origin collagens and its potential applications," Mar. Drugs, 12 (2014), pp. 5881-5901.

Figure 2:
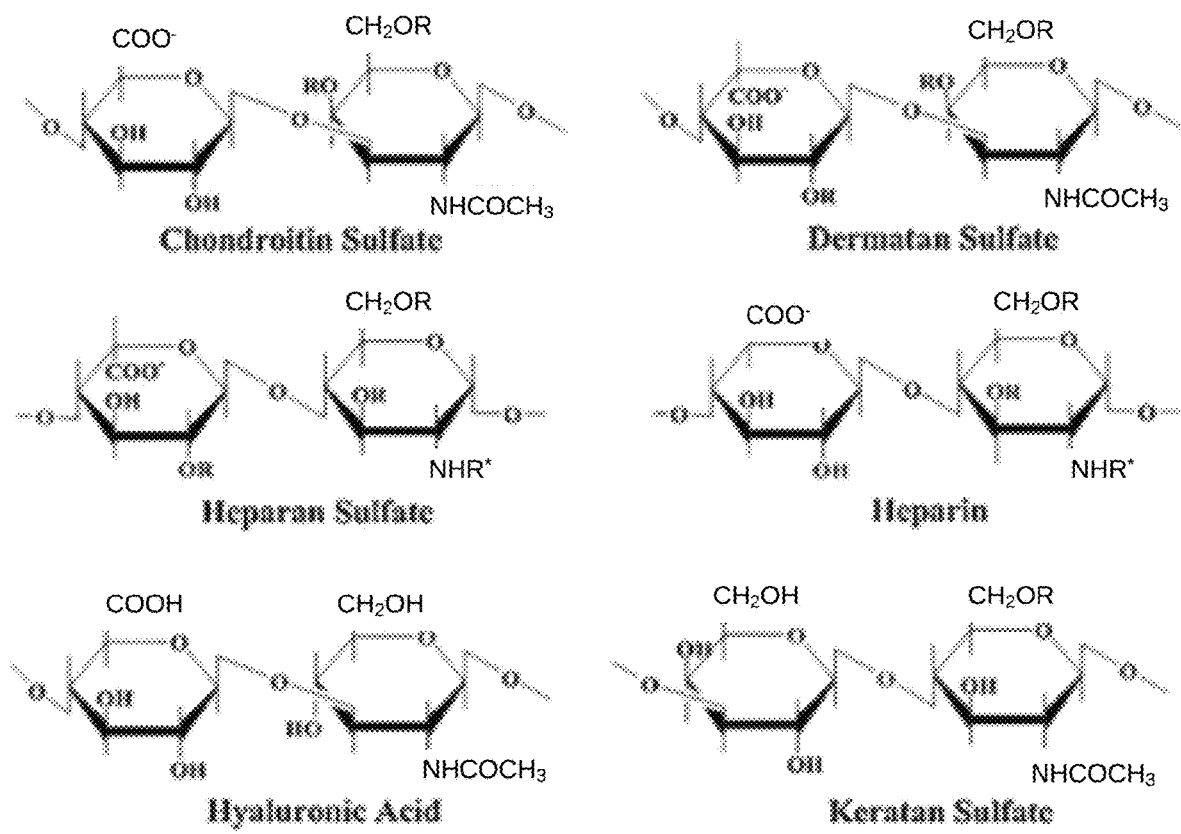

Glycosaminoglycans, the general structure of which is shown in FIG. 2 below, are long unbranched polysaccharides consisting of a repeating disaccharide unit. The repeating unit consists of an amino sugar (N-acetylglucosamine or N-acetylgalactosamine) along with an uronic sugar (glucuronic acid or iduronic acid) or galactose. Glycosaminoglycans are highly polar and attract water. They are therefore useful to the body as a lubricant or as a shock absorber, being located primarily on the surface of cells or in the extracellular matrix (ECM).

Figure 3B:
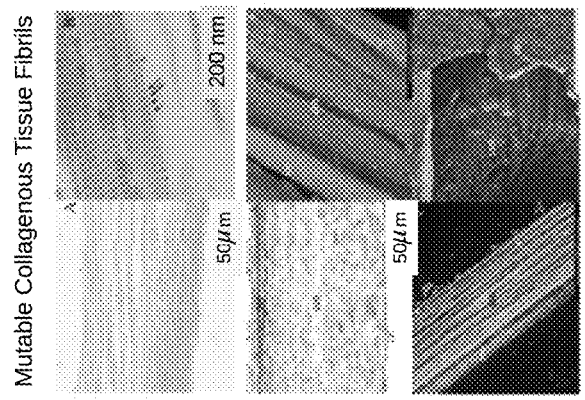
Figure 3A:
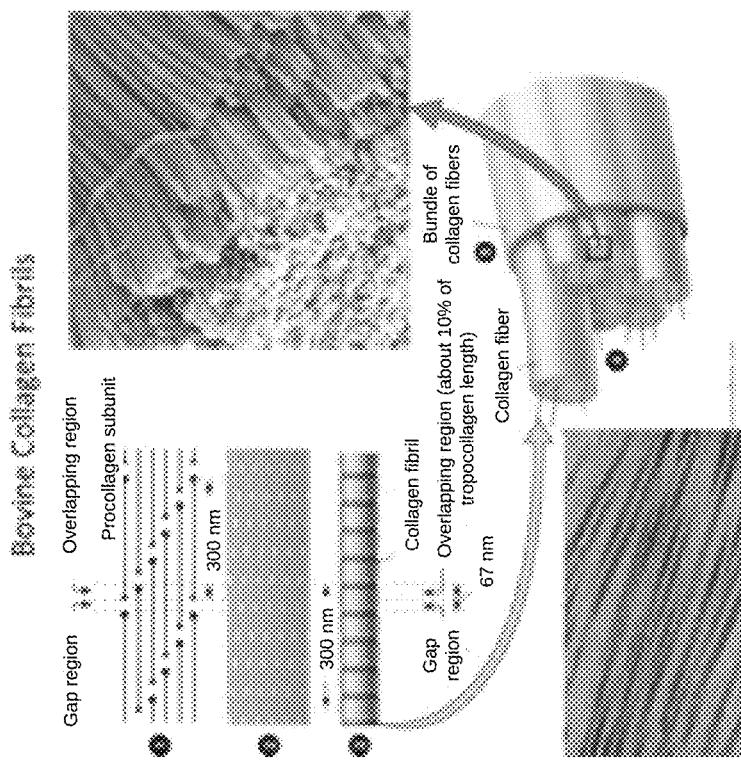

A further advantage of echinoderm MCTs is the relative ease of obtaining a high amount of native collagen fibrils, which maintain their original structure (Di Benedetto et al., 2014, cited above). Indeed, most mammalian collagen is usually employed in its hydrolyzed (acid-solubilized) form, a characteristic that strongly reduces the mechanical performance of the produced membrane/sponge and that can be a limit in those biomedical applications where highly resistant materials, with fibril three-dimensional organization, are required (e.g. tendon/ligament regeneration or dermis re-construction). Echinoderm MCTs can be useful to easily and rapidly produce fibrillar collagen membranes with a high similarity in terms of both ultrastructural and mechanical characteristics to the physiological situation of connective tissue. FIGS. 3A and 3B show the comparative morphology of the collagen fibril structure for bovine collagen (FIG. 3A) and MCT (FIG. 3B). MCT fibrils are internally crosslinked by GAG (glucosaminoglycan), thus providing more stability to the macromolecular structure of collagen and reducing its biodegradability, an important aspect for wound healing, and an attribute that bovine collagen lacks. FIGS. 35A-35C depict crosslinking of the fibrils employing GAG. FIG. 35A shows the macroscopic arrangement of the collagen fibrils, and illustrates that the aligned fibrillar structures are kept together by intrafibrillar crosslinking networks driven by interactions between Glycosaminoglycan (GAG) and collagen's core protein. FIG. 35B shows the intrafibrillar crosslinking networks in more detail. FIG. 35C depicts multidirectional stability of a strongly organized mesh, resulting in improved mechanical performance and biodegradation properties in vivo.

A specific regenerative medicine field where MCT fibrillar collagen is suitable for commercial applications is guided tissue regeneration (GTR). One of the aims of GTR is to reduce post-surgical tissue adhesions, a common and only partially solved complication, which prevents proper tissue regeneration. Adhesions are abnormal attachments or mixtures of cells forming between tissues or organs after surgery or due to local inflammation. Only recently have researchers tried to produce effective and satisfactory tools to overcome them. Indeed, barrier-membranes comprising several different biomaterials (e.g. chitosan and hyaluronic acid) have been tested for GTR, but none of them displayed all the necessary functional properties, the most important of which is avoiding cell penetration into the underlying anatomical compartment (S. Tang, W. Yang, X. Mao, "Agarose/collagen composite scaffold as an anti-adhesive sheet," Biomed. Mater., 2 (2007), pp. S129-S134. Echinoderm MCT-based membranes have porosity and three-dimensional structure which can be modified as desired.

Figure 4:
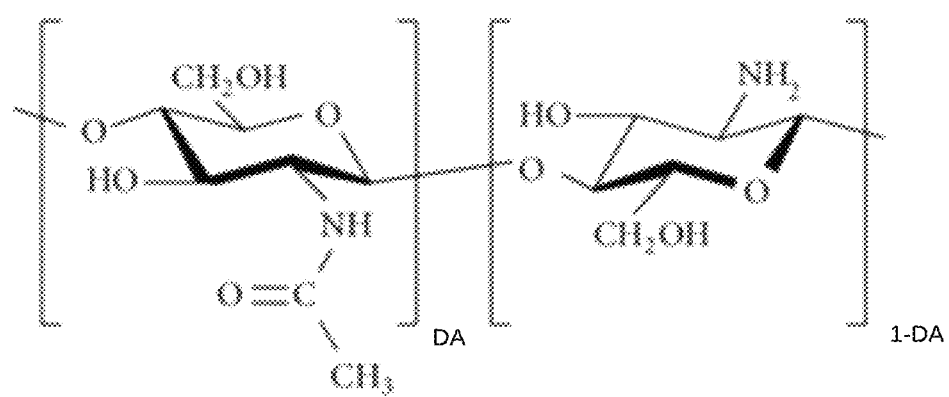

Chitosan: Chitin is a biopolymer composed of poly N-acetyl glucosamine. Chitin is the second most abundant biopolymer on earth, after only cellulose. It is commonly found in the exoskeleton or cuticles of many invertebrates, such as the shells of marine arthropods, and in the cell wall of most fungi and some algae. Chitin is generally insoluble in water, but can be deacetylated by treatment with a caustic, such as sodium hydroxide, to form the soluble cationic polysaccharide, chitosan. The chemical name of chitosan is poly($\beta$-(1→4)-2-amino-2-deoxy-D-glucopyranose). FIG. 4 shows the general chemical structure of chitosan.

Chitosan-based bandages and surgical dressings produced by HemCon Medical Technologies were recently approved by the U.S. FDA for use as hemostatic bandages with proven antibacterial properties against a wide range of harmful organisms, including MRSA and *Acinetobacter baumannii*. The bandages and dressings can be used to rapidly stop bleeding, including extensive arterial bleeding. Both the blood clotting and the antibacterial properties of the materials can be attributed to chitosan (see U.S. Pat. No. 7,482,503 (Gregory et al.), which is incorporated herein by reference). The MCT-chitosan composite material can be used in place of the chitosan in the compositions described therein, while useful characteristics of chitosan, such as mucoadhesivity, biocompatibility, and biodegradability can still be maintained.

Chitosan is commercially available from many chemical suppliers, such as Sigma Aldrich Co., St. Louis, Mo. Chitosan is offered in various grades, average molecular weights, and degrees of deacetylation.

In some embodiments, the chitosan can be a "high molecular weight" chitosan. High molecular weight chitosan refers to chitosan that has a number average molecular weight of at least about 100 kDa, and typically about 170 kDa to about 400 kDa. In some embodiments, high molecular weight chitosan can have a molecular weight of at least about 100 kDa, at least about 110 kDa, at least about 150 kDa, or at least about 200 kDa. In other embodiments, high molecular weight chitosan can have a molecular weight of about 100 kDa to about 400 kDa, about 120 kDa to about 400 kDa, about 150 kDa to about 400 kDa, about 170 kDa to about 400 kDa, 100 kDa to about 300 kDa, about 120 kDa to about 300 kDa, about 150 kDa to about 300 kDa, about 170 kDa to about 300 kDa. The value of "DA" in FIG. 4 can be any number or range that results in approximately the values for the N-Acetyl-D-glucosamine content of chitosan described herein. As would be readily recognized by one of ordinary skill in the art, chitosan as illustrated in FIG. 4 may also be partially acetylated.

Other embodiments may include low molecular weight chitosan. Low molecular weight chitosan refers to chitosan molecules with less than 100 monomeric units (less than about 18 kDa or less than about 20 kDa). Molecular weights of chitosan can be determined, for example, by gel permeation chromatography and capillary viscosity.

The chitosan can have a degree of deacetylation that is typically at least about 60%, at least about 75%, at least about 80%, at least about 85%, at least about 90%, at least about 95%, or at least about 99%. Alternatively, the chitosan can be fully deacetylated.

MCT-Chitosan Composite Materials:

Chitosan binds to structural components in MCT by electrostatic interactions, driven by its positively charged amino groups, allowing formation of strong hydrogen bonding and dipole-dipole interactions, due to both MCT and chitosan high molecular weights and charge density. These interactions enable development of stable biomaterials, such as hydrogels, biofilms, 3D-sponges, and nanofibers. MCT-chitosan composite materials can be used in GTR to prepare dermal patches, cosmeceuticals, and dressings for wound healing applications. MCT-chitosan composite materials can also be used as hydrogels or sponge-like materials or scaffolds for skin and cartilage tissue cultures, as matrices for tissue engineering, and as biocompatible coatings for biomedical devices.

MCT and MCT-chitosan composite materials provide higher biocompatibility, improved mechanical performance, and superior biodegradability relative to known synthetic and animal collagen-based devices. In addition to direct biological effects from the MCT-chitosan composites (anti-microbial, antifungal and wound healing properties), the biomaterials can be used for targeting or controlled release systems to encapsulate therapeutic agents for oral, dermal, or respiratory delivery.

Nanoparticles and biofilms can be prepared from MCT and chitosan, as described herein. MCT comprising collagen is particularly useful for preparing nanoparticles. Since MCT mainly comprises fibrillar collagen, MCT is well suited for preparing MCT-chitosan composite hydrogels, biofilms, 3D-sponges and nanofibers, providing composite biomaterials with superior mechanical performance compared to known animal collagen-based biomaterials.

The MCT and MCT-chitosan composite biomaterials can be crosslinked during preparation by means of chemical treatment by reaction with biological compatible crosslinking agents (glutaraldehyde, ECC/NHS) or by thermal treatment under vacuum pressure. Swelling of a composite polymeric matrix can produce faster degradation and reduction of mechanical properties. Crosslinking reduces or prevents spontaneous swelling of the composite biomaterials, increasing mechanical performance and handling.

In some embodiments, the MCT and MCT-chitosan composite material can include or exclude polymers other than chitosan or MCT. For example, some embodiments include dextran, alginate, and/or cellulose-derived materials such as hydroxyethylcellulose; other embodiments exclude some or all of these. Some embodiments include synthetic polymers such as polyvinyl alcohol, polycaprolactone or polyethylene oxide, while other embodiments exclude some or all of them.

Analysis of MCT, Chitosan, and Combination Products:

A variety of methods can be used to analyze and evaluate MCT, chitosan, and their composite products. These techniques include mass spectrometry, mechanical properties (tensile strength) and swelling properties, scanning electron microscopy (SEM) and atomic force microscopy (AFM) to characterize surface morphology, differential scanning calorimetry (DSC) for thermal characterization of the composite biomaterial. Tensile strength and swelling properties of the composite biomaterials were characterized in ASTM measurements.

Analysis of the MCT and MCT-chitosan composites described herein indicates that the composite materials have improved stability, higher drug loading capacity, improved drug release properties, improved cell uptake, greater porosity, improved tensile strength and thermal stability compared to compositions that include only chitosan. The materials also are non-cytotoxic in vitro.

Wound Healing:

MCT and MCT-chitosan composite biomaterials also have valuable properties for wound healing applications because they exhibit enhanced bacteriostatic activity with respect to pure chitosan, improved biocompatibility and enhanced mechanical properties. The MCT-chitosan composites exhibit an increase in chitosan antimicrobial activity. The composites bind to the negatively charged bacterial surface to disturb the cell membrane. These properties can be applied for use in GTR applications by formulation of injectable hydrogels, dermal patches, and wound dressing templates, for example, to promote ulcer and burn healing. The MCT-chitosan composites also can be used as hemostatic agents in wound and surgical dressings.

The MCT and MCT-chitosan composite biomaterials can be used in a variety of other biomedical applications. As a result of the biocompatible properties, such as good blood compatibility, potentiated mechanical performance, and cell growth efficiency, MCT-chitosan composites can be used in surgical applications and regenerative medicine. The permeability of MCT-chitosan composite membranes can be controlled through plasma-treatment. Consequently, such composite membranes can be used in dialysis.

The above-mentioned U.S. Pat. No. 7,482,503 (Gregory et al.) describes methods for the preparation of wound dressings. Wound dressings can be prepared according to such methods using the MCT and MCT-chitosan composite materials described herein in place of the chitosan biomaterial that Gregory et al. describe. Additionally, the MCT-chitosan composites can be used as coatings for medical devices, such as stents, catheters, and prosthetics, to prevent detrimental biofilm formation or bacteremia in patients and also to promote bio-mimetization and osteo-integration. MCT complexation to chitosan promotes a surface modification on collagen fibrils that increases the porosity of its 3D-sponge scaffolds, as shown by SEM micrographs. MCT have also been found to improve the physical properties of chitosan scaffolds, such as tensile strength, swelling degree, and thermal stability, as shown by mechanical analysis and DSC calorimetry.

Tissue Engineering:

Tissue engineering (TE) research is based on the seeding of cells onto porous biodegradable polymer matrixes. A primary factor for successful seeding is the availability of good biomaterials to serve as a temporary matrix or scaffold for cells to proliferate and differentiate. Recently, chitosan and its derivatives have been reported as attractive candidates for sponge-like materials because they degrade as the new tissues are formed, eventually without inflammatory reactions or toxic degradation. In TE applications, the cationic nature of chitosan is primarily responsible for electrostatic interactions with anionic glycosaminoglycans, proteoglycans, and other negatively charged molecules.

MCT complexation to chitosan promotes a surface modification on chitosan films that increases the porosity of its 3D-sponge sponges, as shown by SEM micrographs. MCT have also been found to improve the physical properties of chitosan biofilms, such as tensile strength, swelling degree, and thermal stability, as shown by mechanical analysis and DSC calorimetry. The MCT and MCT-chitosan composite biomaterials can be used to control the morphology and function of cells, and therefore can be used as a tissue engineering scaffold or matrix in wound healing applications for GTR. The MCT and MCT-chitosan composite biomaterials can also be chemically modified for TE applications. For example, the composites can be modified by grafting particular sugars to MCT backbone. Certain cells can distinctively recognize the specific sugars, thus providing the specific recognition to antigen presenting cells such as B-cells, dendritic cells, and macrophages.

Cosmeceutical Formulations:

The invention also provides formulations that include MCT and MCT-chitosan composites described herein for use as therapeutic cosmetics (cosmeceuticals). MCT and MCT-chitosan composites, in powder or solution form, can be added to basic cosmetic formulations to form pharmaceutical, and/or functional cosmetics products. These cosmeceutical compositions can be formulated with a dermatologically and/or pharmaceutically acceptable topical carrier, including but not limited to a solution, a suspension, a liquid, a gel, an ointment, a lotion, or a cream. The compositions provide for extended release of MCT and CHT into tissue, promoting collagenesis, scar healing, wound healing, reduction of melasma/chloasma or other skin discoloration, and other benefits to skin.

Cosmetic compositions can be formulated by standard techniques known to ordinarily skilled artisans, such as the techniques described in U.S. Pat. No. 9,980,894 (Herrmann et al.), and U.S. Pat. No. 9,962,464 (Herrmann et al.), both of which are incorporated herein by reference.

Examples of drugs, vitamins and nutrients that can be incorporated into formulations include lipids such as fatty acids, including omega-3 and omega-6 fatty acids, fat soluble vitamins (e.g., vitamin A, D, E, and/or K), water soluble vitamins (e.g., vitamin C, thiamine, riboflavin, niacin, pantothenic acid, vitamin B6, folate, vitamin B12), antibiotics (e.g., amoxicillin, ampicillin, clindamycin, doxycycline, erythromycin, metronidazole, penicillin, tetracycline, vancomycin, and the like), probiotics (e.g., lactic acid bacteria, bifidobacteria, and the like), active dermal compounds (e.g. retinoic acid, tranexamic acid, hydrogen peroxide, hydroquinone, cysteamine, azelaic acid, tyrosinase inhibitors and the like, micronutrients such as β-carotene and/or ascorbic acid, proteins, and peptides.

Such compositions and preparations typically contain at least 0.1% of MCT or MCT-chitosan composite materials. The percentage of the compositions and preparations may, of course, be varied and may conveniently be between about 2% to about 60% of the weight of a given unit dosage form. The amount of MCT and MCT-chitosan composite materials in such therapeutically useful compositions is such that an effective dosage level will be obtained.

Cosmeceutical compositions and the like may also contain the following: binders such as xanthan gum, acacia, corn starch or gelatin; excipients such as di-calcium phosphate; a disintegrating agent such as corn starch, potato starch, alginic acid and the like; and/or a lubricant such as magnesium stearate. Some specific cosmeceutical compositions may contain, in addition to materials of the above type, a liquid carrier, such as a vegetable oil or a polyethylene glycol. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the maintenance of the required particle size in the case of dispersions or by the use of surfactants. The prevention of the action of certain microorganisms can be brought about by various additional antibacterial and antifungal agents, for example, parabens, chlorobutanol, phenol, sorbic acid, thiomersal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin. Of course, any material used in preparing any unit dosage form should be pharmaceutically acceptable and substantially non-toxic in the amounts employed.

For topical administration, the MCT and MCT-chitosan composite materials may be applied in pure form. However, it will generally be desirable to administer them to the skin as compositions or formulations, e.g., in combination with a dermatologically and/or pharmaceutically acceptable topical carrier, which may be a solid or a liquid.

Useful solid carriers include finely divided solids such as talc, clay, microcrystalline cellulose, silica, alumina and the like. Useful liquid carriers include water, dimethyl sulfoxide (DMSO), alcohols or glycols or water-alcohol/glycol blends, in which the MCT or MCT-chitosan composite materials can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the MCT or MCT-chitosan composite materials to the skin are known in the art; for example, see Jacquet et al. (U.S. Pat. No. 4,608,392), Geria (U.S. Pat. No. 4,992,478), Smith et al. (U.S. Pat. No. 4,559,157), and Wortzman (U.S. Pat. No. 4,820,508), all of which are incorporated by reference herein.

Aspects of the present invention provide therapeutic methods of treating various conditions associated with GTR in a mammal, involving administering to a mammal having such a condition an effective amount of MCT or MCT-chitosan composite of one or more embodiments of the invention. A mammal includes a primate, human, rodent, canine, feline, bovine, ovine, equine, swine, caprine, and the like.

The following examples are intended to illustrate aspects of the present invention and should not be construed so as to narrow the inventive scope. One ordinarily skilled in the art will readily recognize that the examples suggest other ways in which the invention could be practiced. It should be understood that numerous variations and modifications may be made while remaining within the scope of the invention.

EXAMPLES

Example 1. MCT-Chitosan Composites:
Preparation, Data, and Applications

Pharmaceutical grade chitosan (deacetylation degree of 92% calculated by $^1$H NMR; mean molecular weight of 185 kDa calculated by specific viscosimetry) was bought from Sigma Aldrich (St. Louis, Mo., USA). The degree of deacetylation and mean molecular weight distribution can be controlled in the production of MCT-chitosan composites to provide chitosan with higher or lower degrees of deacetylation, and/or higher or lower mean molecular weights.

Mutable collagenous tissue (MCT) was isolated from marine invertebrate echinoderms. Adult specimens of the sea urchin, starfish and sea cucumber were collected by scuba divers in China, Tahiti, and Japan, among other locations, and immediately dissected. Samples of sea urchin peristomial membranes, starfish aboral arm walls and sea cucumber whole body walls were collected and stored at −20° C. for the subsequent collagen extraction protocol described by Ferrario C., Leggio L., Leone R., Di Benedetto C., Guidetti L., Coccè V., Ascagni M., Bonasoro F., La Porta C A M, Candia Carnevali M D, Sugni M, "Marine-derived collagen biomaterials from echinoderm connective tissues," Mar Environ Res. Volume 128, pp. 46-57. Animal collection and experimental manipulation were performed according to each country's laws and regulations. Sea urchin (peristomial membranes) and starfish (aboral arm walls) were dissected in small pieces, rinsed in artificial sea water, and left in a hypotonic buffer (10 mM Tris, 0.1% EDTA) for 12 h at room temperature (RT) and then in a de-cellularizing solution (10 mM Tris, 0.1% sodium dodecyl sulfate) for 12 h at RT. After several washings in phosphate-buffered saline (PBS), samples were placed in disaggregating solution (0.5 M NaCl, 0.1 M Tris-HCl pH 8.0, 0.1 M β-mercaptoethanol, 0.05 M EDTA-Na). The obtained MCT suspension was filtered and dialysed against 0.5 M EDTA-Na solution (pH 8.0) for 3 hours at RT and against dH$_2$O overnight at RT. Starfish samples underwent an additional step in 1 mM citric acid (pH 3-4) between decellularizing and disaggregating solutions in order to remove as much as possible the calcium carbonate ossicles present in the fresh tissue. All the steps were carried out under stirring conditions. Sea cucumber MCT was extracted from the whole-body wall following a different protocol. Briefly, the starting tissue was cut into small pieces, placed in PBS and gentamicin (40 µg/mL), and left in stirring conditions at RT for at least 5 days in order to obtain a MCT suspension that was subsequently filtered. Suspensions obtained from the three experimental models were then stored at −80° C. until use.

Figure 5A:
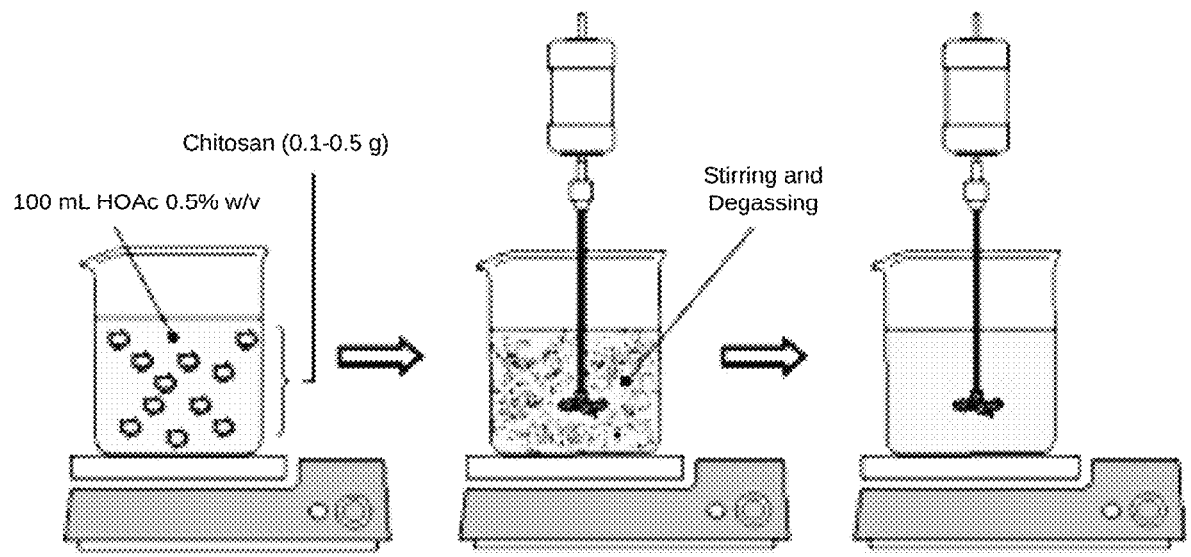
Figure 5B:
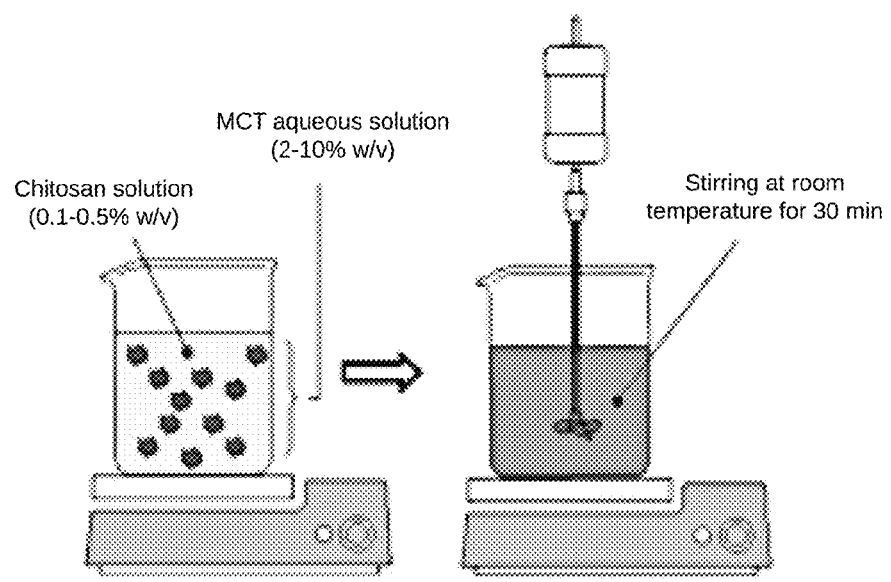

Preparation of MCT-Chitosan Composites:

Mutable collagenous tissues (MCT) were dissolved in acetic acid 0.5% v/v) at room temperature overnight and degassed previous to preparation of biomaterials and composites with chitosan. A chitosan solution was prepared by dissolving chitosan powder in an acetic acid aqueous solution (0.5% v/v) at room temperature (RT). After the chitosan powder was fully dissolved, the solution was filtered and degassed by vacuum filtration. FIG. 5A schematically illustrates the dissolving and degassing of the chitosan solution, according to an embodiment. The chitosan solution (0.1-0.5% w/v) was then mixed with echinoderm isolated MCTs (2.0-10.0% v/v), at different MCT-CHT molar ratios (100:0, 80:20, 60:40, 50:50, 40:60, 20:80 and 10:90) The solution was left to react, with stirring, for 1 hour at RT. FIG. 5B further illustrates the preparation of the MCT-chitosan composites, according to an embodiment. The concentration of chitosan and MCT were controlled in the process of forming composite materials by adding different ratios of the respective components to provide the desired composition.

Figure 6:
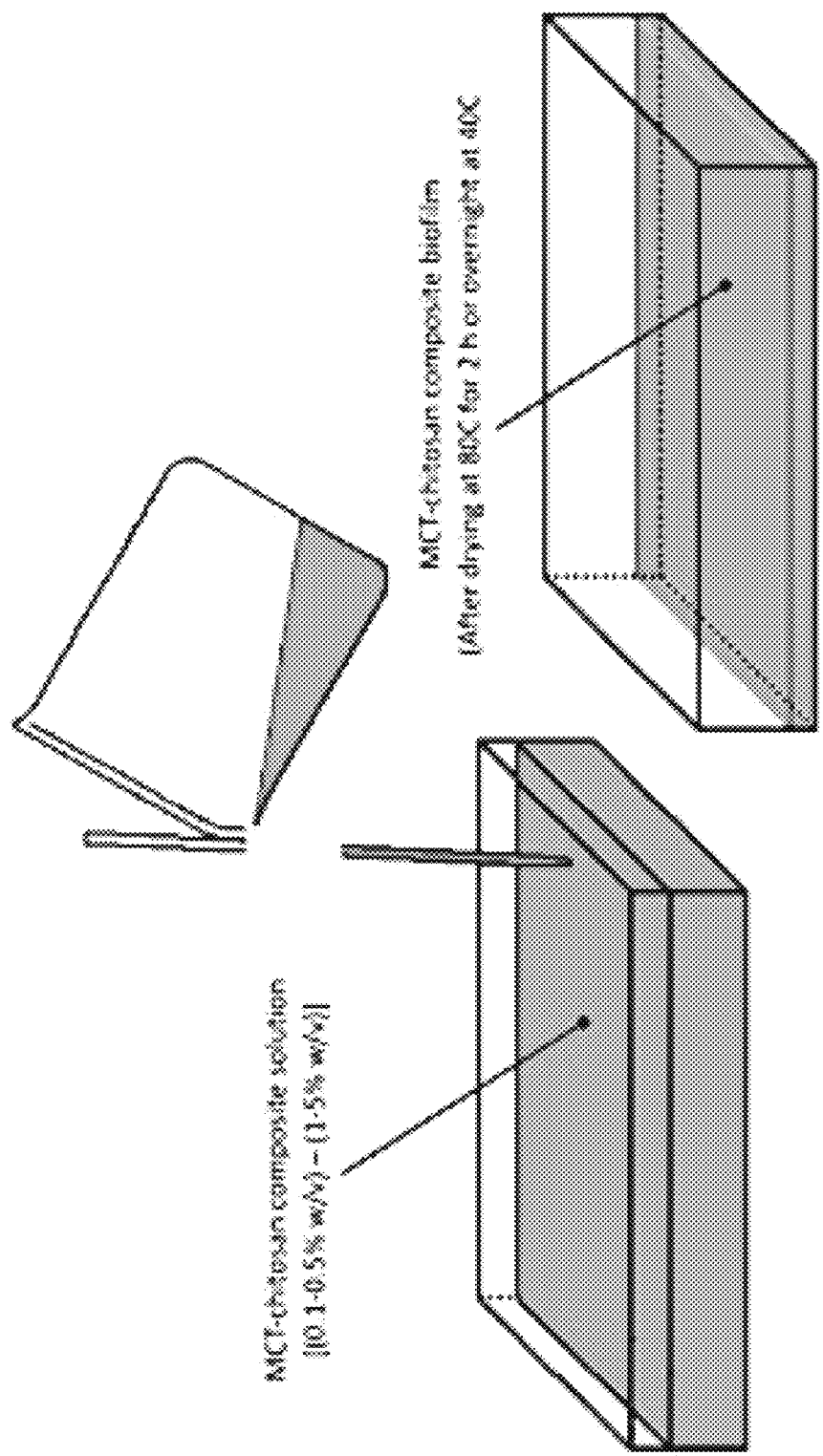

Preparation of MCT-Chitosan Composite Biofilms:

The MCT-chitosan composite solutions were cast onto glass or silicon molds and slowly spread to form even liquid films. The liquid films were then evaporated at 80° C. for 24 hours or overnight at 40° C., to provide 2D cast composite biofilms. FIG. 6 illustrates the casting of the MCT-chitosan biofilms, according to an embodiment.

Figure 7:
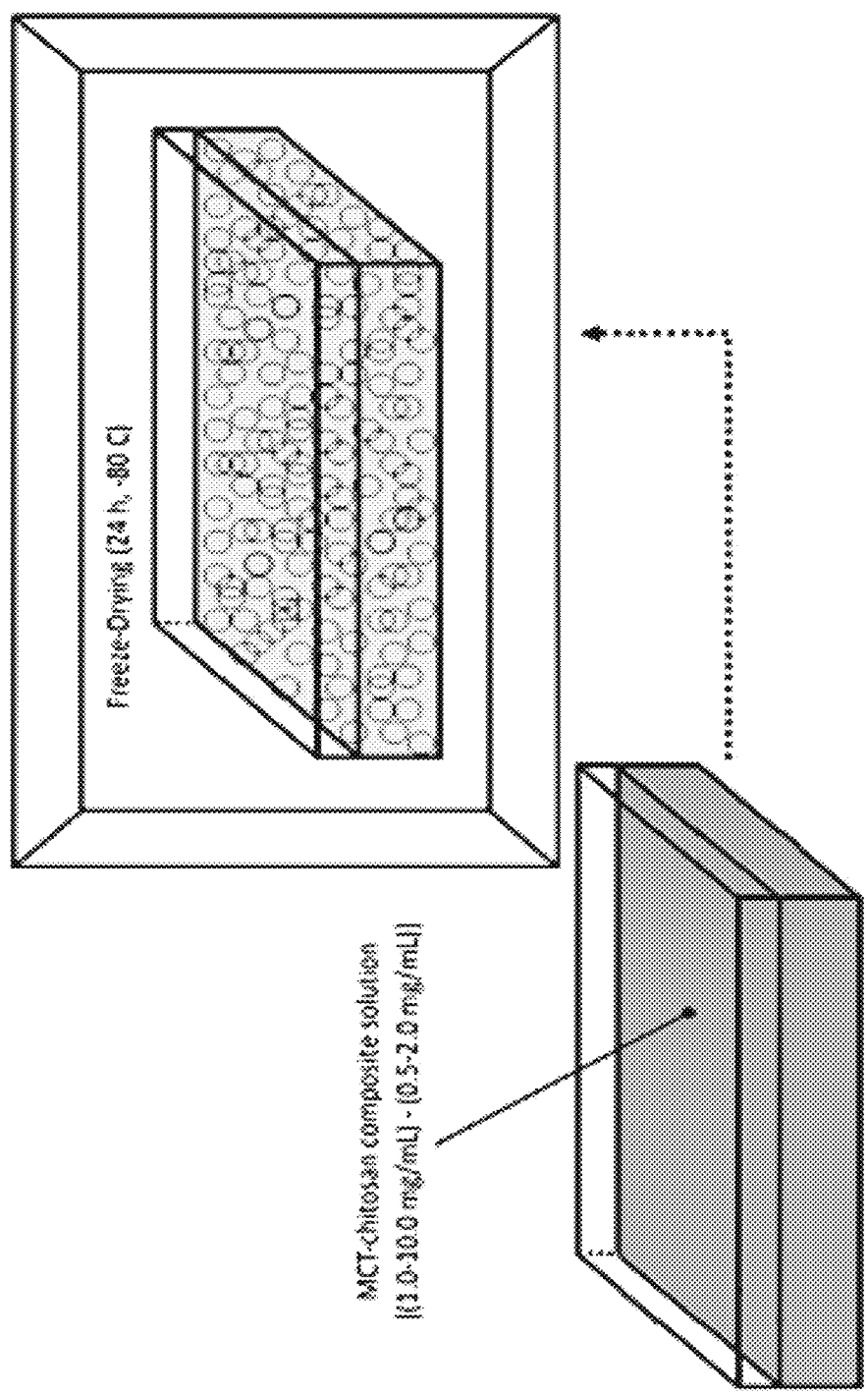

Preparation of MCT-Chitosan Composite 3D-Sponges:

MCT-chitosan 3D-sponges are prepared by a crosslinking method, driven by thermal treatment under vacuum pressure. Composite sponges (diameter=12 mm, thickness=6 mm) were prepared by casting/freeze-drying techniques (Step 3c). One gram of a 2% w/w chitosan solution in water or 0.5% v/v in acetic acid was mixed with MCT aqueous solutions (0.5-2.5% v/v), as FIG. 7 illustrates. The resulting mixture was poured into a glass or silicon mold of adequate size, frozen at −20° C., and freeze-dried to eliminate the solvent, to provide the MCT-chitosan porous 3D-sponge. The MCT-chitosan composite 3D-sponges are physically similar to known chitosan sponges. However, the composite 3D-sponges possess significant additional properties, such as higher water retention (swelling), improved mechanical properties, and superior biocompatibility. The MCT-chitosan composite 3D-sponges can be used, for example, to provide improved wound and hemostatic (blood coagulation) dressings because the hemostatic effect of chitosan is increased by the immunostatic properties of the MCT component. The addition of MCT also improves its mechanical performance, cell attachment and growth.

Figure 8:
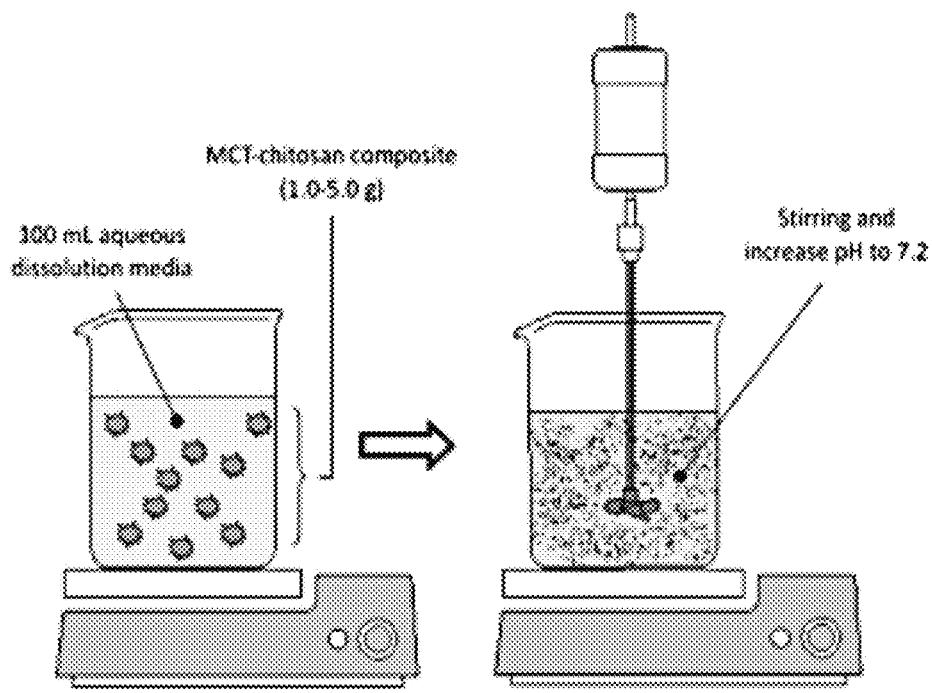

Preparation of MCT-Chitosan Composite Hydrogels:

MCT (2% v/v), chitosan (1% w/v) composite solution was frozen at −20° C. and freeze-dried to eliminate the solvent, leaving a powder material. Two grams of the lyophilized MCT-chitosan composite were dissolved in 100 mL of deionized water and stirred vigorously while the pH was increased dropwise with a concentrated solution of NaOH 6N, as FIG. 8 illustrates. Once the solution reached an adequate pH value (~7.2), a composite hydrogel formed spontaneously, and the viscosity of the dispersion significantly increased. In another embodiment, MCT-chitosan hydrogels can also be fabricated by regulating the final concentration of high molecular weight (HMW) chitosan between 2 to 10% w/v or by mixing the final MCT-chitosan composite with a viscosity enhancer additive, such as hydroxyethyl cellulose, glycerol, or polyethylene glycol, among others.

Figure 9B:
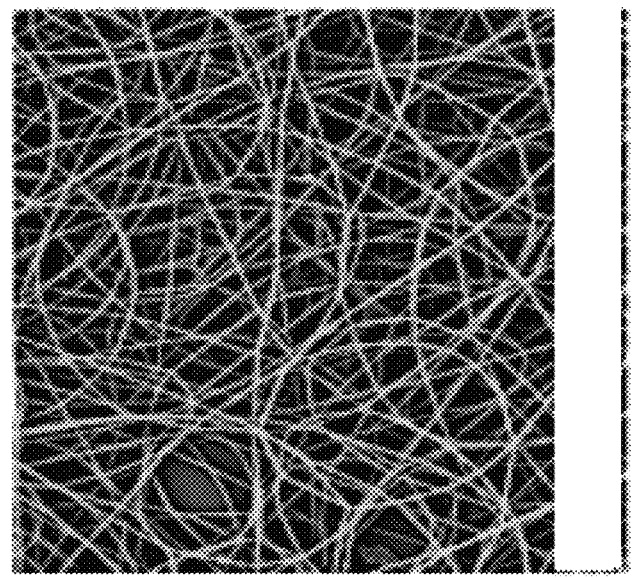
Figure 9A:
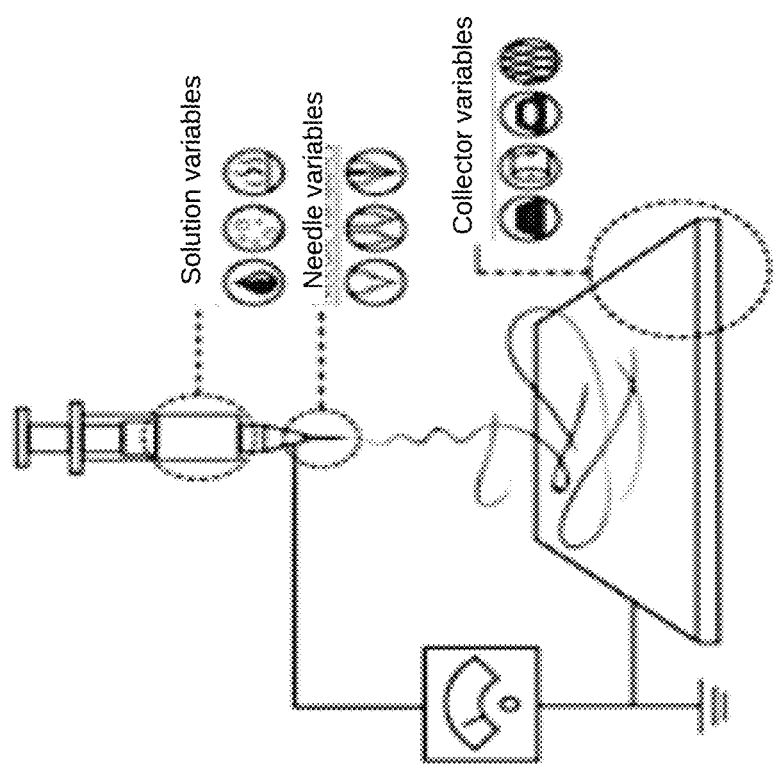

Preparation of MCT-Chitosan Composite Electrospun Nanofibers:

MCT-chitosan non-woven nanofiber mats were prepared by an electrospinning technique, as FIGS. 9A and 9B illustrate. MCT-chitosan composite was dissolved in deionized water at a chitosan concentration ranging from 0.5 to 2.0 (% w/v). The concentration of MCT-chitosan composite was adjusted such that its viscosity and conductivity was suitable for electrospinning. The dispersion was left overnight in a refrigerator (4° C.) for complete hydration prior to electrospinning experiments. The maximum shear rate was according to power-law materials in tubular geometry, with volumetric flow (Q) of $2.78 \times 10^{-10}$ m$^3$/s and an inside radius of the tube of 1 mm (R=$0.5 \times 10^{-3}$ m). To improve MCT-chitosan composite properties for electrospinning, samples were mixed with Polyvinyl alcohol (PVA) as an electrospinning adjuvant. PVA (10% w/v) was dissolved in water at 80° C. under vigorous stirring for 4 h. The MCT-chitosan composite and PVA blended dispersions were mixed at 100:00, 60:40, 50:50, 40:60 and 0:100 mass ratios. MCT-chitosan/PVA blended samples (5 mL) were electrospun using an electrospinning device and a 30-kV power supply (Gamma High Voltage Research, Ormond Beach, Fla., USA). The distance between the needle tip and the collector was set at 20 cm, the voltage was 20 kV, and the solutions were pumped at 1 mL/h. Nanofibers were collected onto aluminum foil and stored in a desiccator for further characterization, as FIG. 9A also illustrates.

Characterization of MCT-Chitosan Biofilms:

The mechanical properties of the MCT-chitosan composite biofilms were evaluated by comparing tensile strength and swelling behavior. Swelling is the first step in the physical degradation of biofilms. Rapid swelling promotes a rapid and uncontrolled release of active compounds (e.g., drugs and/or pesticides) from a biofilm matrix. Glutaraldehyde is commonly added as a cross-linking agent in the production of chitosan biofilms to slow the rate of swelling. A disadvantage of using glutaraldehyde in a hydrogel formulation is a reduction in the tensile strength of the biofilm. MCT-chitosan composite biofilms were cast according to the previous described methodologies. In addition, crosslinked biofilms were formulated by first immersing pre-cast chitosan or MCT-chitosan composite biofilms in a glutaraldehyde solution (0.10% v/v) for 30 minutes, followed by exhaustive washing with deionized water, followed by drying at 80° C. for 2 hours.

Figure 10A:
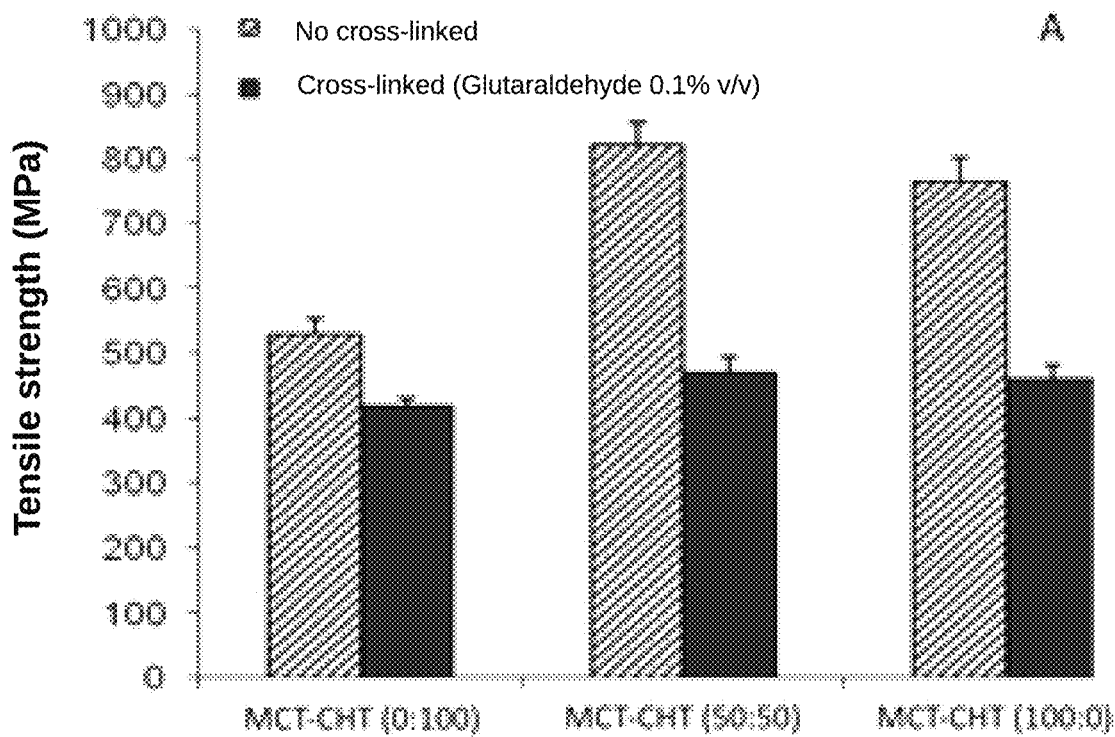
Figure 10B:
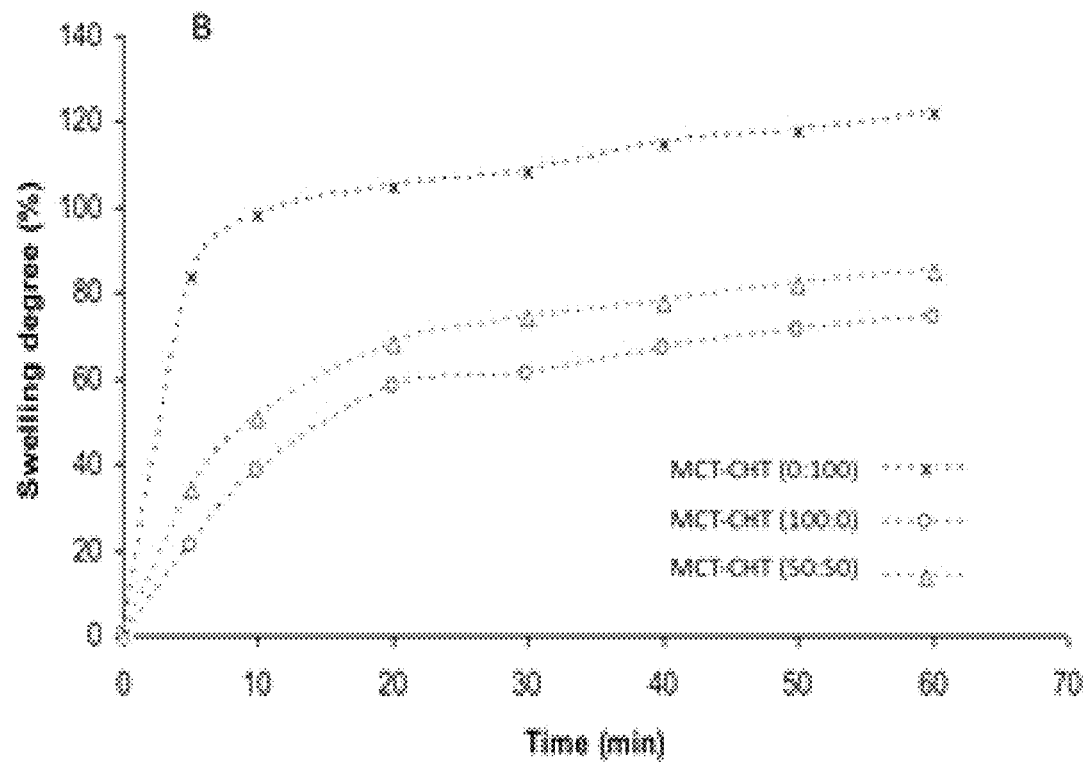

Evaluation of Mechanical Properties:

Tensile strength measurements were performed on a universal mechanical testing machine (model TEST 108 from GT Test, France, equipped with Test Winner 920 software), with a crosshead speed of 10 mm/minute and a 2 kN static load cell. The biofilms were cut into standard tensile samples from a dumbbell-shaped knife (H3 type) with a dimension 17 mm×4 mm×0.08 mm (length×width×thickness). At least five samples of each type of biofilm were tested after a suitable storage period (3 and 20 weeks) at 50±3% RH and 23±2° C. in a humidity chamber (CIAT, France). The maximal tensile stress (TS) was calculated by dividing the maximum load for breaking film by cross-sectional area. MCT-chitosan composite biofilms showed higher tensile strength than the chitosan biofilm alone. FIGS. 10A and 10B illustrate the mechanical behavior of different MCT-chitosan composite biofilms (in 50:50 and 100:0 mass ratio, respectively) compared to chitosan (0:100) alone. Data is shown as [mean±SD; n=5]. The addition of a crosslinking agent (glutaraldehyde) reduced tensile strength of all biofilms relative to the non-crosslinked ones.

Evaluation of Swelling Behavior:

The degree of swelling of chitosan and MCT-chitosan composite biofilms was evaluated by gravimetric methods. Each dry biofilm was first weighed on an analytic balance ($W_d$). After weighing, biofilms were submerged in distilled water for 60 minutes at room temperature. Biofilms were then removed from the water and weighed ($W_s$) at 5, 10, 20, 30, 40, 50, and 60 minutes. Prior to being weighed on a high precision balance, each biofilm sample was quickly taken out from the water bath and blotted with tissue paper to remove excess water. After weighing, the biofilms were returned to the water. The degree of swelling (%) of each biofilm sample was then calculated according to the following equation:

$$\text{Degree of swelling (\%)} = [(Ws-Wd)/Ws] \times 100$$

The results indicate that MCT-chitosan composite biofilms showed lower rates of swelling and lower total degrees of swelling compared to chitosan biofilms alone. FIG. 10B illustrates the degree of swelling for the MCT-chitosan hydrogels as a function of time.

These results indicate that MCT-chitosan composite materials act as a strong cross-linking agent or the equivalent thereof, reducing the swelling of the composite materials while improving the tensile strength of the biofilm. The properties provided by MCT were superior to those of a glutaraldehyde crosslinking agent in chitosan biofilms. MCT are therefore suitable, reliable, and biocompatible 'green alternatives' to glutaraldehyde for formulating biofilms for packaging, patching, and surgical biomaterials.

Characterization of MCT-Chitosan Composite Wound Dressing Templates (Biofilms, 3D-Sponges, and Electrospun Nanofibers): The MCT-chitosan composite wound dressing templates (Biofilms, 3D-sponges and electrospun nanofibers) were characterized according to their chemical profile using attenuated total reflectance Fourier-transform infrared spectroscopy (Nicolet 4700 ATR FT-IR, Thermo Scientific, Grand Island, N.Y., USA), and thermal properties by thermogravimetric analysis (TGA, Q100, TA Instruments, Lindon, Utah, USA). Thermal analysis (DSc and TGA) were performed at 5° C./min over a temperature scan range of 20 to 400° C. in a nitrogen atmosphere (20 mL/min). FIGS. 11A and 11B illustrate MCT-chitosan biofilms and their potential applications as wound dressing templates. The morphology of nanofibers was examined using SEM (Leo 1530-FE, Zeiss, Cambridge, UK). The average fiber diameter was determined by analyzing at least 20 fibers in SEM images using ImageJ software. FIGS. 11C and 11D illustrate the surface morphology.

Advantages of MCT-Chitosan Composite Biomaterials Compared to Chitosan Biomaterials:

The MCT-chitosan composite biomaterials (FIG. 12) provide significantly improved properties for a variety of applications, compared to chitosan biomaterials. The MCT-chitosan composite biomaterials can be prepared as nanoparticles, hydrogels, biofilms, 3D-sponges, or electrospun nanofibers. Each of these forms of biomaterials can be used for various target applications, and each of the composite biomaterials has significant advantages over chitosan biomaterials, as summarized in Table 1 below.

TABLE 1

Improvements of MCT-Chitosan composite compared to chitosan and collagen biomaterials for GTR applications.

| Biomaterial | Target application | Improvement using MCT-chitosan composites |
|---|---|---|
| Biofilms | Controlled drug release | MCT cross-linking effect increases controlled release; can be a replacement for glutaraldehyde |
| | Mechanical properties | MCT-chitosan composite biofilms showed an increase in tensile strength compared to chitosan; the composites are therefore suitable for dressing, patch, and packaging biomaterial applications |
| | Antimicrobial properties | MCT decreases the rate of biodegradation of the biofilms, an important property to promote sustained delivery |
| | Biodegradability Wound healing | MCT immunostatic properties can increase a biofilm's performance as a promoter of wound healing |
| Wound dressing templates (3D-sponges and electrospun nanofibers) | Antimicrobial properties Biocompatibility | MCT can increase mechanical properties in an MCT-chitosan composite when compared to chitosan alone, thereby becoming more active and suitable as dermal patches or bandages |
| | Wound healing and coagulation agent | MCT immunostatic properties can increase wound dressing template performance as wound healing, cell proliferation and coagulation promoters |
| | Cell growth and tissue engineering | MCT-chitosan composite wound dressing template's biocompatibility, antimicrobial properties, and porosity make these composites an advantageous sponging material for tissue engineering and surgical dressing applications |
| Hydrogels | Biocompatibility Additive biomaterial | MCT-chitosan hydrogels can be readily used as additive biomaterials in various formulations (e.g., food, adhesives, pharmaceuticals, biomedical applications) due to their improved mucoadhesion and viscosity, as well as their antimicrobial and immunostatic properties |

Example 2. MCT-Chitosan Composite 3D-Sponges for Applications in GTR, Wound Healing, and Tissue Engineering Chitosan (CHT) has been reported to be biocompatible and bio-absorbable. In particular, CHT is considered to be a good wound-healing accelerator. On the other hand, collagen (MCT) is one of the most widely used matrix biomaterials in tissue engineering. Highly porous MCT single 3D-sponges have been used to support in vitro growth of many types of tissues. Hybrid 3D-sponge biomaterials were fabricated by mixing CHT and MCT, isolated from sea cucumber specimens, at different mass ratios, applying previously developed methodologies involving solvent casting and freeze-drying. MCT/CHT hybrid 3D-sponges were characterized according to their water uptake capacity, mechanical properties, thermal behavior (TGA), and morphology (SEM). Hybrid 3D-sponges showed improved stability, greater porosity, increased thermal stability, and mechanical properties, as well higher biodegradation as compared to single 3D-sponges. Cell culture incubation with adipose tissue-derived stem cell (ADSC) and SEM imaging showed that MCT/CHT hybrid 3D-sponges allowed ADSC adhering, spreading, and growing in vitro.

Fabrication of MCT-Chitosan Hybrid 3D-Sponges:

Chitosan (CHT, 2.0% w/v) was dissolved in acetic acid (0.1% v/v) and slowly mixed with and aqueous collagen solution (MCT, 5% w/v) to produce hybrid solutions in molar ratios of MCT-CHT 100:0, 80:20, 60:40, and 50:50, respectively. MCT-chitosan hybrid 3D-sponges were fabricated by pouring each solution into glass molds, solvent casting, and freeze-drying for 48 hours. The sponges were cut into small fragments (12 mm diameter and 3 mm thickness) for further characterization and cell proliferation studies and storage in a desiccator at a controlled relative humidity.

Physical and Chemical Characterization of MCT-Chitosan Hybrid 3D-Sponges:

Optical microscopy imaging of the fabricated hybrid sponges was collected on an inverted microscope (LIB-305, USA) at 4× magnification. The morphology of MCT-chitosan hybrid 3D-sponges was examined on a scanning electron microscope (SEM, JSM-5200, JEOL, USA) at a magnification of 20kx. The tilt angle of each sample was 30 degrees. Thermogravimetric analysis (TGA) was performed on a TGA-7 instrument (Perkin Elmer, USA). Sponge samples (5-10 mg) were poured into an aluminum holder and analyzed under a nitrogen atmosphere (10 mL/min) at a heating rate of 10° C./min according to a temperature program set up between 50 to 600° C. Uniaxial mechanical compression tests of MCT/CHT hybrid 3D-sponges (n=5 per condition) were performed at ambient conditions (20° C. and 50% relative humidity, RH) by using a universal tensile tester machine (Tensilon RTG, Japan) load cell with a maximum force of 250 N. The compression (mm) and load (N) were collected at a crosshead speed of 5 mm/min. The compressive elastic moduli were calculated as the tangent slope of the stress-strain curves within the initial linear region of the compression curve. The compressive strength was calculated at 15% strain (within the region that the stress-strain curves was linear in all samples). The dry 3D-sponge samples had a cylindrical form with diameter of 12 mm and thickness of 3 mm as measured by electronic micrometer (DMH Series 293, Mitotoyo, Japan).

Cell Attachment and Proliferation Studies:

Adipose tissue-derived stem cells (ADSC) were isolated from living horses. The ADSC (~$10^5$ cells/cm$^2$) were placed on top of each MCT-chitosan hybrid 3D-sponge. A tissue culture plate (polystyrene) well was used as a control. The cultures were placed in the incubator for 1 day, and upon removal were washed with phosphate buffered saline (PBS) and trypsinized. Aliquots of the resulting dissociated cell suspensions were counted on a Coulter counter multisizer (Model 0646, Coulter Electronics, Hialeah, Fla., USA). Only counts between 8 and 32 µm in diameter were used. Cell proliferation was also determined by cell counts as described above after 1, 3, 7 and 10 days in culture. In this experiment, six replicate samples were examined. Attached and/or proliferated ADSC cells were fixed with glutaraldehyde (2.5% v/v) in 0.1 M PBS (pH 7.4) for 30 min and then rinsed with 0.1 M PBS. The fixed cell samples were freeze-dried and sputter-coated with gold for morphological analysis by scanning electron microscopy (SEM, Hitachi Model S-2460N, Hitachi Ltd., Tokyo, Japan).

Data and Statistical Analysis:

All data were reported as mean±standard deviation of at least three replicates. Statistical analysis was done using JMP Pro (Version 10.0.0; SAS Institute Inc., Cary, N.C., USA), settingp=0.05. Results were analyzed with two-way ANOVA models with interaction between the independent variables "sample" and "concentration" to assess significant differences.

Results and Discussion

Physical and Chemical Characterization of MCT-Chitosan Hybrid 3D-Sponges:

Chitosan binds physically to collagen by hydrogen bonding interactions, driven by their available amine and hydroxyl groups. This interaction allows for developing stable biomaterials, such as nanoparticles, biofilms, biofoams, and tissue sponges (Madrigal-Carballo et al., Polymer-liposome nanoparticles obtained by the electrostatic bio-adsorption of natural polymers onto soybean lecithin liposomes, Intl. J. Nanoparticles 5 (3) (2012) 196-209; Madrigal-Carballo et al., Protein-loaded chitosan nanoparticles modulate uptake and antigen presentation of hen egg-white lysozyme by murine peritoneal macrophages, Intl. J. Nanoparticles 3 (2) (2010) 179-191; Ma et al., 'A preliminary in vitro study on the fabrication and tissue engineering applications of a novel chitosan bilayer material as a sponge of human neofetal dermal fibroblasts', Biomaterials, 22(4) (2001), pp. 331-336). FIG. 13A shows the fabricated MCT-chitosan hybrid 3D-sponges. As seen in FIG. 13A, the illustrated hybrid 3D-sponges are fabricated at different MCT/CHT mass ratios (50:50, 60:40, 80:20, and 100:0). FIG. 13B show optical microscopy images of the sponges, and FIG. 13C are SEM micrographs for each fabricated 3D-sponge. In FIG. 13C, the scale bars are 500 µm.

The SEM micrographs in FIG. 13C show a change in the surface morphology of chitosan single sponges when combined with MCT. This change is shown by the decrease in apparent pore size with addition of MCT in the MCT/CHT hybrid 3D-sponge matrix. Thus, MCT interaction with chitosan appears to provide a greater crosslink density, possibly driven by the higher number of potential hydrogen-bonding interactions available between both macromolecules, thus increasing molecular alignment and compactness.

FIG. 14 is a graph of thermal analysis of the MCT-chitosan hybrid 3D sponges by thermogravimetry (TG), showing that the thermal behavior for the MCT/CHT (50:50) hybrid 3D-sponge was intermediate between both MCT/CHT (100:0) and MCT/CHT (0:100) composite sponges. The hybrid 3D-sponge incorporating MCT showed better thermal stability than the chitosan single sponge, with an average temperature of decomposition of 300° C., corresponding to a 15-fold increase in thermal stability when compared to the CHT single sponge.

Biological 3D-sponges need sufficient mechanical properties to maintain their integrity after implantation. Accordingly, a compression test was performed on MCT-chitosan hybrid 3D-sponges to obtain the stress-strain mechanical curves and to calculate both elastic modulus and compressive stress (at 15% strain), respectively, as shown in Table 2. The results show a positive effect on the mechanical properties with the addition of MCT into the chitosan 3D-sponge matrix. The hybrid MCT/CHT (50:50) 3D-sponge showed an increase in compression Young's modulus of about 85-fold, when compared to a MCT/CHT (100:0) sponge. Also, the compressive strength (at 15% strain) was found to increase about 78-fold for the MCT/CHT (60:40) hybrid 3-D sponge system. The observed enhancement in mechanical strength can be associated with the formation of internal, hydrogen-bonded driven, polymeric networks between collagen and chitosan that promote mechanical stabilization of the matrix and thus a suitable 3D-sponge for potential implantation purposes.

TABLE 2

Young's mechanical modulus for different MCT-chitosan hybrid 3D-sponges.
Results are reported mean ± SD (n = 5).

| Sample | Compression Modulus (MPa) | Compressive strength (MPa, at 15% strain) |
| --- | --- | --- |
| MCT/CHT (100:0) | 0.18 ± 0.07 | 0.12 ± 0.01 |
| MCT/CHT (80-20) | 0.34 ± 0.10 | 0.44 ± 0.02 |
| MCT/CHT (60-40) | 0.78 ± 0.55 | 0.51 ± 0.02 |
| MCT/CHT (50-50) | 1.22 ± 0.61 | 0.55 ± 0.03 |

Swelling properties are important in a sponge to promote hydration and cell growth. The MCT-chitosan 3D sponges showed an intermediate behavior between the two simple sponges of MCT and chitosan, with the one having the highest ratio of chitosan showing the highest water absorption capacity. These results can be explained by the presence of more available hydrogen bonding point in the chitosan biomolecule than in the collagen one, due to the reduction of rotation and mobility of the functional groups driven by the quaternary structure of collagen.

FIG. 15 shows the water absorption behavior obtained for different MCT-chitosan hybrid 3D-sponges. In FIG. 15, data are presented as mean±SD, n=3, and (*)=p<0.05, as compared to an MCT/CHT (100:0) single 3D-sponge at same time point. FIG. 15 also includes a picture inserted, for illustrative purposes, to show the swelling behavior of MCT/CHT (50:50) hybrid 3D-sponge. The FIG. 15 graph shows similarity below 70% relative humidity for all the different hybrid 3D-sponges. Meanwhile, after reaching 85% relative humidity, significant differences were observed between the systems as the ratio of MCT was increased in the hybrid 3D-sponge matrix, showing differences in water absorption ranging 250-fold, with the MCT/CHT (50:50) hybrid 3D-sponge showing the highest water absorption capacity, nearly 300%, and the MCT/CHT (100:0) single 3D-sponge showing the lowest water absorption capacity, with values close to 50%. MCT/CHT (80:20) and MCT/CHT (60:40) show water absorption capacity between MCT/CHT (100:0) and MCT/CHT (50:50).

The ability of a composite sponge to preserve water is an important aspect to evaluate its properties and suitability for skin tissue engineering. The water-binding ability of the MCT-chitosan sponge could be attributed to both their hydrophilicity and their maintenance of three-dimensional structure. Chitosan and MCT have abundant hydrophilic groups such as hydroxyl, amino, and carboxyl groups, which are able to retain water in their microstructure. MCT appears to promote an increase in hydrophilicity at higher relative humidity, thus leading to higher water absorption capacities. The water absorption values obtained for the MCT-chitosan sponges agreed with similar experiments previously reported (Ma et al., 'Chitosan porous sponges with improved biostability for skin tissue engineering', Biomaterials. Elsevier, 24(26) (2003), pp. 4833-4841; Chhabra et al., 'Optimization, characterization, and efficacy evaluation of 2% chitosan sponge for tissue engineering and wound healing', Journal of pharmacy & bioallied sciences, Medknow Publications, 8(4) (2016), p. 300).

Adipose Tissue-Derived Stem Cells (ADSC) Growth onto MCT-Chitosan Hybrid 3D-Sponges:

In order to study the interactions between ADSC and MCT-chitosan hybrid 3D-sponges, porous structures of approximately 12 mm diameter and 3 mm thickness were used. After 72 h cultivation, the ADSC reached a confluence higher than 90% on the sponges. SEM images of the cross-section of the MCT/CHT (100:0) 3D-sponge (FIGS. 16A and 16B) showed that after 72 hours of cell seeding, ADSC adhered and spread over the porous MCT-chitosan (100:0) 3D-sponge surface and merged completely with each other so that intercellular connections were not visible (FIG. 16B), when compared to the sponge system with no cells attached (FIG. 16A). In FIGS. 16A and 16B, the scale bar indicates 10 µm. The surface of porous sponges was filled with cells and film that could be secreted ECM precipitation from the cells (Lin, Li and Su, 'Three-dimensional chitosan sponges influence the extra cellular matrix expression in Schwann cells', Materials Science and Engineering C, 42 (2014), pp. 474-478; Ji et al., 'Biocompatibility study of a silk fibroin-chitosan sponge with adipose tissue-derived stem cells in vitro', Experimental and Therapeutic Medicine, 6(2) (2013), pp. 513-518).

FIG. 17 demonstrates the proliferation level to a MCT-chitosan (50:50) composite 3D-sponge after a 15-day incubation period, where the legend (□) indicates a MCT/CHT (100:0) 3D-sponge, the legend (o) indicates a MCT/CHT (0:100) single 3D-sponge, and the legend (Δ) indicates a MCT/CHT (50:50) composite 3D-sponge, and in which data are presented as mean±SD, n=5. (*)=p<0.05, as compared to a MCT/CHT (0:100) single 3D-sponge at same time point. The three graphs depict a 3D-sponge MCT/CHT (0:100), MCT/CHT (100:0), and MCT/CHT (50:50) composite 3D-sponge. The MCT/CHT (50:50) composite 3D-sponge showed significant increase in cell attachment and proliferation, starting at three days of incubation with ADSC, when compared to both MCT/CHT (0:100) and MCT/CHT (100:0) 3D-sponges.

The surfaces of polystyrene dishes have been known to have good cellular attachment and show rapid cellular confluency during incubation (Jeong Park et al., 'Platelet derived growth factor releasing chitosan sponge for periodontal bone regeneration', Biomaterials, 21(2) (2000), pp. 153-159). The extent of cellular attachment and proliferation implies that MCT-chitosan hybrid 3D-sponges have good cellular adaptability. Examining cellular proliferation on the sponge revealed that there was a statistically significant difference between the experimental and control groups after 3 days of incubation with ADSC. This may have resulted from an adaptation process that followed incorporation of the ADSC into the sponge. The fact that the difference between the samples started being significant after 3 days of incubation may have been because of the ADSC demonstrating an initial slow rate of proliferation on the sponge, followed by a return to some more normal proliferation rate three days later. Moreover, the MCT/CHT (50:50) composite 3D-sponge showed significantly increased cell attachment and proliferation. High degrees of cell attachment and proliferation of about 50-fold, were observed from the MCT/CHT (50:50) composite 3D-sponge in contrast to that from MCT/CHT (0:100) and MCT/CHT (100:0) 3D-sponges, for a 15-day incubation period. MCT has been known to stimulate proliferation, chemotaxis and collagenous protein synthesis of osteoblastic cells and ligament fibroblasts (Zhang et al., 'Novel chitosan/collagen sponge containing transforming growth factor-β1 DNA for periodontal tissue engineering', *Biochemical and Biophysical*

Research Communications, 344(1) (2006), pp. 362-369). Also, MCT was reported to enhance the proliferation of progenitor cells (Costa-Pinto et al., 'Adhesion, proliferation, and osteogenic differentiation of a mouse mesenchymal stem cell line (BMC9) seeded on novel melt-based chitosan/polyester 3D porous sponges.', Tissue engineering. Part A, 14(6) (2008), pp. 1049-1057). The combination of MCT and chitosan may be highly beneficial in order to increase the cellular proliferating response.

Conclusions:

In contrast to the quick degradation of collagen, chitosan is slowly biodegraded in vitro. Modifying collagen 3D-sponges with chitosan resulted in improved mechanical strength, thermal stability, biocompatibility, and biodegradability. The MCT-chitosan hybrid 3D-sponges provide multi-dimensional structure for ADSC on both the surface and the inside, with the spatial features for cell attachment, migration and proliferation and facilitate the cell growth. After 72 hours of incubation it was found that ADSC were merged and formed a complete cellular layer on the surface of the sponges, so that the surface was almost covered and only a few pores were visible, and a few cells migrated inside the pores. The MCT-chitosan hybrid 3D-sponges supported ADSC attachment, proliferation and differentiation. SEM images showed that the large surface area of the porous sponges allowed ADSC adhering, spreading and growing on the sponges. The flat morphology, and excellent spreading in and around the interconnected porous structure, indicated strong cellular adhesion and growth of cells. Consequently, MCT-chitosan hybrid 3D-sponges exhibit biocompatibility for ADSC attachment and thus are good candidates for potential applications in tissue engineering.

Example 3. Electrospun MCT-Chitosan Composite Nanofibers as Biocompatible Sponges for Cell Proliferation in Wound Healing and Tissue Engineering Applications Electrospun nanofibers (ESNFs) were prepared from MCT-chitosan composite materials. Polyvinyl alcohol (PVA) was used as an aiding agent. MCT-chitosan/PVA mixed solutions of different volume ratios (100:0, 80:20, 60:40, 40:60, 20:80 and 0:100) were prepared and adjusted to be similar in viscosity and electrical conductivity suitable for electrospinning. Morphology of the ESNFs was examined using scanning electron microscopy (SEM), Fourier transform infrared spectrometer (FTIR), and differential scanning calorimetry (DSC). Studies were used to characterize chemical composition and thermal characteristics of the nanofibers (NFs). The ability of the NFs to support fibroblast cell proliferation was investigated in vitro using the optimized MCT-chitosan/PVA solutions. The results show that MCT-chitosan-based ESNFs are well-suited for fibroblast cell growth, significantly better than ESNFs of PVA. The results also show that MCT-chitosan is better than chitosan alone for supporting cell proliferation.

Preparation of MCT-Chitosan Composites for Electrospinning:

MCT-chitosan powders were swelled in deionized water under vigorous stirring until a homogeneous dispersion (1% v/v) was obtained. The dispersions were left overnight in a refrigerator (4° C.) for complete hydration prior to characterization experiments. MCT-chitosan composite dispersions were characterized by measuring their viscosity by stress-sweep test in a rheometer (C-VOR, Bohlin Instruments, Malvern, UK) with cone-and-plate geometry and electrical conductivity at 25° C. with a conductivity meter (Orion Star A215, ThermoFisher, Waltham Mass., USA) with an electrode conductivity constant of 0.7265 cm$^{-1}$.

Electrospinning of MCT-Chitosan Composites:

MCT-chitosan composites were mixed with aqueous acetone (30% v/v) under vigorous stirring until obtaining a homogeneous dispersion. Concentrations of composite solutions were adjusted so that their viscosities and conductivities were similar and suitable for electrospinning. The dispersion was left overnight in a refrigerator (4° C.) for complete hydration prior to electrospinning experiments. A maximum shear rate was calculated for each MCT-CHT composite sample, according to power-law materials in tubular geometry, with volumetric flow (Q) of $2.78 \times 10^{-10}$ m$^3$/s and an inside radius of the tube of 1 mm (R=$0.5 \times 10^{-3}$ m).

To improve composite properties for electrospinning, samples were mixed with PVA as an electrospinning adjuvant. PVA (10% w/v) was dissolved in water at 80° C. under vigorous stirring for 4 h. The MCT-chitosan composite and PVA blended dispersions were mixed at 100:00, 60:40, 50:50, 40:60 and 0:100 volume ratios. MCT-chitosan/PVA blended samples (5 mL) were electrospun using an electrospinning device and a 30-kV power supply (Gamma High Voltage Research, Ormond Beach, Fla., USA) (see FIGS. 9A and 9B). The distance between the needle tip and the collector was set at 20 cm and the solution was pumped at 1 mL/h. Nanofibers were collected onto an aluminum foil and stored in a desiccator for further characterization.

Characterization of MCT-Chitosan ESNFs:

The ESNFs were characterized according to their chemical profile using attenuated total reflectance Fourier-transform infrared spectroscopy (Nicolet 4700 ATR FT-IR, Thermo Scientific, Grand Island, N.Y., USA), and thermal properties by thermogravimetric analysis (TGA, Q100, TA Instruments, Lindon, Utah, USA). TGA analyses were performed at 5° C./min over a temperature scan range of 100 to 400° C. in a nitrogen atmosphere (20 mL/min). The morphology of nanofibers was examined using SEM (Leo 1530-FE, Zeiss, Cambridge, UK). The average fiber diameter was determined by analyzing at least 20 fibers in SEM images using ImageJ software.

Cell Proliferation Assay:

Cell proliferation was determined by an MTT cell proliferation assay for viable cell numbers. Briefly, ESNFs previously collected under sterile conditions were placed into different wells in a sterile cell culture plate with media and 3 mL of fibroblast cell suspension (L929, 1.5×105) were added into each treatment well. The cell culture plate was placed in an incubator at 37° C. for 3, 7 and 14 days, respectively. After incubation, the media was removed and MTT solution was added into each treatment well in a 1:10 dilution with fresh media. Plates were incubated at 37° C. for 4 h and absorbance was measured at 560 nm using a microplate reader (SpectraMax Plus, Molecular Devices, Sunnyvale, Calif., USA). After cell growth experiments (day 7), ESNFs were collected and washed with media, fixed with glutaraldehyde (2.5% v/v) at 4° C. for 2 h and coated with gold prior to imaging by SEM.

Statistical Analysis:

Statistical analysis was performed using AssistatVR software (Statistics, Arlington, Tex.). Experimental data were presented as mean±SD values. To compare the control group and experimental groups, the data were analyzed by a generalized linear model followed by least mean squares (SAS; Cary, N.C.). The differences were considered statistically significant at $P<0.05$.

FIG. 18 shows graphs of ATR-FTIR spectra of ESNF's of MCT/CHT (0:100) (denoted by "+") and MCT/CHT (100:0) (denoted by "o") separately, and also for two different MCT/CHT composites (60:40, denoted by "*" and 40:60, denoted by "x"). The arrows in the figure indicate changes in nanofiber FTIR spectra associated with the addition of MCT to chitosan. In particular, increased absorption tendencies at both 1650 cm$^{-1}$ and 1000 cm$^{-1}$ can be seen. These correspond respectively to carbonyl (solid arrow) and carbon-oxygen (dashed arrow) stretching frequencies, associated with chitosan's polysaccharide nature. In general, differences between CHT and MCT are apparent in the Figure. For the two composites, there is diversion in certain places in the graph, but in many places, there is substantial overlap, which is not surprising in view of the relatively similar proportions of CHT and MCT.

FIG. 19 shows TGA thermal analysis for MCT/CHT composites (100:0, 60:40, 40:60 and 0:100), indicating a positive effect on chitosan thermal stability resulting from the addition of MCT. MCT-chitosan (60:40) composite shows improved thermal stability over chitosan alone. The MCT-chitosan (60:40) composite shows an average temperature of degradation around 320° C., whereas chitosan alone shows an average temperature of degradation around 280° C.

FIGS. 20A-20F show SEM micrographs of chitosan electrospun nanofibers and MCT-chitosan electrospun nanofibers. In FIGS. 20A and 20D, the scale bar is 10 μm; in FIGS. 21B and 20E, the scale bar is 2 μm and in FIGS. 20C and 20F, the scale bar is 200 nm. The dotted circles indicate presence of drops associated with a poor electrospinning process in chitosan ESNF and show the improvement in ESNFs of MCT-chitosan composites.

FIG. 21 shows proliferation of L929 fibroblast cells co-cultured with chitosan, MCT, and MCT-CHT composite (50:50) ESNF. The Figure shows data from an MTT cell proliferation assay, using PVA ESNFs as a control. The mean percent of viable cells±standard deviations come from experiments carried out three different times. FIGS. 22A-22C are SEM micrographs respectively indicating cell adhesion onto chitosan, MCT-chitosan composite, and MCT.

Conclusions:

MCT-chitosan composite nanofibers were successfully fabricated via electrospinning, using PVA (10% w/v) as an aiding agent. Electrospinning parameters for MCT-chitosan composite nanofiber fabrication were set up and the mass ratio of MCT to chitosan was optimized to 50:50. ATR-FTIR analysis shows the presence of MCT-chitosan components in the ESNFs. Thermal stability of MCT-chitosan composite ESNFs was compared to that of chitosan alone, suggesting that the addition of MCT to chitosan improves thermal stability of ESNFs. Fibroblast cell proliferation results indicate that MCT-chitosan ESNFs are suitable for cell growth and are significantly better than chitosan or MCT ESNFs alone, after 7 days of incubation. SEM images showed that the large surface area of the MCT-chitosan ESNFs allowed good adherence, spread, and growth of L929 fibroblast cells. The results indicate that MCT-chitosan ESNFs improve biocompatibility and activation for fibroblast cell attachment and thus are useful in developing wound dressing templates for applications in tissue engineering, regenerative medicine and as wound healing dressing for treatment of tissue burns.

The following discussion of FIGS. 36-38 provides a summary of structure and application of GTR devices according to embodiments, as well as advantages of those devices.

FIG. 36 shows a 3D-sponge according to an embodiment. In the Figure, the sponge comprises MCT composed of collagen and glycosaminoglycan, which are major components of neodermis. Neodermis is new tissue that forms during wound healing. The collagen-GAG structure of the MCT promotes integrin binding during the healing process. As noted earlier the MCT comes from a marine source, including in one aspect marine invertebrates, in a more particular aspect echinoderms, and in a yet more particular aspect sea urchins and/or sea cucumbers. The ultrastructure of this MCT bears some resemblance to human connective tissue, pointing toward salutary GTR effects such as neodermis formation.

The sponge in FIG. 36 also provides moisture management, to promote wound closure and healing. In one aspect, the sponge has a gelling effect, which promotes patient comfort through a cooling, soothing effect during healing. The crosslinking treatment of the MCT enables the sponge to be effective for up to 30 days, because the resulting structure exhibits low physical degradation and resistance to proteolytic enzymes. In particular, the resulting structure targets and deactivates excess enzymes, such as matrix metalloproteinases (MMPs), which can degrade proteins. Such targeting and deactivation promote and improve wound closure and healing.

FIG. 37 depicts a 3D-sponge according to some embodiments. The sponge may be composed of MCT, or of a matrix of MCT-CHT, depending on the embodiment. This material in the sponge supports tissue and blood vessel ingrowth. Other aspects of the sponge structure include an absorbent, gel-forming composition which maintains a moist environment and controls exudate, promoting healing and tissue regeneration.

FIG. 38 depicts a GTR device, which may be composed of MCT or a matrix of MCT-CHT, sutured into an opening in skin as part of treatment. The figure shows the sutures around the device, as well as neodermis which is forming beneath the device, as a part of the healing process. A portion of FIG. 38 shows an exploded view of the neodermis, displaying the MCT, alone or in a composite matrix with CHT, with integrin binding sites.

Example 4. Cosmeceutical Dosage Forms

The following formulations illustrate representative pharmaceutical dosage forms that may be used for the therapeutic or prophylactic administration of MCT and MCT-chitosan (MCT-CHT) composition described herein, employing a dermatologically and/or pharmaceutically acceptable topical carrier, including but not limited to a solution, a suspension, a liquid, a gel, an ointment, a lotion, or a cream. In the following examples, a gel or a cream is provided:

| (i) GTR Gel | % by weight |
|---|---|
| Part A | |
| MCT or MCT-CHT composite | 2.0 |
| Polyethylene oxide | 0.4 |
| Carbopol | 0.4 |
| Water | 90.9 |
| Part B | |
| Ethoxylate glycerin | 0.5 |
| Polyethylene glycol oleyl ether | 1.0 |
| Diethanolamine oleth-3 phosphate | 0.8 |
| Crodamol PMP | 0.5 |
| Ethoxylated glucose methyl ester | 0.7 |

| (i) GTR Gel | % by weight |
|---|---|
| Part C | |
| Triethanolamine | 0.4 |
| Fragrance | 0.1 |

This formulation is prepared in separate stages as follows: Part A of the mixture was prepared by dispersing the Carbopol in water and then stirring in the other components. All the Part B components were mixed together and heated to 70° C. Parts A and B were then combined and the triethanolamine and fragrance were added (Part C). The resulting cream was stable and smooth and had good moisturizing qualities and an excellent feel on the skin.

| (ii) GTR Cream 1 | % by weight |
|---|---|
| MCT or MCT-CHT composite | 2.5 |
| Polyethylene oxide | 0.3 |
| Glycerine | 5.0 |
| Ethyl alcohol | 15.0 |
| Oleth-5 | 2.0 |
| Ethoxylated glucose methyl ester | 0.7 |
| Preservative | 0.3 |
| Fragrance | 0.15 |
| Water up to | 100.0 |

The formulation was prepared by mixing all the components together.

| (iii) GTR Cream 2 | % by weight |
|---|---|
| Part A | |
| MCT or MCT-CHT composite | 2.5 |
| Polyethylene oxide | 1.5 |
| Carbopol | 0.5 |
| Water | 83.5 |
| Part B | |
| Petrolatum | 5.0 |
| Polyethylene glycol stearate | 2.5 |
| Diethanolamine oleth-3 phosphate | 2.0 |
| Silicone copolymer | 1.5 |
| Preservative | 0.3 |
| Part C | |
| Triethanolamine | 0.5 |
| Fragrance | 0.1 |

This formulation is prepared in separate stages as follows: Part A of the mixture was prepared by dispersing the Carbopol in water and then stirring in the other components. All the Part B components were mixed together and heated to 70° C. Parts A and B were then combined and the triethanolamine and fragrance were added (Part C). The resulting cream was rich with excellent moisturizing qualities and did not give a greasy feeling on the skin.

| (iv) Scar cream composition | | |
|---|---|---|
| Ingredient | Weight (mg) | Composition (%) |
| Astaxanthin | 50 | 0.05 |
| Vitamin E | 150 | 0.15 |
| Royal Jelly | 100 | 0.10 |
| Moringa/Vitamin C extract | 200 | 0.20 |
| MCT or MCT-CHT composite | 1000 | 1.00 |
| Cream Base | q.s. | 95.00 |
| Total Volume | 100 mL | |

Preparation Procedure:
1—Weigh 150 mg of Vitamin E and mix it with the cream base dispersion under gentle stirring.
2—Weigh 1000 mg of MCT-CHT lyophilized powder (formulated at MCT:CHT mass ratios 100:0 to 70:30) and dissolve it in 5.00 mL of acetic acid (0.5M) prepared in distilled water (pH 3.2).
3—Weigh 200 mg of Moringa/Vitamin C extract and dissolve it in the aqueous solution of MCT-CHT.
4—Weigh 50 mg of Astaxanthin and dissolve it in the aqueous solution containing MCT-CHT and Moringa/Vitamin C extract.
5—Weigh 100 mg of Royal Jelly and mix it with the aqueous solution containing MCT-CHT, Moringa/Vitamin C extract and Astaxanthin.
6—Mix the aqueous solution containing MCT-CHT, Moringa/Vitamin C extract and Astaxanthin with the cream base containing Vitamin E, under continuous and gentle stirring, until a homogeneous dispersion is reached.
7—Pour the homogenized Scar Cream formulation into an adequate glass container and store at room temperature.

The above-described formulations may be prepared by conventional procedures well known in the pharmaceutical art. It will be appreciated that the above cosmeceutical compositions may be varied according to well-known pharmaceutical techniques to accommodate differing amounts and types of the MCT-CHT composite as the active ingredient.

The just-described scar cream composition was applied to several patients. FIGS. 30A and 30B show before and after results for one patient. FIG. 30A is a picture of a five-year-old scar from a Caesarean section, before application of the above-listed scar cream. FIG. 30B is a picture of the same scar after daily application of the scar cream for two weeks. As is evident from FIG. 30B, the scar after treatment is shorter, and has a different color, closer to the color of the surrounding skin.

FIGS. 31A and 31B show before and after results for another patient. FIG. 31A is a picture of a 15-year-old scar below a left knee joint, before application of the above-listed scar cream. FIG. 31B is a picture of the same scar after application of the scar cream. As is evident from FIG. 31B, the scar has a different color, closer to the color of the surrounding skin.

FIGS. 32A to 32C show before and after results for yet another patient. FIG. 32A is a picture of a 25-year-old appendectomy scar, before application of the above-listed scar cream. FIG. 32B is a picture of the same scar after daily application, and FIG. 32C is a picture of the same scar after eight days of daily application of a scar cream according to an embodiment. As is evident from FIGS. 32B and 32C, the scar after treatment is shorter, and has a different color, closer to the color of the surrounding skin.

FIGS. 33A and 33B show before and after results for yet another patient. FIG. 33A is a picture of a six-month-old scar from knee surgery, and FIG. 33B is a picture of the same scar after seven days of daily application of the above-listed scar cream. As is evident from FIGS. 33A and 33B, the scar after treatment is much less prominent than before, and has a different color, closer to the color of the surrounding skin. The patient experienced no adverse effects or hyperplasia.

FIGS. 34A-D show progressive results for yet another patient in the treatment of a scar. FIG. 34A shows a picture of a burn scar, FIGS. 34B and 34C show pictures of the scar during daily application of the above-listed scar cream, and FIG. 34D shows a picture of the scar after seven days of treatment. As is evident from these figures, the scar after treatment is substantially healed, with a color closer to the color of the surrounding skin as compared to the appearance of the scar before treatment.

In addition to the foregoing treatment examples, scar formation can occur in various areas of the body, including in and around eyelids, for example, as a result of injury, surgery, plastic surgery, or other repair and/or healing procedures. The above-described scar cream has been used in this kind of treatment as well, to good effect.

As part of the foregoing work as described, and the produced examples, work was done to determine and show structural differences between MCT extracted from sea cucumbers, and bovine collagen isolated from calf-skin tissue. Amino acid composition analysis of collagen samples was determined as described in (Cui F., Li Z., Zhang Y., Dong P., Fu X., Gao X., "Characterization and Subunit Composition of Collagen from the Body Wall of Sea Cucumber," *Stichopus Japonicus*," Food Chem. 100(3) (2007): 1120-5.). Briefly, collagen samples were hydrolyzed by 6 M HCl at 110° C. for 24 h, then the major amino acid composition of the hydrolysate was analyzed using a SYKAM amino acid analyzer S433D (SYKAM, Munich, Germany).

Table 3 below shows amino acid composition for different MCT samples isolated from sea cucumber, and bovine (calf-skin) collagen isolated from calf-skin. The analysis for calf-skin collagen samples 1-4 in the table below were carried out in research which may be found in the following articles: X. Cheng, Z. Shao, C. Li, L. Yu, M. A. Raja, C. Liu, "Isolation, Characterization and Evaluation of Collagen from Jellyfish *Rhopilema esculentum* Kishinouye for Use in Hemostatic Applications," PLOS One, 2017, 0169731; Y. Han, J-R. Ahn, J-W. Woo, C-K. Jung, S-M. Cho, Y-B. Lee, S-B. Kim, "Processing Optimization and Physicochemical Characteristics of Collagen from Scales of Yellowfin Tuna (*Thunnus albacares*)," Fisheries and Aquatic Sciences, Volume 13, Issue 2, 2010, pp. 102-111; H. Li, B. L. Liu, L. Z. Gao, H. L. Chen, "Studies on bullfrog skin collagen," Food Chemistry, Volume 84, Issue 1, January 2004, pp. 65-69; P. Kittiphattanabawon, S. Nalinanon, S. Benjakul, and H. Kishimura. "Characteristics of Pepsin-Solubilised Collagen from the Skin of Splendid Squid (*Loligo formosana*)," Journal of Chemistry, Volume 2015, Article ID 482354, 8 pages.

TABLE 3

Amino acid compositions

| Amino Acid | Code | Composition (% w/w) | | | | | |
|---|---|---|---|---|---|---|---|
| | | MCT 1 | MCT 2 | Calf-skin Collagen 1 | Calf-skin Collagen 2 | Calf-skin Collagen 3 | Calf-skin Collagen 4 |
| CYS | C | 0.00 | 0.00 | 0.00 | 0.00 | 0.00 | 0.00 |
| HYP | Z | 7.33 | 7.46 | NR | 9.06 | 8.60 | 9.40 |
| ASP | D | 9.23 | 8.42 | 4.93 | 5.11 | 4.50 | 4.50 |
| THR | T | 4.37 | 3.38 | 2.35 | 1.85 | 1.80 | 1.80 |
| SER | S | 3.47 | 4.10 | 4.09 | 2.85 | 3.70 | 3.90 |
| GLU | E | 13.46 | 14.01 | 7.84 | 10.69 | 7.10 | 7.50 |
| PRO | P | 12.21 | 11.99 | 11.69 | 10.88 | 13.50 | 12.10 |
| GLY | G | 19.13 | 19.64 | 32.56 | 16.28 | 32.50 | 33.00 |
| ALA | A | 9.22 | 9.99 | 12.91 | 8.12 | 11.20 | 11.90 |
| VAL | V | 2.53 | 2.60 | 3.97 | 2.27 | 2.20 | 2.10 |
| MET | M | 0.65 | 0.61 | 0.86 | NR | 0.60 | 0.60 |
| ILE | I | 1.72 | 1.64 | 2.35 | 1.37 | 1.10 | 1.10 |
| LEU | L | 2.73 | 2.83 | 3.82 | 2.86 | 2.50 | 2.30 |
| TYR | Y | 1.46 | 1.24 | 0.91 | 0.48 | 0.30 | 0.30 |
| PHE | F | 1.42 | 1.19 | 1.94 | 1.84 | 1.30 | 0.30 |
| HIS | H | 0.33 | 0.24 | 0.06 | 1.96 | 0.50 | 0.50 |
| LYS | K | 0.65 | 0.50 | 4.27 | 0.27 | 2.70 | 2.60 |
| ARG | R | 8.54 | 8.65 | 5.36 | 4.19 | 5.10 | 5.10 |

Table 3 shows the amino acid compositions of mutable collagenous tissue (MCT) and bovine collagen (BC). The major amino acids of MCT were glycine (19.0%), glutamic acid (14.0%), proline (12.0%), alanine (9.0%), aspartic acid (9.0%), Arginine (8.0%) and hydroxyproline (6.7%), which were similar from those found in bovine collagen shown in Table 4 (see references).

The primary structure of type I collagen is characterized as containing domains with continuous repeating of Gly-X-Y sequence (where X is mostly proline and Y is mostly hydroxyproline), and the very short N- and C-terminal regions called telopeptides (15 to 26 amino acid residues). The Gly-X-Y repeating sequence in α1 chain plays an important role in triple helix formation of secondary structure. See Gelse K, Pöschl E, Aigner T. 2003. Collagens-structure, function, and biosynthesis. Adv Drug Deliver Rev 55(12):1531-46; Gómez-Guillén M, Giménez B, López-Caballero M, Montero M. 2011. Functional and bioactive properties of collagen and gelatin from alternative sources: a review. Food Hydrocolloid 25(8):1813-27. As an amino acid with the lowest molecular weight, glycine residues arranged in the center of triple helix can help helix structure to fold compactly [3]. See Fraser R, MacRae T, Suzuki E. 1979. Chain conformation in the collagen molecule. J Mol Biol 129(3):463-81. Therefore, glycine is the major amino acid in bovine collagen. According to previous references, the glycine content in bovine collagen ranges from 14 to 33%, about one-quarter of total amino acid, that was consistent with MCT glycine content (19%).

FIGS. 23 and 24 show results of purity analyses of collagen matrices for marine collagen as compared to calf and chicken collagen and show that marine collagen is as safe as calf and chicken collagen, and therefore is sufficiently safe to be used in the just-described applications. These figures show a triple helix structure, where the broad blue band on the bottom is an alpha helix, with a beta or gamma helix on top. MCT 1 and MCT 2 in these figures indicate different MCT batches, showing reproducibility of results.

In FIG. 25A, the peaks denoted by "+" on the right-hand side of the figure show hydrolyzing of calf collagen to make it soluble. The comparative graph denotes MCT by "o". FIG. 25B shows comparable FTIR spectra, indicating the reproducibility of results with respect to efficacy of the MCT isolation process for sea cucumber, with MCT1 being denoted by "*" and MCT2 by "x". FIG. 25B shows a high degree of consistency in MCT chemical profile from batch to batch.

FIG. 26 shows the results of themogravimetric analysis (TGA) of collagen samples and shows differences in thermal behavior for MCT samples. In FIG. 26, lessened stability is shown as the lines head toward the bottom of the graph. The line for calf collagen shows increasing instability at 280° C., whereas the lines for MCT1 and MCT2 show stability even at 400° C. The graph shows better thermal stability for MCT than for calf collagen, indicating an improved ability to store MCT-based products.

Imino acids (proline and hydroxyproline) are important amino acids composing Gly-X-Y repeat sequences in a chain, because of their ability to maintain the stability of collagen triple helix with their pyrrolidine rings. See Wong, D W. 1989. Mechanism and theory in food chemistry. New York: Van Nostrand Reinhold. The contents of proline and hydroxyproline in MCT were 12.0 and 7.0%, respectively, for a total imino acid content of 20.0%, slightly lower than the values found for bovine collagen, as FIG. 27 shows.

The contents of proline and hydroxyproline are found to be related to environmental temperature. See Zhong M, Chen T, Hu C, Ren C. 2015. Isolation and Characterization of Collagen from the Body Wall of Sea Cucumber *Stichopus monotuberculatus*. Food Chem 80(4):C671-C679. However, when compared to bovine collagen, the ratio of Gly to imino acid (Hyp/Pro) content is lower, thus suggesting a more efficient stabilization of the Gly-based triple helix by imino acids in MCT.

Collagen stability can be affected by amino acid composition, especially imino acids. Proline (PRO) and hydroxyproline (HYP) can maintain collagen spatial structure with pyrrolidine rings, whereas hydroxyl groups of hydroxyproline form hydrogen bonds with adjacent chain to improve stability of triple helix. Amino acid composition analysis of MCT indicate a high presence of glycine and imino acids, suitable for the formation of a stable collagen triple-helix showing a lower degradation rate than bovine collagen.

FIG. 27 is a bar graph of GLY, HYP, PRO and imino acid (sum of HYP and PRO) for MCT1 and MCT2 samples, as compared with several samples of calf collagen. One of the very favorable aspects of MCT is the almost 1:1 ratio, reproducible consistently, of GLY to imino acids. In comparison, even the most favorable calf collagen sample, in the middle of the Figure, does not show as close to a 1:1 ratio as do the MCT1 and MCT2 samples. A high content of GLY compared to imino acids indicates less stability. While high GLY content is favorable, the 1:1 ratio of GLY to imino acids indicates greater stability.

FIGS. 28A and 28B, and FIGS. 29A and 29B are scanning electron microscopy (SEM) pictures of MCT formed in two different ways. FIGS. 28A and 28B show the results of using a solvent casting technique to form the MCT-chitosan composite. FIG. 28A shows the morphology of the structure of a MCT-chitosan dressing template (e.g. a 3D sponge). FIG. 28B indicates a high degree of porosity for the structure. FIGS. 29A and 29B show the results of using an electrospinning technique to form the MCT-chitosan dressing template. As in FIGS. 28A and 28B, respectively, FIG. 29A shows the morphology of the structure, and FIG. 29B indicates a high degree of porosity for the structure. Porosity is an important attribute in guided tissue regeneration, to promote cell attachment and growth.

All referenced publications, patents, and patent documents are incorporated by reference herein, as though individually incorporated by reference. Additionally, various aspects of the invention have been described with reference to various specific and preferred embodiments and techniques. However, it should be understood that many variations and modifications may be made within the spirit and scope of the invention.

What is claimed is:

1. A topical composition to treat skin abnormalities, the composition comprising:
   mutable collagenous tissue (MCT) and high molecular weight chitosan, wherein the high molecular weight chitosan is present in an effective amount as a mass percentage greater than zero, wherein the high molecular weight chitosan is electrostatically bonded to the MCT to form a matrix, and the matrix of high molecular weight chitosan and MCT is in the form of a MCT-chitosan composite material; and
   a pharmaceutically acceptable topical carrier.

2. The composition of claim 1, to treat scars.

3. The composition of claim 1 to promote eyelid recovery.

4. The composition of claim 1, to treat skin discoloration.

5. The composition of claim 4, to treat chloasma.

6. The composition of claim 1, wherein the pharmaceutically acceptable topical carrier is selected from the group consisting of a solution, a suspension, a liquid, a gel, an ointment, a lotion, or a cream.

7. The composition of claim 6, wherein the pharmaceutically acceptable topical carrier is a gel.

8. The composition of claim 6, wherein the pharmaceutically acceptable topical carrier is a cream.

9. The composition of claim 1, wherein the MCT is isolated from invertebrate marine organisms selected from the group consisting of echinoderms.

10. The composition of claim 9, wherein the MCT is isolated from echinoderms, selected from the group consisting of sea cucumbers.

11. The composition of claim 1, wherein the MCT comprises collagen and glycosaminoglycan (GAG).

12. The composition of claim 1, wherein the MCT consists of fibrillar collagen selected from the group consisting of type I, or a mixture of two or more of type I and type II.

13. The composition of claim 11, wherein the glycosaminoglycan is selected from the group consisting of chondroitin sulfate, and hyaluronic acid, or a mixture of chondroitin sulfate and hyaluronic acid.

14. The composition of claim 1, wherein a mass ratio of MCT to high molecular weight chitosan is selected from the group consisting of 10:90, 20:80, 40:60, 50:50, 60:40, 80:20, or 90:10.

15. The composition of claim 11, wherein the MCT-chitosan composite comprises a polyelectrolyte crosslinked structure between GAG and high molecular weight collagen in MCT with N-glucosamine units on high molecular weight chitosan.

16. The composition of claim 1, wherein the high molecular weight chitosan has a molecular weight MW of 150 kDa≤MW≤300 kDa.

17. The composition of claim 1, wherein the high molecular weight chitosan has a degree of deacetylation of at least about 90%.

* * * * *